US008778631B2

(12) United States Patent
Voloshin et al.

(10) Patent No.: US 8,778,631 B2
(45) Date of Patent: Jul. 15, 2014

(54) MONO CHARGING SYSTEM FOR SELECTIVELY INTRODUCING NON-NATIVE AMINO ACIDS INTO PROTEINS USING AN IN VITRO PROTEIN SYNTHESIS SYSTEM

(75) Inventors: Alexei M. Voloshin, South San Francisco, CA (US); James F. Zawada, South San Francisco, CA (US); Daniel Gold, South San Francisco, CA (US); Christopher James Murray, Soquel, CA (US); James Edward Rozzelle, San Francisco, CA (US); Nathan Uter, South San Francisco, CA (US); Gang Yin, South San Francisco, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 456 days.

(21) Appl. No.: 12/685,795

(22) Filed: Jan. 12, 2010

(65) Prior Publication Data

US 2010/0184135 A1 Jul. 22, 2010

Related U.S. Application Data

(60) Provisional application No. 61/144,097, filed on Jan. 12, 2009, provisional application No. 61/144,083, filed on Jan. 12, 2009, provisional application No. 61/144,030, filed on Jan. 12, 2009.

(51) Int. Cl.
*C07K 1/00* (2006.01)
*C07K 17/00* (2006.01)

(52) U.S. Cl.
USPC .......... 435/68.1; 435/183; 435/69.2; 530/350

(58) Field of Classification Search
None
See application file for complete search history.

(56) References Cited

U.S. PATENT DOCUMENTS

| | | | |
|---|---|---|---|
| 5,801,013 | A | 9/1998 | Tao et al. |
| 6,977,150 | B2 | 12/2005 | Forster et al. |
| 7,312,049 | B2 | 12/2007 | Calhoun et al. |
| 2005/0053985 | A1 | 3/2005 | Trotta et al. |
| 2005/0287639 | A1 | 12/2005 | Kwon et al. |
| 2006/0068449 | A1 | 3/2006 | Rothschild et al. |
| 2008/0254540 | A1 | 10/2008 | Wang et al. |

FOREIGN PATENT DOCUMENTS

| | | | |
|---|---|---|---|
| WO | WO 03/070740 | A1 | 8/2003 |
| WO | WO 2006/138322 | A2 | 12/2006 |
| WO | WO 2007/059312 | A2 | 5/2007 |
| WO | WO 2007/103307 | A2 | 9/2007 |
| WO | WO 2008/028862 | A1 | 3/2008 |

OTHER PUBLICATIONS

International Search Report from International Application No. PCT/US2010/020671, dated Apr. 6, 2010.

International Search Report from International Application No. PCT/US2010/020672, dated Apr. 13, 2010.

Cload et al.; "Development of improved tRNAs for in vitro biosynthesis of proteins containing unnatural amino acids"; *Chem. and Biol*.; 3:1033-1038 (1996).

de Zamaroczy et al.; "Cleavage of Colicin D Is Necessary for Cell Killing and Requires the Inner Membrane Peptidase LepB"; *Mol. Cell*. 8:159-168 (2001).

Doring et al.; "Enlarging the Amino Acid Set of *Escherichia coli* by Infiltration of the Valine Coding Pathway"; *Science*, 292:501 (2001).

Ellman et al.; "Site-specific incorporation of novel backbone structures into proteins"; *Science*, 255:197-200 (1992).

Graille et al.; "Structural inhibition of the colicin D tRNase by the tRNA-mimicking immunity protein"; *EMBO J*.; 23: 1474-1482 (2004).

Jewett et al.; "An integrated cell-free metabolic platform for protein production and synthetic biology"; *Mol. Sys. Biol*.; 4:220 (2008) Epub Oct. 14, 2008.

Kanatani et al. "A simple approach to sense codon-templated synthesis of natural/unnatural hybrid peptides"; *Nucleic Acids Symposium Series*; 49:265-266 (2005).

Kanda et al.; "Sense Codon-Dependent Introduction of Unnatural Amino Acids into Multiple Sites of a Protein"; *Biochem. Biophys. Res. Commun*.; 270:1136-1139 (2000).

Masuda et al.; "Isolation of temperature-sensitive aminoacyl-tRNA synthetase mutants from an *Escherichia coli* strain harboring the *pemK* plasmid"; *Mol. Gen. Genet*.; 238:169-176 (1993).

Noren et al.; "A general method for site-specific incorporation of unnatural amino acids into proteins"; *Science*, 244:182-188 (1989).

Raskin, I.; "Role of salicylic acid in plants"; *Ann. Rev. Plant Physiol. Plant Mol. Biol*.; 43:439-463.

Salazar et al.; "Coevolution of an aminoacyl-tRNA synthetase with its tRNA substrates"; *Proc. Natl. Acad. Sci. USA*; 100(24):13863-13868 (2003).

Sando et al.; "A small-molecule-based approach to sense codon-templated natural-unnatural hybrid peptides. Selective silencing and reassignment of the sense codon by orthogonal reacylation stalling at the single-codon level"; *J. Am. Chem. Soc*.; 127:7998-7999 (2005).

Sayers et al.; "5'-3' Exonucleases in phosphorothioate-based oligonucleotide-directed mutagenesis"; *Nucleic Acids Res*., 16:791-802 (1988).

Schmidt et al.; "Dominant lethality by expression of a catalytically inactive class I tRNA synthetase"; *Proc. Natl. Acad. Sci. USA* ; 90:6919-6923 (1993).

Takahashi et al.; "Alteration of Aminoacyl-tRNA Synthetase with Age: Heat-Labilization of the Enzyme by Oxidative Damage". *Arch. Biochem. Biophys*.; 277(2):228-233 (1990).

(Continued)

*Primary Examiner* — Kagnew H Gebreyesus

(74) *Attorney, Agent, or Firm* — Kilpatrick Townsend and Stockton LLP

(57) ABSTRACT

This invention provides for a novel means of incorporating non-native amino acids into preselected positions of a protein using a cell-free synthesis system. The methods involve the use of non-orthogonal, native isoaccepting sense tRNAs that are encoded by the genetic code. Such methods allow for numerous non-native amino acids to be incorporated through the use of sense codons without having to rely upon orthogonal tRNA-synthetase pairs.

31 Claims, 29 Drawing Sheets

(56) References Cited

OTHER PUBLICATIONS

Tan et al.; "De novo genetic codes and pure translation display"; *Methods* 36:279-290 (2005).

Wang and Schultz, "Expanding the Genetic Code"; *Chem. Commun*.; 1:1-11 (2002).

Wang et al.; "Expanding the Genetic Code"; *Annu. Rev. Biophys. Biomol. Struct*., 35: 225-249 (2006).

Xie and Schultz, "Adding amino acids to the genetic repertoire"; *Curr. Opinion in Chemical Biology*, 9:548-554 (2005).

Xie and Schultz, "A Chemical Toolkit for Proteins—an expanded code"; *Nat. Rev. Mol. Cell Biol*.; 7: 775-782 (2006).

Xie and Schultz, "An expanding genetic code"; *Methods*, 36:227-238 (2005).

Supplementary European Search Report dated Jun. 22, 2012, issued in related European Patent Appln. No. 10729640.2.

Figure 1
A.
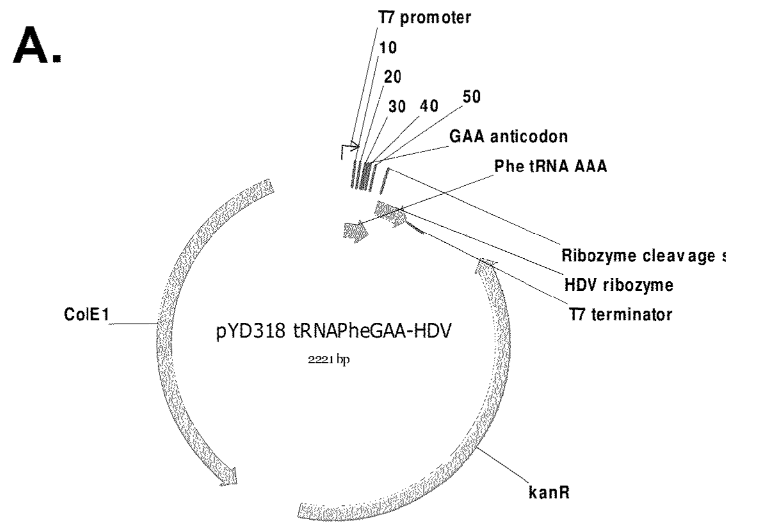
B.
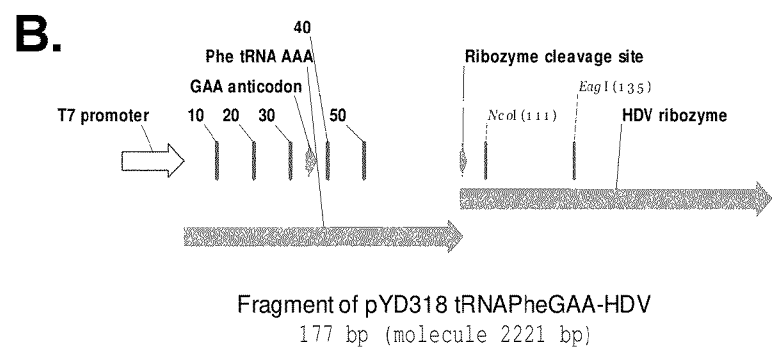
Fragment of pYD318 tRNAPheGAA-HDV
177 bp (molecule 2221 bp)
C.
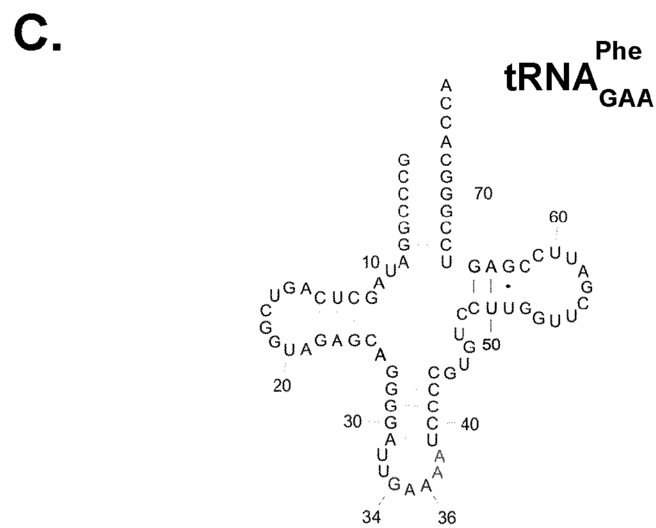

DNA
In vitro transcription (T7 RNAP/NTPS)
tRNA-ribozyme
Size Exclusion
Removal of 2,3 cyclic phosphate
$H_2O$
$P_i$
Polynucleotide kinase (PNK)
tRNA
nnAA
ATP
AMP
tRNA synthetase
tRNA synthetase charging with nnAA
tRNA-nnAA

Figure 6
A.
| | 1 | 2 |
|---|---|---|
| Inhibitor: | + | - |
-tRNA$^{Glu}$
B.
| | 1 | 2 | 3 | 4 | 5 |
|---|---|---|---|---|---|
| NTP | - | + | + | + | - |
| RNAse inhibitor | - | - | + | - | - |
| EDTA | - | - | - | + | + |
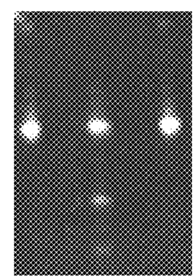
C.
| | 1 | 2 | 3 |
|---|---|---|---|
| DTT | - | + | + |
| EDTA | - | - | + |
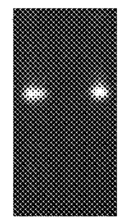

1.1.1

Figure 8
a
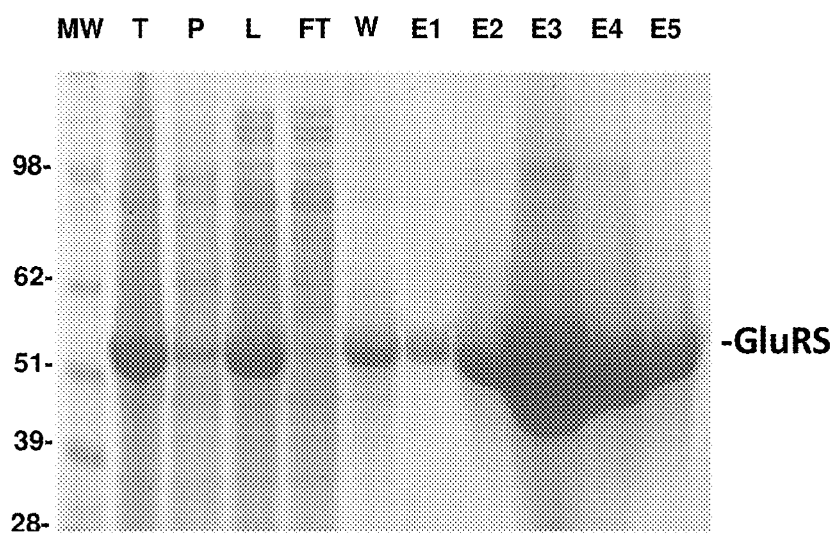
b
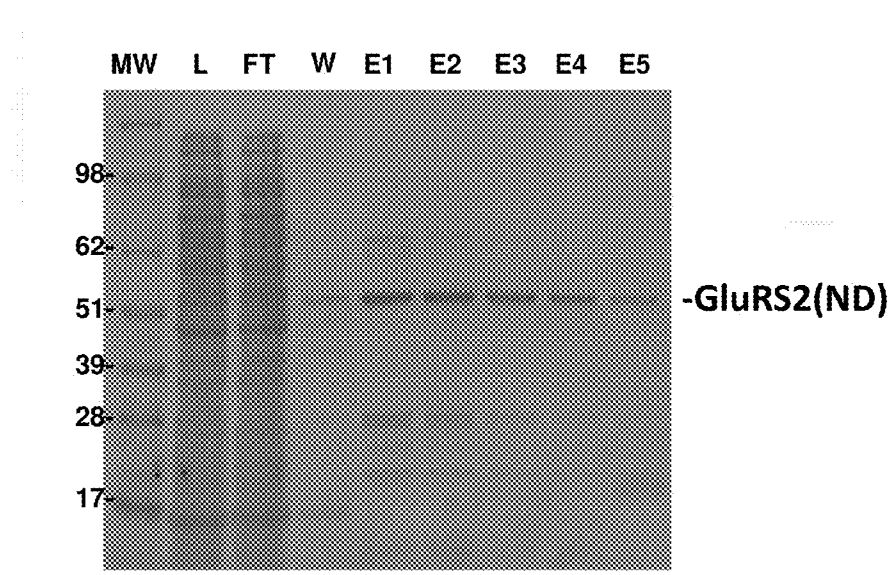

a
tRNA^Phe
Amino-
Acylation
site
PheS
Anticodon
Recognition
site
PheT
Thermus T. Phe RS
b
PheT +6XHisPheS (A294G)
PheRS
PheT domain
6XHisPheS domai Figure 10 Phe RS variants cell-free production and His tag purification

Figure 11
a.
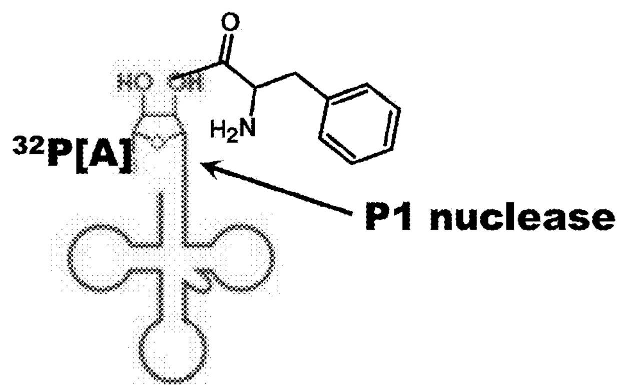
b.
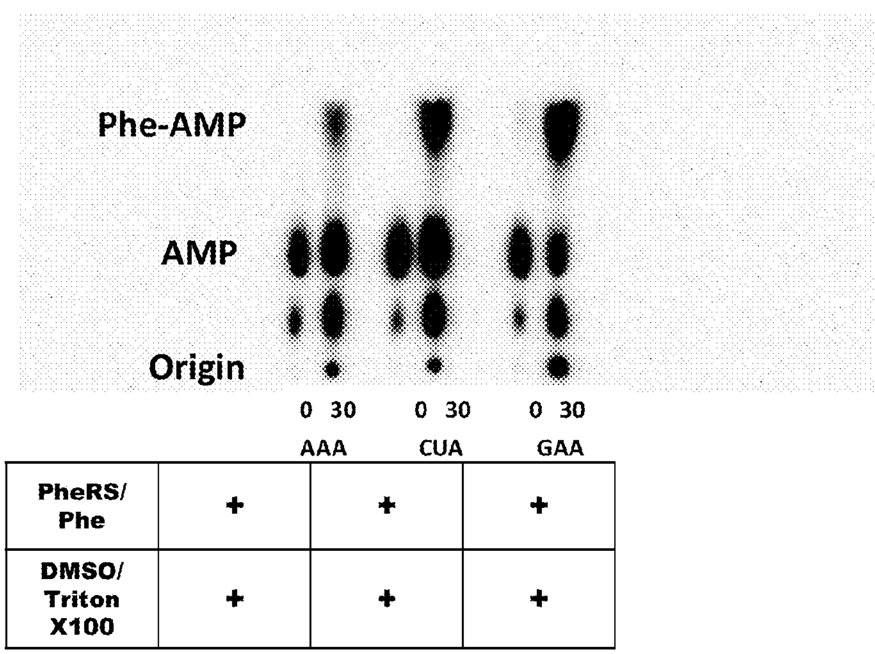

| PheRS(A294G) pAF | + | + | + | + | + | + |
|---|---|---|---|---|---|---|
| DMSO/ Triton X100 | - | - | - | + | + | + |

Figure 13
a.
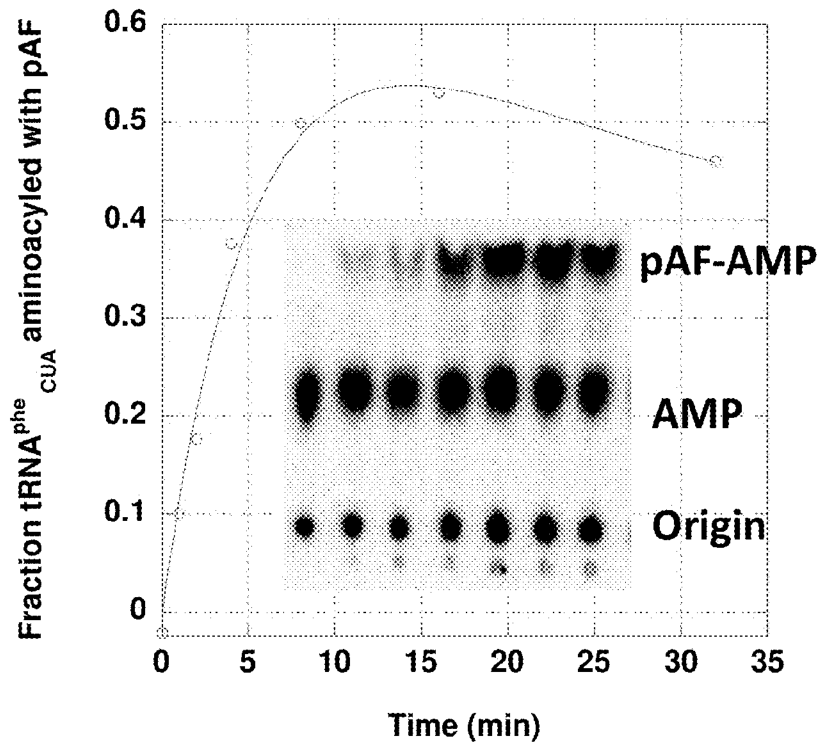
b.
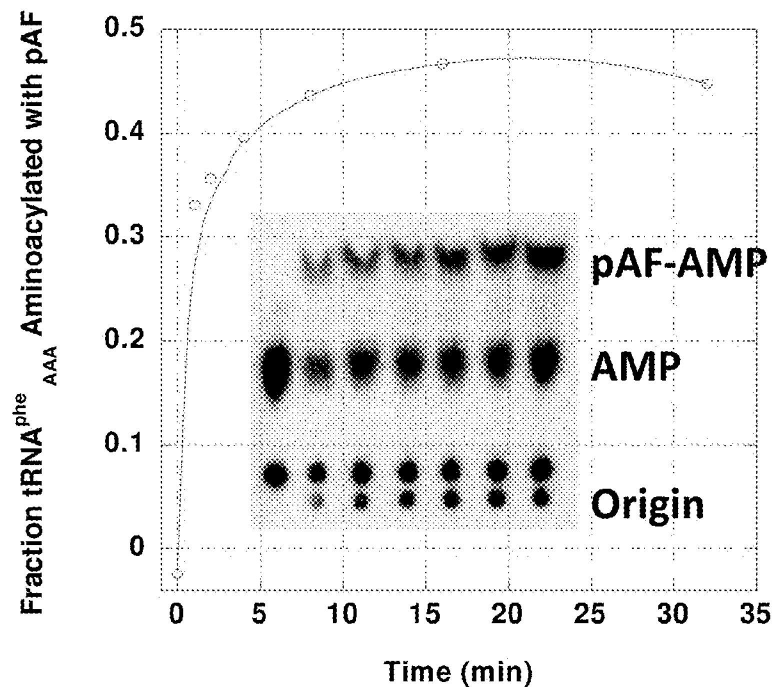

Figure 16 $tRNA^{phe}{}_{CUA}$
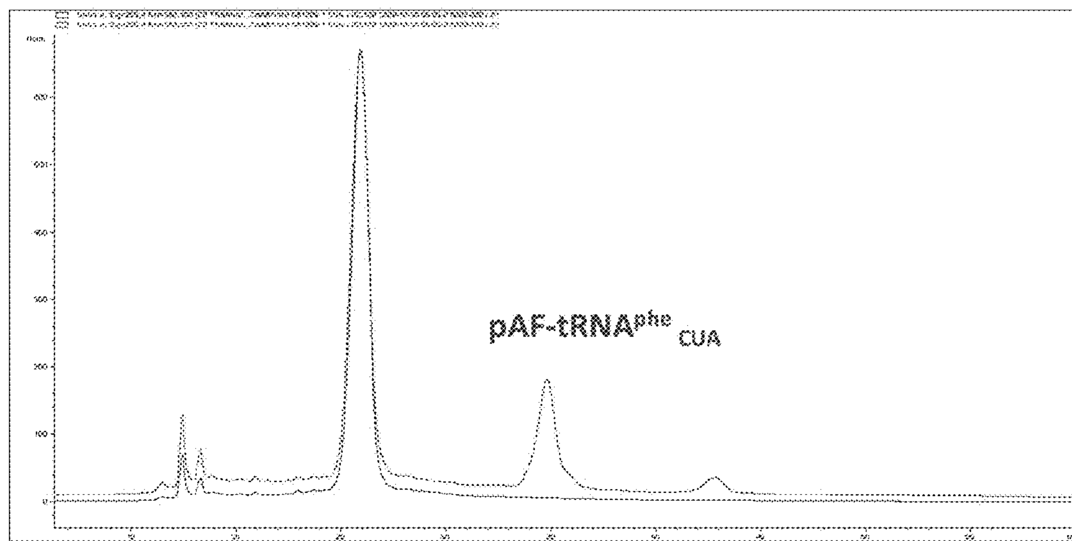
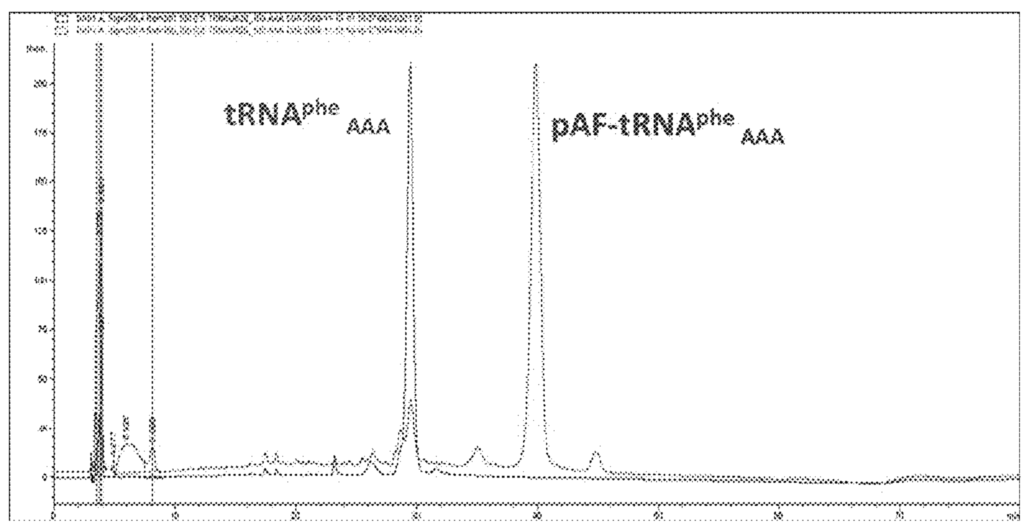

Figure 17
A. Wild type
$tRNA^{Glu}$
| | 1 | 2 | 3 | 4 | |
|---|---|---|---|---|---|
| GluRS enzyme | + | - | + | + | - |
| Amino acid | Glu | Glu | - | F-Glu | F-Glu |
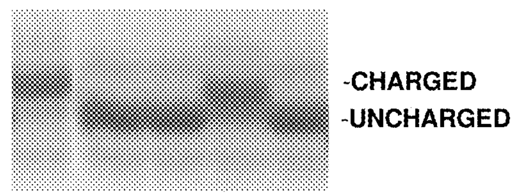
B. Wobble
$tRNA^{Glu}_{\underline{C}UC}$ U34C
| | 1 | 2 | 3 | 4 | 5 | 6 |
|---|---|---|---|---|---|---|
| GluRS enzyme | + | - | + | + | - | + |
| Amino acid | Glu | Glu | - | F-Glu | F-Glu | F-Glu |
| ATP | + | + | + | + | + | - |
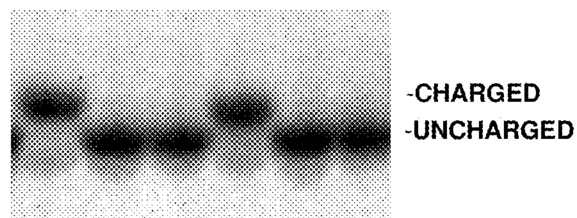

Figure 19 Tuning PheRS activity with an active-site directed inhibitor

Figure 22 TurboGFP Amber Suppressor Reporter
Y50(TAG) Y50F Y50L Y50
kDa
28
6
Full-length GFP
14C Autoradiography
Tyrosine hydroxyl is not buried, but aryl ring is buried
Y50
p-acetyl Phe
RFU
8000
7000
6000
5000
4000
3000
2000
1000
0
Phenylene Ring required for Fluorescence

Incorporation of Fluorescent nnAA

1. GM-CSF(AAA_111) plasmid 13 ug/mL
2. GM-CSF(AAA_111) plasmid 4 ug/mL
3. WT GM-CSF plasmid 13 ug/mL
4. No DNA template Ribosome
Ef-Tu
aatRNA
Isoaccepting
tRNAs
AAA or
CUA
aaRS
Amino
acids
eg
Arg
Phe
Gln
p-acetyl
Phe

MONO CHARGING SYSTEM FOR SELECTIVELY INTRODUCING NON-NATIVE AMINO ACIDS INTO PROTEINS USING AN IN VITRO PROTEIN SYNTHESIS SYSTEM

CROSS-REFERENCES TO RELATED APPLICATIONS

This application claims the benefit under 35 U.S.C. §1.119 (e) of U.S. Application Nos. 61/144,097, 61/144,083 and 61/144,030, all filed Jan. 12, 2009, each of which is incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Protein synthesis is a fundamental biological process that underlies the development of polypeptide therapeutics, vaccines, diagnostics, and industrial enzymes. With the advent of recombinant DNA (rDNA) technology, it has become possible to harness the catalytic machinery of the cell to produce a desired protein. This can be achieved within the cellular environment or in vitro using lysates derived from cells.

Because only twenty amino acids are naturally incorporated into proteins, limitations to the production of a desired protein exist. For example, a peptide that is potentially useful as a therapeutic agent may be quickly degraded or otherwise inactivated upon administration to a patient as a result of proteases present within the patient. Likewise, infectious agents such as bacteria or viruses are more likely to develop resistance against peptides that contain only naturally occurring amino acids. This occurs because enzymes that are produced by the bacteria or virus that can inactivate a peptide drug are more likely to inactivate a peptide containing naturally occurring amino acids as opposed to a peptide containing non-native amino acids. Such limitations become even more apparent when compared with small organic molecule synthesis, in which any structural change can be made to influence functional properties of the compound. As a result, proteins containing non-native amino acids are becoming more auspicious for therapeutic uses. Furthermore, peptides containing non-native amino acids are extremely useful for non-therapeutic research purposes, such as uses relevant to the structural and functional probing of proteins, construction of peptide libraries for combinatorial chemistry, and proteomic studies.

Although the twenty naturally occurring amino acids can be modified by post-translational modification, expanding the genetic code to include additional non-native amino acids with novel biological, chemical, or physical properties will increase the utility of the protein containing such novel non-native amino acids. Protein properties may include the size, acidity, nucleophilicity, hydrogen-bonding, or hydrophobicity of the protein.

Different strategies have been utilized to synthesize peptides containing non-native amino acids. Synthetic peptide chemistry has been used routinely for this purpose. See, e.g., Eckert et al., Cell 99:103-15 (1999). However, routine solid-phase peptide synthesis is generally limited to small peptides with less than 100 residues. With the recent development of enzymatic ligation and native chemical ligation of peptide fragments, it is possible to make larger proteins. However, these methods are not easily scaled. See, e.g., Dawson and Kent, Annu Rev. Biochem. 69:923 (2000).

In vivo translation using living cells is widely used for the efficient synthesis and post-translational modification of proteins from a genetically encoded natural or recombinant DNA sequence. However, folding may be inefficient if the protein is expressed in inclusion bodies. Most importantly, such methods are more difficult for the selective incorporation of multiple non-native amino acids, or to control the post-translational modification process.

In vitro, or cell-free, protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. For example, tRNA levels can be changed to reflect the codon usage of genes being expressed. The redox potential, pH, or ionic strength can also be altered with greater flexibility than with in vivo protein synthesis because concerns of cell growth or viability do not exist. Furthermore, direct recovery of purified, properly folded protein products can be easily achieved.

The productivity of cell-free systems has improved over 2-orders of magnitude in recent years, from about 5 μg/ml-hr to about 500 μg/ml-hr. Such improvements have made in vitro protein synthesis a practical technique for laboratory-scale research and provides a platform technology for high-throughput protein expression. It further indicates the feasibility for using cell-free technologies as an alternative means to in vivo large-scale, commercial production of protein pharmaceuticals.

The incorporation of non-native amino acids into proteins remains a challenge with both in vivo and in vitro protein synthesis systems. A major hurdle in this field of endeavor is promoting recognition of an aminoacyl-tRNA synthetase with a non-native amino acid. An aminoacyl-tRNA synthetase is an enzyme that catalyzes the bond of a specific amino acid to its cognate tRNA molecule. In most cases, each naturally occurring amino acid has one specific aminoacyl-tRNA synthetase that will aminoacylate that amino acid to its proper tRNA molecule, which is known as tRNA charging. There exists relatively few aminoacyl-tRNA synthetases considering the fact that the degeneracy of the genetic code allows amino acids to be charged to more than one kind of isoaccepting sense tRNA molecule. Thus, the success of incorporating non-native amino acids into proteins depends on the recognition of the non-native amino acid by aminoacyl-tRNA synthetases, which in general requires high selectively to insure the fidelity of protein translation. The fidelity of aminoacylation is maintained both at the level of substrate discrimination and proofreading of both non-cognate intermediates and protein products.

One strategy has been to incorporate non-native amino acids into proteins using aminoacyl-tRNA synthetases that cannot discriminate between non-native amino acids that are structurally similar to their natural counterparts due to lack of proofreading mechanisms. Because the proofreading activity of the aminoacyl-tRNA synthetase has been disabled, structural analogs of natural amino acids that have been misactivated may escape the editing functions of the synthetase, and be incorporated into the growing peptide chain as desired. See, e.g., Doring et al., Science 292:501 (2001).

A major limitation of the abovementioned strategy is that all sites corresponding to a particular natural amino acid throughout the protein are replaced. The extent of incorporation of the natural and non-native amino acid may also vary because it is difficult to completely deplete the cognate natural amino acid inside the cell. Another limitation is that these strategies make it difficult to study the mutant protein in living cells because the multisite incorporation of analogs often results in toxicity. Finally, this method is applicable in general only to close structural analogs of the common amino acids, again because substitutions must be tolerated at all sites in the genome.

More recently, orthogonal tRNAs and corresponding orthogonal aminoacyl-tRNA synthetases that charge the orthogonal tRNA with the desired non-native amino acid has been used as a strategy to overcome previous limitations. An orthogonal tRNA is a tRNA that base pairs with a codon that is not normally associated with an amino acid such as a stop codon or 4 base pair codon, etc. Importantly, orthogonal components do not cross-react with any of the endogenous tRNAs, aminoacyl-tRNA synthetases, amino acids, or codons in the host organism.

A commonly used orthogonal system for the incorporation of non-native amino acids is the amber suppressor orthogonal tRNA. Using this system, a suppressor tRNA is prepared that recognizes the stop codon UAG and is chemically aminoacylated with a non-native amino acid. Conventional site-directed mutagenesis is used to introduce the stop codon TAG at the site of interest in the protein gene. When the aminoacylated suppressor tRNA and the mutant gene are combined in an in vitro transcription/translation system, the non-native amino acid is incorporated in response to the UAG codon which gives a protein containing the non-native amino acid at the specified position. See, e.g., Sayers et al., Nucleic Acids Res. 16:791-802 (1988). Evidence has shown that the desired non-native amino acid is incorporated at the position specified by the UAG codon and that the non-native amino acid is not incorporated at any other site in the protein. See, e.g., Noren et al., Science 244:182-88 (1989); Ellman et al., Science 255: 197-200 (1992). For additional discussion of orthogonal translation systems that incorporate non-native amino acids, and methods for their production and use, see also Wang and Schultz, Chem. Commun. 1:1-11 (2002); Xie and Schultz, Methods 36:227-38 (2005); Xie and Schultz, Curr. Opinion in Chemical Biology 9:548-554 (2005); Wang et al., Annu Rev. Biophys. Biomol. Struct. 35:225-49 (2006); and Xie and Schultz, Nat. Rev. Mol. Cell. Biol. 7:775-82 (2006).

However, the incorporation of non-native amino acids using orthogonal components suffers from much lower yields because it relies on inherently inefficient suppressor tRNAs competing with termination factors. In addition, the use of orthogonal components for incorporation of non-native amino acids has been restricted to selective incorporation of only a single non-native amino acid per protein at only one of the three nonsense termination codons (the UAG amber stop codon) because of competition at amino acid sense codons from natural amino acids catalyzed by the tRNA charging and proofreading activities of the twenty different aminoacyl-tRNA synthetases, and because attempts to use a second termination codon (UGA) often fails due to read-through by the ribosome. See, e.g., Cload et al., Chem. and Biol. 3:1033-38 (1996).

While some attempts have been made to incorporate non-native amino acids into proteins using tRNAs that recognize sense codons, such attempts have been made using a pure reconstituted in vitro translation system. See Tan et al., Methods 36:279-90 (2005); Forster et al., U.S. Pat. No. 6,977,150. However, such pure reconstituted translation systems require purified translational components, which is impractical outside of the context of research, very expensive, and not shown to be highly efficient.

There exists a need in the art for incorporating non-native amino acids into a growing polypeptide chain, where orthogonal tRNA/aminoacyl-tRNA synthetase pairs can be avoided, where native isoaccepting tRNAs aminoacylated with non-native amino acids recognize sense codons and subsequently incorporate the non-native amino acid into a growing polypeptide chain at a position defined by the sense codon, where numerous non-native amino acids can be incorporated at defined positions, and where a crude cell-free protein synthesis system can be used that avoids the impracticality, expense, and inefficiency of a pure reconstituted in vitro translation system. The invention described herein fulfills these and other needs, as will be apparent upon review of the following disclosure.

BRIEF SUMMARY OF THE INVENTION

This invention discloses a method for introducing non-native amino acids into pre-selected positions of a protein using a cell-free synthesis system comprising the steps of 1) obtaining a nucleic acid template comprising degenerate sense codons, 2) lysing a cell population to yield a cell lysate that is depleted of a native aminoacyl-tRNA synthetase, 3) adding an exogenous aminoacyl-tRNA synthetase that selectively aminoacylates a first isoaccepting sense tRNA to the lysate, 4) aminoacylating a second isoaccepting sense tRNA in a separate tRNA charging reaction, said second isoaccepting sense tRNA charged with a non-native amino acid, 5) adding the second isoaccepting sense tRNA charged with its respective non-native amino acids and the nucleic acid template to the cell lysate and permitting the reaction to generate a protein bearing non-native amino acids in positions corresponding to the second sense codons of the template.

More specifically, this invention is an in vitro method of introducing non-native amino acids into pre-selected positions of a protein using a cell-free synthesis system, the method comprising the steps of:

a) Obtaining a nucleic acid template comprising degenerate sense codons where a first sense codon and a second sense codon correspond to the same native amino acid but differ in their respective nucleotide sequence;

b) Lysing a cell population to yield a cell lysate where said lysate is depleted of the native aminoacyl-tRNA synthetase that aminoacylates said native amino acid;

c) Adding to the lysate a first exogenous aminoacyl-tRNA synthetase that selectively aminoacylates a first isoaccepting sense tRNA corresponding to the first sense codon of the nucleic acid template;

d) Adding a catalytic aminoacylating agent to a reaction vessel containing a charging reaction mixture including a non-native amino acid and a second isoaccepting sense tRNA corresponding to the second sense codon of the nucleic acid template;

e) Aminoacylating the second isoaccepting sense tRNA with the non-native amino acid to yield a tRNA:non-native amino acid charged moiety;

f) combining the cell lysate of step 2 with:

1) the tRNA:non-native amino acid charged moiety; and, 2) a nucleic acid template comprising the first and second sense codons under conditions appropriate to generate a protein from the template; and, g) permitting the reaction to generate the protein bearing non-native amino acids in those positions corresponding to the second sense codons of the nucleic acid template.

The above described method is optionally performed wherein the native aminoacyl-tRNA synthetase by altering the cell population prior to lysing where the alteration replaces the gene encoding the native aminoacyl-tRNA synthetase with a gene encoding the native aminoacyl-tRNA synthetase fused to a capture moiety. This method can be performed with a native aminoacyl-tRNA synthetase tagged with a capture moiety where the synthetase is heterologous to the cells forming the cell lysate. The tagged native aminoacyl-tRNA synthetase can be removed by affinity chromatography, immunoaffinity chromatography, or immunoprecipitation. The native aminoacyl-tRNA synthetase can optionally be removed by immunoprecipitation without being tagged with a capture moiety. The tRNA charging reaction that aminoacylates the second isoaccepting sense tRNA molecule can utilize either an aminoacyl-tRNA synthetase or a ribozyme as the catalytic aminoacylating agent. The first exogenous aminoacyl-tRNA synthetase may either be synthesized and added to the lysate mixture, or be added as a result of transforming the cells prior to lysing with a gene encoding the first exogenous aminoacyl-tRNA synthetase.

In a related method this invention is practiced by:

a) depleting the cell lysate of the native aminoacyl-tRNA synthetase by altering the cells used to generate the cell lysate to inhibit expression of the native aminoacyl-tRNA synthetase;

b) transforming said cells with a first and second gene wherein said first gene expresses the first exogenous aminoacyl-tRNA synthetase and said second gene expresses a second exogenous aminoacyl-tRNA synthetase that selectively aminoacylates the second isoaccepting sense tRNA; and c) depleting the cell lysate of the second exogenous aminoacyl-tRNA synthetase.

The method described above is preferred to be practiced using first and second aminoacyl-tRNA synthetases from *A. ferrooxidans*. The above describe method may be practiced wherein the native aminoacyl-tRNA synthetase is depleted by mutating said native aminoacyl-tRNA synthetase gene. The second exogenous aminoacyl-tRNA synthetase is optionally performed by fusing said synthetase to a capture moiety and depleting said synthetase by affinity chromatography, immunoaffinity chromatography, or immunoprecipitation. The second exogenous aminoacyl-tRNA synthetase may be depleted by immunoprecipitation using an antibody that recognizes said exogenous aminoacyl-tRNA synthetase.

The methods can be practiced using a cell lysate that is from bacteria, preferably from *E. coli*. The cell population may consist of rabbit reticulocytes. Additionally, the methods described may take place in cells depleted of arginine decarboxylase.

This invention further provides a cell-free synthesis lysate for in vitro protein synthesis comprising an exogenous aminoacyl-tRNA synthetase that selectively aminoacylates only a single isoaccepting sense tRNA corresponding to an amino acid and is depleted for the native aminoacyl-tRNA synthetase corresponding to said amino acid. This lysate may be from a bacterial cell, preferably from *E. coli*. The lysate described above may be from rabbit reticulocytes. The above-described lysate may optionally be free of arginine decarboxylase, exhibit a functional oxidative phosphorylation system, contain an antifoam agent, or contain a nucleic acid template encoding a protein and comprising degenerate sense codons for the amino acid.

This invention further discloses a method for introducing non-native amino acids into pre-selected positions of a protein using a cell-free synthesis system comprising the steps of 1) obtaining a nucleic acid template comprising degenerate sense codons, 2) lysing a cell population to yield a cell lysate, 3) inactivating an isoaccepting tRNA that recognizes the second sense codon, 4) aminoacylating a second isoaccepting sense tRNA in a separate tRNA charging reaction, said second isoaccepting sense tRNA charged with a non-native amino acid, 5) adding the second isoaccepting sense tRNA charged with its respective non-native amino acids and the nucleic acid template to the cell lysate and permitting the reaction to generate a protein bearing non-native amino acids in positions corresponding to the second sense codons of the template.

More specifically, the invention further discloses:

a) Obtaining a nucleic acid template comprising degenerate sense codons where a first sense codon and a second sense codon correspond to a same native amino acid but differ in their respective nucleotide sequence;

b) Generating a cell lysate that contains a native aminoacyl-tRNA synthetase, said synthetase having the ability to aminoacylate both a first isoaccepting sense tRNA corresponding to the first sense codon of the nucleic acid template and a second isoaccepting sense tRNA corresponding to the second sense codon of the nucleic acid template;

c) Inactivating the native second isoaccepting sense tRNA corresponding to the second sense codon of the nucleic acid template;

d) Adding a catalytic aminoacylating agent to a reaction vessel containing a charging reaction mixture including a non-native amino acid and a second isoaccepting sense tRNA corresponding to the second sense codon of the nucleic acid template;

e) Aminoacylating the second isoaccepting sense tRNA with the non-native amino acid to yield a tRNA:non-native amino acid charged moiety;

f) Combining the cell lysate with:

1) the tRNA:non-native amino acid charged moiety; and, 2) a nucleic acid template comprising the first and second sense codons under conditions appropriate to generate a protein from the template; and, g) Permitting the reaction to generate the polypeptide bearing non-native amino acids in those positions corresponding to the second sense codons of the nucleic acid template.

In one embodiment where the second isoaccepting tRNA is inactivated, said inactivation is practiced by adding anti-sense DNA that selectively binds to the native second isoaccepting sense tRNA. In some embodiments, the second isoaccepting sense tRNA is inactivated by adding a specific tRNA ribonuclease or active fragments thereof that selectively cleave the native second isoaccepting sense tRNA. In some embodiments, the second isoaccepting sense tRNA is inactivated by adding colicin D or an active fragment of colicin D.

This invention further provides a charged tRNA solution comprising a bacterial cell lysate having charged tRNAs bearing pre-selected amino acids, recognizing sense codons and having no significant synthetase activity for the charged tRNA bearing the pre-selected amino acids, and the charged tRNA solution is free of specific or non-specific synthetase inhibitors.

BRIEF DESCRIPTION OF THE DRAWINGS

FIG. 1 shows (a) the tRNA$_{GAA}^{Phe}$ HDV ribozyme plasmid DNA template used for in vitro transcription, (b) a fragment of the DNA template detailing the orientation of the T7 promotor, tRNA$_{GAA}^{Phe}$ coding sequence fused to the hepatitis delta virus (HDV) ribozyme sequence, and (c) the resulting *E. coli* isoaccepting tRNA$_{GAA}^{Phe}$ transcript (SEQ ID NO:6) secondary structure with the anticodon sequence GAA in red, where the subscript denotes the corresponding anticodon sequence.

FIG. 6 shows the effect of various additives on RNA stability.

FIG. 8 shows IMAC purification profiles of (a) *E. coli* GluRS 6×His and (b) *H. pylori* GluRS2 (ND) enzymes used for charging tRNA with non-native amino acids (nnAA).

FIG. 11 shows percent Phe aminoacylation analysis of [$^{30-32}$] Phe-tRNA$^{Phe}$ catalyzed by PheRS(A294G) for 30 min. (a) P1 nuclease digestion of (b) Phe-tRNA$_{AAA}^{Phe}$, Phe-tRNA$_{CUA}^{Phe}$, or Phe-tRNA$_{GAA}^{Phe}$ results in [$^{32}$P]Phe-AMP that can be separated from free [$^{32}$P]AMP on PEI cellulose TLC plates and imaged using autoradiography.

FIG. 13 shows the time dependence of the formation of (a) pAF-tRNA$_{CUA}^{Phe}$ and (b) pAF-tRNA$_{AAA}^{Phe}$ as measured by autoradiography.

FIG. 16 shows (a) the separation of aminoacylated pAF-tRNA$_{CUA}^{Phe}$ from tRNA$_{CUA}^{Phe}$ and (b) pAF-tRNA$_{AAA}^{Phe}$ from tRNA$_{AAA}^{Phe}$ using hydrophobic interaction chromatography.

FIG. 17 shows that (a) Wild type *E. coli* tRNA$^{Glu}$ and (b) in vitro transcribed *E. coli* tRNA$_{CUC}^{Glu}$ can be robustly charged with mono-fluoroglutamate as determined by acid/urea gel electrophoresis.

DETAILED DESCRIPTION OF THE INVENTION

I. Introduction

Figure 2:
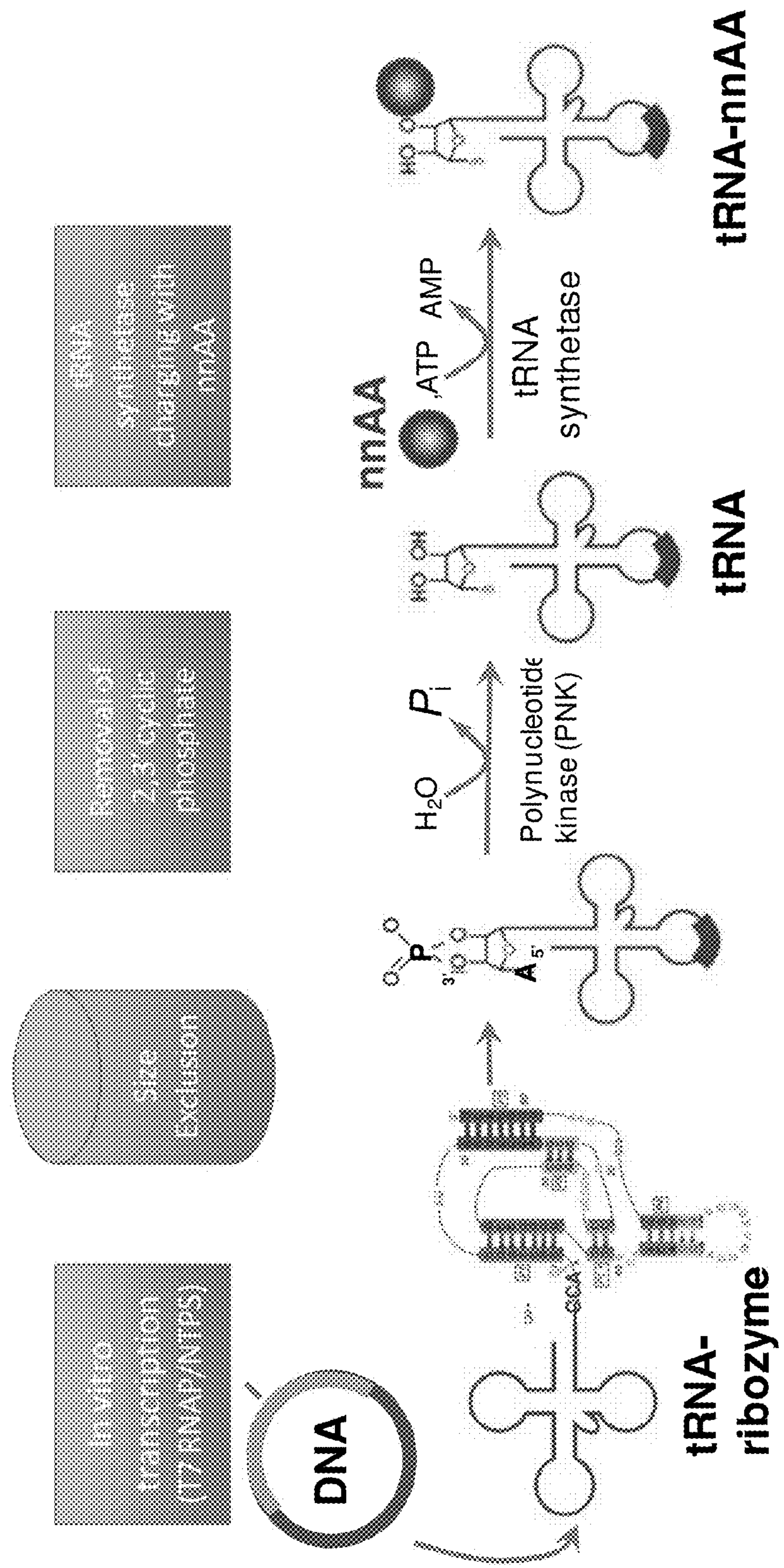
FIG. 2 shows the process flow diagram illustrating the steps required to generate novel nnAA-tRNAs including (a) in vitro transcription of tRNA-HDV ribozyme DNA template (partial sequence=SEQ ID NO:7) (b) isolation of tRNA 2,3'-cyclic phosphate by size exclusion chromatography, (c) enzymatic hydrolysis of tRNA 2,3'-cyclic phosphate using T4 polynucleotide kinase (PNK) and, (d) aminoacylation of engineered isoaccepting tRNAs with nnAAs catalyzed by engineered amino acid tRNA synthetase (aaRS) enzymes.

This invention provides for a novel means of incorporating non-native amino acids into preselected positions of a protein using a cell-free synthesis system. The methods involve the use of non-orthogonal, native isoaccepting sense tRNAs that are encoded by the genetic code. Such methods allow for numerous non-native amino acids to be incorporated through the use of sense codons without having to rely upon orthogonal aminoacyl-tRNA synthetases.

Important to the present invention is the utilization of isoaccepting sense tRNAs to differentially incorporate either native or non-native amino acids into a protein even though such tRNAs are normally charged with the same amino acid in nature. This invention exploits the degeneracy of the genetic code to incorporate non-native amino acids into a growing polypeptide chain based on an mRNA sense codon sequence without compromising the ability to incorporative the native amino acid into the protein. Following cell lysis, a lysate is created that contains all the cellular components required for protein synthesis. A nucleic acid template is then added that has sense codons specifying positions in which the non-native amino acid will be incorporated. Because native aminoacyl-tRNA synthetases generally have the ability to charge both isoaccepting sense tRNAs, in some embodiments, the native aminoacyl-tRNA synthetase of interest is depleted from the lysate prior to the protein synthesis reaction to prevent uncharged isoaccepting sense tRNA molecules from being charged with the non-desired amino acids. A first isoaccepting sense tRNA to be charged with the native amino acid is charged directly in the lysate. This requires the addition of a first exogenous aminoacyl-tRNA synthetase to the lysate that selectively charges only the first isoaccepting sense tRNA in those embodiments where the native aminoacyl-tRNA synthetase is depleted. The first exogenous aminoacyl-tRNA synthetase may either be expressed in the host cell population prior to cell lysis, or added directly to the lysate following cell lysis. In other embodiments, the native aminoacyl-tRNA synthetase is not depleted. Instead, the second isoaccepting tRNA is inactivated, and the native aminoacyl-tRNA synthetase is left simply to charge the first isoaccepting tRNA.

The second isoaccepting tRNA is charged with a non-native amino acid is aminoacylated in a separate tRNA charging reaction. This aspect of the invention is termed "mono charging" because only the non-native amino acid is charged to one isoaccepting sense tRNA in a reaction separate from the protein synthesis reaction. Any method that will aminoacylate a tRNA molecule is sufficient regardless of whether an aminoacyl-tRNA synthetase is utilized for the separate charging reaction. For example, either a purified ribozyme or any functional aminoacyl-tRNA synthetase may be used to separately charge the second isoaccepting sense tRNA molecule. The second isoaccepting sense tRNA that is charged with a non-native amino acids is then purified from the charging reaction mixture, which include isolation from any aminoacyl-tRNA synthetases that would be used in the reaction vessel. The purified isoaccepting sense tRNA molecules aminoacylated with a non-native amino acid is then added to the lysate in which the protein synthesis reaction will occur to generate a desired protein containing both native and non-native amino acids in positions specified by the different sequences recognized by isoaccepting sense tRNAs.

The uses of proteins containing non-native amino acids include desired changes in protein structure and/or function, which would include changing the size, acidity, nucleophilicity, hydrogen bonding, hydrophobicity, or accessibility of protease target sites. Proteins that include an non-native amino acid can have enhanced or even entirely new catalytic or physical properties such as modified toxicity, biodistribution, structural properties, spectroscopic properties, chemical and/or photochemical properties, catalytic ability, serum half-life, and the ability to react with other molecules, either covalently or noncovalently. Proteins that include at least one non-native amino acid are useful for, but not limited to, novel therapeutics, diagnostics, catalytic enzymes, binding proteins, and the study of protein structure and function.

The cell-free non-native amino acid incorporation method of this invention is distinct from the non-native amino acid incorporation methods previously employed in the art. Most notably, this invention uses isoaccepting tRNAs that recognize sense codons, which circumvents the requirement of having to utilize orthogonal tRNAs and orthogonal aminoacyl-tRNA synthetases in order to incorporate non-native amino acids. Using orthogonal tRNAs relies on inherently inefficient suppressor tRNAs. This inefficiency is a result competition at the non-orthogonal sense codons from natural amino acids catalyzed by the tRNA charging and proofreading activities of the twenty different aminoacyl-tRNA synthetases in addition to inherently inefficient suppressor tRNAs competing with termination factors. This results in selective incorporation of only a single non-native amino acid per protein at only one of the three termination codons: the UAG "amber" codon. Additionally, orthogonal protein synthesis systems that utilize amber stop codons to incorporate non-native amino acids often fail to terminate at the second termination codon due to read through by the ribosome. See, e.g., Cloud et al., Chem. and Biol. 3:1033-38 (1996). Although attempts have been made to utilize sense codon recognition for incorporation of non-native amino acids (see e.g. Tan et al., Methods 36:279-90 (2005); Forster et al., U.S. Pat. No. 6,977,150), such pure reconstituted translation systems require purified translational components, which is impractical outside of the context of research, very expensive, and not shown to be highly efficient.

The protein synthesis reaction is practiced by obtaining a nucleic acid encoding the desired protein as described above, obtaining a lysate as described above that lacks a native aminoacyl-tRNA synthetase but contains an aminoacyl-tRNA synthetase capable of charging an isoaccepting sense tRNA and allowing that isoaccepting sense tRNA to be charged with a native amino acid directly in the lysate, obtaining another isoaccepting sense tRNA that has been charged with a non-native amino acid in a separate tRNA charging reaction, and combining the nucleic acid and isoaccepting sense tRNA charged with the non-native amino acid with the cellular lysate to form a protein synthesis reaction mixture.

The modified protein may also be referred to as the desired protein, selected protein, or target protein. As used herein, the modified protein refers generally to any peptide or protein having more than about 5 amino acids. The modified protein comprises at least one non-native amino acid at a pre-determined site, and may contain multiple non-native amino acids. If present at two or more sites in the polypeptide, the non-native amino acids can be the same or different. Where the non-native amino acids are different, the tRNA codons for each non-native amino acids will also be different.

The modified protein may be homologous to, or may be exogenous, meaning that they are heterologous, i.e., foreign, to the cells from which the cell-free lysate is derived, such as a human protein, viral protein, yeast protein, etc. produced in a bacterial cell-free extract. Modified proteins may include, but are not limited to, molecules such as, e.g., renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-(3; platelet-derived growth factor (PDGF); fibroblast growth factor such as aFGF and bFGF; epidermal growth factor (EOF); transforming growth factor (TGF) such as TGF-alpha and TGF-beta, including TGF-(31, TGF-(32, TGF-(33, TGF-(34, or TGF-(35; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-I 9; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

II. Definitions

"Aminoacylation" or "aminoacylate" refers to the complete process in which a tRNA is "charged" with its correct amino acid that is a result of adding an aminoacyl group to a compound. As it pertains to this invention, a tRNA that undergoes aminoacylation or has been aminoacylated is one that has been charged with an amino acid, and an amino acid that undergoes aminoacylation or has been aminoacylated is one that has been charged to a tRNA molecule.

"Aminoacyl-tRNA synthetase" or "tRNA synthetase" or "synthetase" or "aaRS" or "RS" refers to an enzyme that catalyzes a covalent linkage between an amino acid and a tRNA molecule. This results in a "charged" or "aminoacylated" tRNA molecule, which is a tRNA molecule that has its respective amino acid attached via an ester bond.

"Binding moiety" refers to a tag that genetically engineered onto a protein. Such tags may include, but are not limited to a His-tag, GFP-tag, GST-tag, FLAG-tag, etc.

"Capture moiety" refers to any substrate or ligand that is part of a molecular association responsible for eliminating an unwanted aminoacyl-tRNA synthetase from a reaction mixture. Such ligand or substrate moieties may include, but are not limited to, antibodies, affinity supports, matrices, resins, columns, coated beads.

"Catalytic aminoacylating reagent" refers to any enzyme or molecule that has the capability to charge a tRNA molecule. Such aminoacylating reagents may refer to, but are not limited to, aminoacyl-tRNA synthetases or ribozyme columns.

"Cell-free synthesis system" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with unnatural amino acids, polymerases, transcriptional factors, etc.

"Charged tRNA" or "aminoacylated tRNA" refers to a tRNA molecule that has an amino acid bound at the amino acid attachment site. During protein synthesis, the amino acid to transferred to the growing polypeptide chain, releasing the tRNA, which is referred to as the "released tRNA."

"Charging reaction mixture" refers to an in vitro reaction mixture in which an isoaccepting sense tRNA is charged with its respective amino acid. The mixture contains isoaccepting tRNAs with a specific codon sequence that is to be charged. Methods for charging natural, non-native and/or arbitrary tRNA with natural, non-native and/or arbitrary amino acids are known in the art, and include, but are not limited to, chemical aminoacylation, biological misacylation, acylation by modified aminoacyl tRNA synthetases, ribozyme-based, and protein nucleic acid-mediated methods.

"Degenerate codon" refers to the degeneracy of the genetic code such that one amino acid may be coded for by more than one codon. A codon is a three nucleotide sequence specifying that amino acid. Degeneracy is a result of all proteins being made up of only 20 amino acids even though 64 possible codons exist.

"DNA" refers to a sequence of two or more covalently bonded, naturally occurring or modified deoxyribonucleotides.

"Exogenous aminoacyl-tRNA synthetase" refers to any aminoacyl-tRNA synthetase that is not endogenously produced by a cell from which the cell lysate is produced. As it pertains to this invention, an exogenous aminoacyl-tRNA synthetase may be expressed within a host cell. If the exogenous synthetase is expressed within a host cell, the exogenous synthetase may either function in tandem with the endogenous aminoacyl-tRNA synthetase, or functionally replace the endogenous aminoacyl-tRNA synthetase if the endogenous aminoacyl-tRNA synthetase is to be rendered non-functional by any of the methods described herein. Additionally, an exogenous aminoacyl-tRNA synthetase may be expressed and purified and subsequently added to either a tRNA charging or cell-free protein synthesis reaction. An exogenous aminoacyl-tRNA synthetase may be purified from either the host cell in which the protein synthesis extract is derived from, or any other cell capable of expressing such synthetase. Exogenous aminoacyl-tRNA synthetases may be recombinant native aminoacyl-tRNA synthetases, or recombinant non-native aminoacyl-tRNA synthetases.

"Gene" refers to a hereditary unit consisting of a sequence of DNA that has a specific chromosomal location. A gene is expressed to produce a protein product.

"Heterologous" as it pertains to this invention refers to an aminoacyl-tRNA synthetase that originates from a species different from the host cell in which it is expressed.

"Isoaccepting sense tRNA" refers to different tRNA species that bind to alternate codons for the same amino acid.

"Lysate" is any cell derived preparation comprising the components required for protein synthesis machinery, wherein such cellular components are capable of expressing a nucleic acid encoding a desired protein where a majority of the biological components are present in concentrations resulting from the lysis of the cells rather than having been reconstituted. A lysate may be further altered such that the lysate is supplemented with additional cellular components, e.g. amino acids, nucleic acids, enzymes, etc. The lysate may also be altered such that additional cellular components are removed following lysis.

"Native amino acid" refers to one or more naturally occurring amino acids encoded by the genetic code. An "endogenous native amino acid" refers to a native amino acid produced by the host cells used to generate the lysate.

"Native aminoacyl-tRNA synthetase" refers to a host cell aminoacyl-tRNA synthetase enzyme that is found in nature. Native aminoacyl-tRNA synthetases may be synthesized and added exogenously to a lysate or tRNA reaction vessel as defined by this invention. Native aminoacyl tRNA synthetases include, but are not limited to, a natural aminoacyl tRNA synthetases from one or more of plants, microorganisms, prokaryotes, eukaryotes, protozoa, bacteria, mammals, yeast, *E. coli*, or humans.

"Native isoaccepting sense tRNA" refers to either a first or second isoaccepting sense tRNA that is produced by the host population of cells used to create the lysate used for the cell-free protein synthesis reaction.

"Non-native amino acids" or "nnAA" refer to amino acids that are not one of the twenty naturally occurring amino acids that are the building blocks for all proteins that are nonetheless capable of being biologically engineered such that they are incorporated into proteins. Non-native amino acids may include D-peptide enantiomers or any post-translational modifications of one of the twenty naturally occurring amino acids. A wide variety of non-native amino acids can be used in the methods of the invention. The non-native amino acid can be chosen based on desired characteristics of the non-native amino acid, e.g., function of the non-native amino acid, such as modifying protein biological properties such as toxicity, biodistribution, or half life, structural properties, spectroscopic properties, chemical and/or photochemical properties, catalytic properties, ability to react with other molecules (either covalently or noncovalently), or the like. Non-native amino acids that can be used in the methods of the invention may include, but are not limited to, an non-native analogue of a tyrosine amino acid; an non-native analog of a glutamine amino acid; an non-native analog of a phenylalanine amino acid; an non-native analog of a serine amino acid; an non-native analog of a threonine amino acid; an alkyl, aryl, acyl, azido, cyano, halo, hydrazine, hydrazide, hydroxyl, alkenyl, alkynl, ether, thiol, sulfonly, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analog containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid, e.g., a sugar substituted serine or the like; a carbon-linked sugar-containing amino acid; a redox-active amino acid; an $\alpha$-hydroxy containing acid; an amino thio acid containing amino acid; an $\alpha,\alpha$ disubstituted amino acid; a $\beta$-amino acid; a cyclic amino acid other than praline, etc.

"Polypeptide" or "peptide" or "protein" refers to two or more naturally occurring amino acids, joined by one or more peptide bonds.

"Reaction vessel" refers to the containment in which the tRNA charging reaction occurs.

"Ribozyme" refers an RNA molecule that is capable of catalyzing a chemical reaction. As it pertains to the current invention, a ribozyme has aminoacylating activity such that it will charge a tRNA molecule independent of an aminoacyl-tRNA synthetase.

"RNA" refers to a sequence of two or more covalently bonded, naturally occurring or modified ribonucleotides.

"Sense codon" refers to a set of three nucleotides in a protein coding sequence that specify an amino acid. As used in this invention, a sense codon does not include a termination signal or stop codon.

"tRNA" or "transfer RNA" refers to a small RNA molecule that transfers a specific amino acid to a growing polypeptide chain at the ribosomal site of protein synthesis during translation. tRNAs contain a three base codon that pairs to the corresponding mRNA codon. As a result of the degeneracy of the genetic code, an amino acid can associate with multiple tRNAs, while each type of tRNA molecule can only associate with one type of amino acid.

"tRNA charging reaction" refers to the reaction in which a synthesized native tRNA is charged with its respective amino acid separate from the protein synthesis reaction, whether said amino acid is natural or non-native.

"tRNA:non-native amino acid charged moiety" refers generally to a tRNA molecule that is an isoaccepting tRNA molecule to the isoaccepting first tRNA molecule, but which has been charged with a non-native amino acid in place of the native amino acid.

"Transforming" a cell or population of cells refers to the alteration of the gene expression of a host cell or cells from which the lysate is derived. As used in this invention, transforming a cell refers to the process in which is cell is altered such that an exogenous nucleic acid sequence is introduced that expresses a recombinant protein.

III. Template

In order to produce the proteins of this invention, one needs a nucleic acid template. The template for cell-free protein synthesis can be either mRNA or DNA. The template can encode for any particular gene of interest, and may encode a full-length polypeptide or a fragment of any length thereof. Nucleic acids to serve as sequencing templates are optionally derived from a natural source or they can be synthetic or recombinant. For example, DNAs can be recombinant DNAs, e.g., plasmids, viruses or the like. The nature of the invention uses sense codons for the incorporation of non-native amino acids, and circumvents the requirement of orthogonal components as is commonly found in the art. As a result, a preferred embodiment of the invention will use a template that is capable of translating a complete and functional protein regardless of whether non-native amino acids are chosen to be incorporated.

A DNA template that comprises the gene of interest will be operably linked to at least one promoter and to one or more other regulatory sequences including without limitation repressors, activators, transcription and translation enhancers, DNA-binding proteins, etc. Suitable quantities of DNA template for use herein can be produced by amplifying the DNA in well known cloning vectors and hosts, or by polymerase chain reaction (PCR).

A preferred embodiment uses a bacterial lysate. A DNA template be constructed for bacterial expression by operably linking a desired protein-encoding DNA to both a promoter sequence and a bacterial ribosome binding site (Shine-Delgarno sequence). Promoters suitable for use with the DNA template in the cell-free transcription-translation methods of the invention include any DNA sequence capable of promoting transcription in vivo in the bacteria from which the bacterial extract is derived. Preferred are promoters that are capable of efficient initiation of transcription within the host cell. DNA encoding the desired protein and DNA containing the desired promoter and Shine-Dalgarno (SD) sequences can be prepared by a variety of methods known in the art. Alternatively, the desired DNA sequences can be obtained from existing clones or, if none are available, by screening DNA libraries and constructing the desired DNA sequences from the library clones.

RNA templates encoding the protein of interest can be conveniently produced from a recombinant host cell transformed with a vector constructed to express a mRNA with a bacterial ribosome binding site (SD sequence) operably linked to the coding sequence of the desired gene such that the ribosomes in the reaction mixture are capable of binding to and translating such mRNA. Thus, the vector carries any promoter capable of promoting the transcription of DNA in the particular host cell used for RNA template synthesis.

Because it is difficult to extract undegraded RNA from bacteria, higher eukaryotic cell culture is preferred for the production of the RNA template. In principle, any higher eukaryotic cell culture is workable, including both vertebrate and invertebrate cell cultures. The RNA template can be conveniently isolated in a total cellular RNA fraction extracted from the host cell culture. Total cellular RNA can be isolated from the host cell culture by any method known in the art. The desired RNA template can be isolated along with most of the cellular mRNA if the RNA template is designed to contain at its 3' end a polyadenylation signal recognized by the eukaryotic host cell. Thus, the host cell will produce the RNA template with a polyadenylate (poly(A)) tail. Polyadenylated mRNAs can be separated from the bulk of cellular RNA by affinity chromatography on oligodeoxythymidylate (oligo (dT))-cellulose columns using any methods known in the art. If the size of the mRNA encoding the desired protein is known, the mRNA preparation can be further purified for mRNA molecules of the particular size by agarose gel electrophoresis of the RNA.

Examples of appropriate molecular techniques for generating recombinant nucleic acids, and instructions sufficient to direct persons of skill through many closing exercises are found in Berger and Kimmel, *Guide to Molecular Cloning Techniques, Methods in Enzymology* (Volume 152 Academic Press, Inc., San Diego, Calif. 1987); *PCR Protocols: A Guide to Methods and Applications* (Academic Press, San Diego, Calif. 1990). Product information from manufacturers of biological reagents and experimental equipment also provide information useful in known biological methods. Such manufacturers include SIGMA (Saint Louis, Mo.), R&D systems (Minneapolis, Minn.), Pharmacia LKB Biotechnology (Piscataway, N.J.), Clontech Laboratories, Inc. (Palo Alto, Calif.), Aldrich Chemical Company (Milwaukee, Wis.), Invitrogen (San Diego, Calif.), Applied Biosystems (Fosters City, Calif.), as well as many other commercial sources known to one of skill in the art.

IV. Generating a Lysate

The present invention utilizes a cell lysate for in vitro translation of a target protein. For convenience, the organism used as a source for the lysate may be referred to as the source organism or host cell. Host cells may be bacteria, yeast, mammalian or plant cells, or any other type of cell capable of protein synthesis. A lysate comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-$tRNAf^{Met}$ synthetase, peptidyl transferase, initiation factors such as IF-1, IF-2, and IF-3, elongation factors such as EF-Tu, EF-Ts, and EF-G, release factors such as RF-1, RF-2, and RF-3, and the like.

In one embodiment, the lysate will be prepared in which the first exogenous aminoacyl-tRNA synthetase that will charge the first isoaccepting tRNA is not expressed in the host cell prior to lysis. In another embodiment, the lysate will be prepared in which both the first and second exogenous aminoacyl-tRNA synthetases that will charge the first and second isoaccepting tRNAs, respectively, will be expressed in the host cell prior to lysis. The retention or depletion of the necessary aminoacyl-tRNA synthetases prior to the tRNA charging reactions will be discussed forthcoming in the next section of this detailed description.

An embodiment uses a bacterial cell from which a lysate is derived. A bacterial lysate derived from any strain of bacteria can be used in the methods of the invention. The bacterial lysate can be obtained as follows. The bacteria of choice are grown up overnight in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients. Cells that have been harvested overnight can be lysed by suspending the cell pellet in a suitable cell suspension buffer, and disrupting the suspended cells by sonication, breaking the suspended cells in a French press, continuous flow high pressure homogenization, or any other method known in the art useful for efficient cell lysis The cell lysate is then centrifuged or filtered to remove large DNA fragments.

Another embodiment uses rabbit reticulocyte cells from which to derive a lysate. Reticulocyte lysate is prepared following the injection of rabbits with phenylhydrazine, which ensures reliable and consistent reticulocyte production in each lot. The reticulocytes are purified to remove contaminating cells which could otherwise alter the translational properties of final lysate. The cells can then be lysed by suspending the cell pellet in a suitable cell suspension buffer, and disrupting the suspended cells by sonication, breaking the suspended cells in a French press, or any other method known in the art useful for efficient cell lysis. After the reticulocytes are lysed, the lysate is treated with micrococcal nuclease and $CaCl_2$ in order to destroy endogenous mRNA and thus reduce background translation. EGTA is further added to chelate the $CaCl_2$ thereby inactivating the nuclease. Hemin may also be added to the reticulocyte lysate because it is a suppressor of an inhibitor of the initiation factor eIF2$\alpha$. In the absence of hemin, protein synthesis in reticulocyte lysates ceases after a short period of incubation (Jackson, R. and Hunt, T. 1983 *Meth. In Enzymol.* 96, 50). Potassium acetate and magnesium acetate are added at a level recommended for the translation of most mRNA species. For further detail on preparing rabbit reticulocyte lysate, one skilled in the art can refer to, e.g., Sambrook, et al., *Molecular Cloning: A Laboratory Manual, Second Edition* (Cold Spring Harbor Laboratory Press, Cold Spring Harbor, N.Y. 1989).

An embodiment may use a plant lysate such as wheat germ lysate. Generally, wheat germ lysate is prepared by grinding wheat germ in an extraction buffer, followed by centrifugation to remove cell debris. The supernatant is then separated by chromatography from endogenous amino acids and plant pigments that are inhibitory to translation. The lysate is also treated with micrococcalnuclease to destroy endogenous mRNA, to reduce background translation to a minimum. The lysate contains the cellular components necessary for protein synthesis, such as tRNA, rRNA and initiation, elongation, and termination factors. The lysate is further optimized by the addition of an energy generating system consisting of phosphocreatine kinase and phosphocreatine, and magnesium acetate is added at a level recommended for the translation of most mRNA species. For more detail on the preparation of wheat germ lysate, see e.g., Roberts, B. E. and Paterson, B. M. (1973), *Proc. Natl. Acad. Sci. U.S.A.* Vol. 70, No. 8, pp. 2330-2334), following the modifications described by Anderson, C. W., et al., *Meth. Enzymol.* (Vol. 101, p. 635; 1983).

Lysates are also commercially available from manufacturers such as Promega Corp., Madison, Wis.; Stratagene, La Jolla, Calif.; Amersham, Arlington Heights, Ill.; and GIBCO, Grand Island, N.Y.

In some embodiments of the present invention, a first exogenous aminoacyl-tRNA synthetase must be added to the lysate. This requirement exists in embodiments where the native aminoacyl-tRNA synthetase is depleted following lysis, and where the native aminoacyl-tRNA synthetase is not replaced in the host cell with two aminoacyl-tRNA synthetases that each recognize a specific isoaccepting sense tRNA. This requirement further exists in embodiments where the second isoaccepting tRNA is inactivated. In these embodiments, it is imperative that the first aminoacyl-tRNA synthetase that is added directly to the lysate only recognize the first isoaccepting sense tRNA. This requires the engineering of a first isoaccepting tRNA-specific aminoacyl-tRNA synthetase. Engineered aminoacyl-tRNA synthetases that recognize isoaccepting tRNAs may also be expressed within a host cell prior to lysis.

Aminoacyl-tRNA synthetases may be engineered to recognize an isoaccepting tRNA using a variety of methods generally used for protein directed evolution. Various types of mutagenesis used to produce novel aminoacyl-tRNA synthetases capable of charging the first isoaccepting sense tRNA directly in the lysate are well known in the art. See, e.g. Liu et al., Proc. Natl. Acad. Sci. 94:10092-7 (1997). Liu et al. utilized DNA shuffling (random point mutagenesis and in vitro homologous recombination) together with oligonucleotide-directed mutagenesis to generate libraries of mutant aminoacyl-tRNA synthetases. The synthetases were then selected for their ability to selectively charge the desired tRNA. These and other aminoacyl-tRNA synthetase engineering techniques are well known in the art. Other suitable methods of engineering aminoacyl-tRNA synthetases are further discussed below where in vitro tRNA aminoacylation is described.

V. Depletion of Native Aminoacyl-tRNA Synthetases

The present invention entails differentially charging isoaccepting sense tRNAs with either native or non-native amino acids. Therefore, some embodiments of the present invention include the depletion of a native aminoacyl-tRNA synthetase to prevent uncharged isoaccepting sense tRNA molecules from being charged with the incorrect native amino acid that would compete with the non-native amino acids for the second sense codon within the lysate. The native aminoacyl-tRNA synthetase may be depleted from the cell lysate either before lysis of the host cell population, or directly from the lysate following lysis of the host cell population. Some embodiments of the present invention further provide methods for the depletion of the second exogenous aminoacyl-tRNA synthetase from the lysate following lysis.

A. Depleting a Native Aminoacyl-tRNA Synthetase Prior to Lysis

In embodiments where the native aminoacyl-tRNA synthetase is depleted from the cell lysate before lysis, the host cell population may be altered such that the native aminoacyl-tRNA synthetase is replaced with an aminoacyl-tRNA synthetase that is fused to a tag referred to as a capture moiety. The native aminoacyl-tRNA synthetase may also be replaced with an aminoacyl-tRNA synthetase that is unstable. The native aminoacyl-tRNA synthetase is replaced by transforming said cells with a gene wherein said gene expresses the recombinant aminoacyl-tRNA synthetase of choice that is capable of functionally replacing the native aminoacyl-tRNA synthetase. The purpose of replacing the native aminoacyl-tRNA synthetase with a tagged aminoacyl-tRNA synthetase, or an aminoacyl-tRNA synthetase that is unstable, is to provide a simple manner in which the lysate will be cleared of an aminoacyl-tRNA synthetase capable of charging both isoaccepting sense tRNAs while retaining survival of the host cell population in the absence of the native aminoacyl-tRNA synthetase. Ways in which the native aminoacyl-tRNA synthetase or native aminoacyl-tRNA synthetase fused to a capture moiety are depleted is discussed in greater detail below.

In other embodiments where the native aminoacyl-tRNA synthetase is depleted from the cell lysate before lysis, the host cell population may be altered such that the native aminoacyl-tRNA synthetase is replaced with first and second exogenous aminoacyl-tRNA synthetases. The first and second exogenous aminoacyl-tRNA synthetases each specifically aminoacylate the first and second isoaccepting sense tRNAs, respectively. The native aminoacyl-tRNA synthetase is replaced by transforming said cells with two genes wherein one gene expresses the first exogenous aminoacyl-tRNA synthetase and the second gene expresses the second exogenous aminoacyl-tRNA synthetase. One way in which this can be accomplished is by using discriminating aminoacyl-tRNA synthetases found in nature that are specific to isoaccepting sense tRNAs. Such aminoacyl-tRNA synthetases exist, for example, in *Acidithiobacillus ferrooxidans*. See, e.g., Salazar et al., Proc. Natl. Acad. Sci. 100:13863-68 (2003).

The purpose of replacing the native aminoacyl-tRNA synthetase with two aminoacyl-tRNA synthetases that selectively charge different isoaccepting sense tRNAs is to provide a mechanism in which the first sense codon is aminoacylated with the native amino acid directly in the cell lysate. This occurs without having to either later remove the native aminoacyl-tRNA synthetase or add a purified first aminoacyl-tRNA synthetase directly to the lysate. In these embodiments, the second exogenous aminoacyl-tRNA synthetase must be depleted from the lysate to prevent the second isoaccepting sense tRNA from being charged with native amino acids. Depleting the second aminoacyl-tRNA synthetases from the lysate in these embodiments is discussed below.

When using a recombinant aminoacyl-tRNA synthetase that functionally replaces the native aminoacyl-tRNA synthetase prior to lysis, one also needs to alter the host cell such that the expression of the native aminoacyl-tRNA synthetase is inhibited. This may be accomplished by any method known in the art including, but not limited to, creating a host cell line that has a deletion for the entire DNA sequence that codes for the synthetase mRNA; deleting a portion of the DNA sequence that codes for the synthetase mRNA such that any resulting synthetase protein is rendered non-functional, where the deleted portion may include an exon, intron, promoter, or enhancer sequence; or introducing any type of exogenous intervening sequence into the coding or regulatory sequence of the endogenous aminoacyl-tRNA synthetase, such as a transposon, that functions to disrupt or completely inhibit the function of the synthetase. Methods of disrupting endogenous gene function are well known in the art, and should not be limited only to these discussed. Such methods are well known in the art, and are common to the practice of molecular biology. For greater detail on such techniques, see e.g., Sambrook et al., *Molecular Cloning—A Laboratory Manual*, 3*rd Ed*. (Cold Spring Harbor Laboratory Press, Cold Spring Harbor, N.Y. 2000).

In embodiments where an aminoacyl-tRNA synthetase is fused to a capture moiety to functionally replace the native aminoacyl-tRNA synthetase prior to lysis, the aminoacyl-tRNA synthetase fused to a capture moiety itself must be depleted from the lysate following lysis in order to prevent any cross-reactivity that might aminoacylate both isoaccepting sense tRNAs with the same amino acid. The aminoacyl-tRNA synthetase fused to a capture moiety may be depleted from the lysate by any method known in the art that will allow a tagged protein to be removed from a lysate, which may include but is not limited to, affinity chromatography, immunoaffinity chromatography, or immunoprecipitation.

In embodiments where an aminoacyl-tRNA synthetase fused to a capture moiety is depleted from the cell lysate by affinity chromatography, one may utilize a variety of tags known in the art. A common tag e.g., is a Histidine-tag (His-tag), which has an affinity towards nickel or cobalt ions. Here, the tagged aminoacyl-tRNA synthetase to be depleted may be engineered into a recombinant protein that will express the desired synthetase having the His-tag exist as part of the expressed protein. If one immobilizes nickel or cobalt ions on a resin column, an affinity support that specifically binds to histidine-tagged proteins can be created. As it relates to the present invention, the resin immobilized with either the nickel or cobalt ions is the binding moiety. Because the only protein in the lysate that will have a His-tag will be the aminoacyl-tRNA synthetase fused to the His-tag, that synthetase will be the only protein that will bind to the resin, letting all other proteins pass through the column. Such techniques are well known in the art, and His-tag vectors are commercially available from manufacturers such as Qiagen (Valencia, Calif.), Roche Applied Science (Rotkreuz, Switzerland), Biosciences Clontech (Palo Alto, Calif.), Promega (San Luis Obispo, Calif.) and Thermo Scientific (Rockford, Ill.).

Immunoaffinity chromatography may also be used to deplete the aminoacyl-tRNA synthetase fused to a capture moiety from the lysate. Immunoaffinity chromatography is a method of affinity chromatography that is achieved by tagging the aminoacyl-tRNA synthetase with a capture moiety that is recognized by an antibody. The capture moiety may be any tag that is commercially available and recognized by commercially available antibodies. Such tags may include, but are not limited to, Green Fluorescent Protein (GFP) tag, Glutathione-S-transferase (GST) tag, and the FLAG-tag tag. Immunoaffinity chromatography methods are well known in the art. For more detail on either affinity or immunoaffinity chromatography, see, e.g., *Affinity Chromatography: Principles & Methods* (Pharmacia LKB Biotechnology 1988), and Doonan, Protein Purification Protocols (The Humana Press 1996).

In another embodiment of the present invention, the aminoacyl-tRNA synthetase fused to a capture moiety may be depleted from the lysate by immunoprecipitation. In this embodiment, antibodies are raised against the capture moiety, but such systems often provide for the use of commercial antibodies raised against commercially available recombinant tags. The antibody is then immobilized on a solid-phase substrate binding moiety that may include, but is not limited to, microscopic superparamagnetic or microscopicagarose beads. The beads bind to the substrate of choice, and when added to the cell lysate, the proteins that are targeted by the antibodies are bonded onto the substrate. Alternatively, the antibodies may also be directly added to the lysate and allowed to associate with the targeted aminoacyl-tRNA synthetase to be depleted. Beads coated in Protein A/G are then added to the antibody/aminoacyl-tRNA synthetase mixture, at which time the antibodies and bound synthetase will bind to the Protein A/G beads. The substrate can then be removed from the lysate, for example, via magnetic fields for superparamagnetic substrates or centrifugation for microscopicagarose substrates. Immunoprecipitation methods are well known in the art. See, e.g. E. Harlow, *Antibodies: A Laboratory Manual* (Cold Spring Harbor Laboratory Press, Cold Spring Harbor, N.Y. 1988).

In some embodiments of the present invention, the native aminoacyl-tRNA synthetase is depleted prior to lysis and functionally replaced by transforming the host cell population with a recombinant aminoacyl-tRNA gene that produces an aminoacyl-tRNA synthetase that is thermally instable. Following cell lysis, heat can be used to denature the thermally instable aminoacyl-tRNA synthetase to prevent unwanted charging of the isoaccepting tRNA molecules within the lysate. Similarly, the host cell population can be replaced with a recombinant aminoacyl-tRNA synthetase gene that expresses an aminoacyl-tRNA synthetase that is unstable under ionic, physical, or chemical conditions.

B. Depleting a Native Aminoacyl-tRNA Synthetase Following Lysis

In embodiments where the native aminoacyl-tRNA synthetase is depleted from the cell lysate following lysis, replacing the aminoacyl-tRNA synthetase with either an aminoacyl-tRNA synthetase tagged with a capture moiety or a recombinant synthetase that is unstable is unnecessary. In these embodiments, immunoaffinity chromatography or immunoprecipitation may be used to deplete the endogenous native aminoacyl-tRNA synthetase. This embodiment requires raising antibodies against the native aminoacyl-tRNA synthetase. Once antibodies that sufficiently recognize the native aminoacyl-tRNA synthetase are raised, either immunoaffinity chromatography or immunoprecipitation, as described above, may be used to deplete the lysate of the native aminoacyl-tRNA synthetase.

In other embodiments where the native aminoacyl-tRNA synthetase is depleted following cell lysis, the native aminoacyl-tRNA synthetase may also be functionally depleted using an aminoacyl-tRNA synthetase inhibitor that is specific to that synthetase desired to be depleted. Many aminoacyl-tRNA synthetase inhibitors are amino acid analogs that inhibit a specific aminoacyl-tRNA synthetase, although a particular inhibitor may sometimes inhibit aminoacyl-tRNA synthetases associated with more than one amino acid. Aminoacyl-tRNA synthetase specific inhibitors can also be searched in databanks such as BioInfoBank (http://ia.bioinfo.pl/). A person skilled in the art would also readily recognize that a specific inhibitor can be designed, screened, and tested, based on the available structural models of aminoacyl-tRNA synthetases.

Examples of aminoacyl-tRNA synthetase inhibitors include S-trityl-L-cysteine; L-asparaginamide; 4-aza-DL-leucine; DL-serine hydroxamate; proflavine (hemisulfate salt); L-isoleucinol; N-phenylglycine; L-leucinol; L-methioninol; phe-leu-amide; tyramine; L-isoleucinol; 3,4-dehydro-DL-proline; S-carbamyl-L-cysteine; α-methyl-DL-methionine; chloro-L-alanine; cis-hydroxy proline; L-prolinol; L-histidonol; L-tyrprophan hydroxamate; DL-4-thiaisoleucine; DL-amino-.epsilon.-caprolactam; L-aspartic acid amide; DL-β-hydroxynorvaline; cis-4-fluoro-L-proline; trans-4-fluoro-L-carboxylic acid; α-methyl-DL-histidine; N-formyl-L-histidine; L-2-amino-3-sulfamoylpropionic acid; L-aspartic acid-β-hydroxamate; β-cyano-L-alanine; selenocystamine; 4-amino-n-butyric acid amide; DL-5-hydroxylysine; L-lysinhydroxamate; 3-(N-phenylacetyl) amino-2,6-piperidinedione (antineoplaston A10); 4-amino-4 phosphonobutyric acid; ethionamide; 1,2-diamino-3(4-imidazolyl) propane (histidinamine); α-methylhistidine; (S)-2-methylbutylamine; L-O-methylthreonine; DL-armentomycin (2-amino-4,4-dichlorobutyric acid); DL-3-dehydroarmentomycin; DL-3-hydroxyleucine; 5,5,5-trifluoro-DL-leucine; 1343-aminocyclohexyl)-DL-alanine; DL-p-chloroamphetamine; trans-2,6-diaminohex-4-enoic acid; DL-2,6-diphthalimidocaproic acid methyl ester; DL-5-hydroxylysine; L-lysinhydroxamate; DL-4-oxalysine; DL-4-selenalysine; L-methioninamide; 2-amino-4-methylhex-4-enoic acid; (1S,2S)-2-amino-1-phenyl-1,3-propanediol; N-benzyl-D-amphetamine; N-benzyl-L-phenylalanine; N-benzyl-D-phenylethylamine; 1,3-bis(acetoxy)-2-nitro-1-phenylpropane (fenitropan); 1,2-diamino-3-(2,6-dichlorophenyl)propane; 1,2-diamino-3-hydroxy-5-phenylpentane; 1,2-diamino-3-phenylpropane; N-(2,6-dichlorobenzylidene)-2-phenylethylamine; N-(2,6-dichlorobenzyl)-2-phenylethylamine; N-(4-fluorobenzyl)-L-phenylalanine; DL-2-fluorophenylalanine; 2-hydroxyethyl-2-phenylammonium sulfate; α- and β-methyl-DL-phenylalanine; L-phenylalaminol; L-α-phenylglycine; DL-threo-β-phenylserine; β-2-thienyl-DL-alanine; N-trifluoroacetyl-L-phenylalanine cyclohexyl ester; 2-aminomethyl-4-isopropyloxypyrrolidine oxalate; 2-amino-methylpyrrolidine; L-4-thiaproline; N-benzylethanolamine; N-(2,6-dichlorobenzyl)ethanolamine; N-(2,6-dichlorobenzylidene)ethanolamine; DL-β-hydroxyleucine; 1,2-diamino-5-phenyl-3-pentanol; DL-7-azatryptophan; DL-4- and DL-6-fluorotryptophan; 5-hydroxytryptamine; L-5-hydroxytryptophan; DL-α-methyltryptamine; α- and β-methyl-DL-tryptophan; tryptamine; DL-2-amino-1-(4-hydroxyphenyl)-1-propanol; DL-3-fluorotyrosine; 3-iodo-L-tyrosine; 3-nitro-L-tyrosine; L-tyrosinol.HCl; L-threo-2-amino-3-chlorobutyric acid; hexafluoro-DL-valine; DL-norvaline; L-4-thialysine; DL-ethionine; N,N'-di-CBZ-L-lysine; DL-3-fluorophenylalanine; DL-4-fluorophenylalanine; and DL-3,4-dihydroxyphenylalanine. These compounds are known in the art.

C. Depleting an Exogenous Aminoacyl-tRNA Synthetase Following Lysis

In embodiments where the native aminoacyl-tRNA synthetase is functionally replaced within the host cell by two exogenous aminoacyl-tRNA synthetase, the second exogenous aminoacyl-tRNA synthetase must be removed from the lysate following lysis, as mentioned above.

The second exogenous aminoacyl-tRNA synthetase may be depleted from the cell lysate by fusing the second exogenous aminoacyl-tRNA synthetase to a capture moiety, and depleting said second exogenous aminoacyl-tRNA synthetase from the lysate by affinity chromatography, immunochromatography using an antibody that recognizes the capture moiety, or immunoprecipitation using an antibody that recognizes the capture moiety. The second exogenous aminoacyl-tRNA synthetase may further be removed if said synthetase is unstable, e.g., thermally unstable. In embodiments where the host cell population expresses two exogenous aminoacyl-tRNA synthetases, the second exogenous aminoacyl-tRNA synthetase may be further deleted from the lysate by using either immunoaffinity chromatography or immunoprecipitation using an antibody that specifically recognizes the second exogenous aminoacyl-tRNA synthetase, or by using competitive inhibitors specific to the second exogenous aminoacyl-tRNA synthetase. These techniques are discussed in greater detail above with respect to depleting native aminoacyl-tRNA synthetases.

Whilst the methods listed above for depleting proteins are the most commonly employed in the art, the methods of the present invention should not be limited only to those procedures described above. Any functional means for depleting a native aminoacyl-tRNA synthetase will accord with the methods of incorporating non-native amino acids as claimed in the present invention.

In embodiments that provide a cell-free lysate, the lysate may be from a wide variety of cells. Embodiments utilize rabbit reticulocyte cells. Preferred embodiments utilize bacterial cells, specifically *E. coli* cells. Embodiments that use bacterial cells utilize lysates that exhibit a functional oxidative phosphorylation system. Embodiments further provide lysates that are deficient in arginine decarboxylase.

VI. Inactivating tRNA Molecules

One manner in which the present invention may be practiced is by inactivating the native second isoaccepting tRNA. In these embodiments, the native aminoacyl-tRNA synthetase is not depleted, but is preserved within the lysate in order to function as an aminoacylating synthetase necessary for the charging the first isoaccepting tRNA with the native amino acid that is normally acylated to said first isoaccepting tRNA. The source of the native amino acid are those produced by the host cell population, and are therefore present within the lysate immediately following lysis.

An embodiment of the present invention that inactivates the second isoaccepting tRNA uses antisense DNA. Here, the antisense DNA recognizes the anticodon sequence of its target tRNA, hence preventing the native isoaccepting tRNA from associating with its mRNA codon sequence.

Inactivating and depleting tRNA molecules is well known in the art. See, e.g., Lindsley and Guarneros, Mol. Microbiology. 48:1267-74 (2003); Jackson et al. RNA 7:765-73 (2001); Kanda et al, Biochem. Biophys. Res. Commun., 270: 1136-9 (2000); Kanda et al., FEBS Letters 440:273-76 (1998); Kanda et al., Bioorganic & Medicinal Chemistry 8:675-79; Schmidt and Schimmel, PNAS 90:6919-23 (1993).

Specific t-RNA ribonucleases (tRNAses) can be used to inactive specific tRNAs by selectively cleaving specific tRNAs. Examples of specific tRNAses include colicin D, colicin E5, and PrrC. See, e.g., Tomita et al., Proc. Natl. Acad. Sci. 97:8278-83 (2000); Morad et al., J. Biol. Chem. 268: 26842-9 (1993); Ogawa et al., 283:2097-2100 (1999); de Zamarozy et al., Mol. Cell. 8:159-168 (2001). Active fragments of these specific t-RNA ribonucleases, e.g., C-terminal domain of colicin D or colicin E5, can be used for the present invention. Specific t-RNA ribonucleases can be further engineered to inactivate a subset of their target t-RNAs, or can be altered to inactivate a different tRNA target. When the ribonuclease activity is not longer desired, the tRNAses may be inhibited by an inhibitor, e.g., ImmD protein (see, e.g., de Zamarozy et al.).

VII. In Vitro tRNA Aminoacylation

The tRNA charging reaction, as used herein, refers to the in vitro tRNA aminoacylation reaction in which the second isoaccepting sense tRNA that will be aminoacylated with the non-native amino acid is charged. The tRNA charging reaction comprises the charging reaction mixture, an isoaccepting sense tRNA, and a non-native amino acid.

The present invention is a mono charging system because the second isoaccepting sense tRNA that is charged with a non-native amino acid occurs in a tRNA charging reaction separate from the protein synthesis reaction. The first isoaccepting sense tRNA is not charged in a tRNA charging reaction, but is charged with a native amino acid directly within the cell lysate or within the host cell prior to lysis. In one embodiment of the present invention in which the native aminoacyl-tRNA synthetase is depleted following cell lysis, the first exogenous aminoacyl-tRNA synthetase that only recognizes the first isoaccepting sense tRNA is added to the lysate following cell lysis. In another embodiment where the native aminoacyl-tRNA synthetase is replaced with the two exogenous aminoacyl-tRNA synthetases, the first exogenous aminoacyl-tRNA synthetase is expressed in the host cell prior to cell lysis, and therefore is already present in the lysate following lysis. In another embodiment where the second isoaccepting tRNA is inactivated, the first isoaccepting tRNA is charged with the endogenous native amino acid directly in the lysate by the native aminoacyl-tRNA synthetase. In all embodiments mentioned within this paragraph, the second isoaccepting sense tRNA is charged with a non-native amino acid in a tRNA charging reaction separate from the protein synthesis reaction.

The separate tRNA charging reaction can be any reaction that aminoacylates a tRNA molecule with a desired amino acid separate from the protein synthesis reaction. This reaction can take place in an extract, an artificial reaction mixture, or a combination of both.

Suitable tRNA aminoacylation reaction conditions are well known to those of ordinary skill in the art. Typically, tRNA aminoacylation is carried out in a physiological buffer with a pH value ranging from 6.5 to 8.5, 0.5-10 mM high energy phosphate (such as ATP), 5-200 mM $MgCl_2$, 20-200 mM KCl. Preferably, the reaction is conducted in the presence of a reducing agent (such as 0-10 mM dithiothreitol). Where the aminoacyl-tRNA synthetase is exogenously added, the concentration of the synthetase is typically 1-100 nM. One skilled in the art would readily recognize that these conditions can be varied to optimize tRNA aminoacylation, such as high specificity for the pre-selected amino acids, high yields, and lowest cross-reactivity.

The reaction can be carried out in a temperature ranging from 4 to 40° C., or more preferably 20-37° C. Where the cell lysate is derived from a thermophilic bacteria, the reaction may be carried out in a higher temperature (e.g. 70° C.). Where a thermally unstable aminoacyl-tRNA synthetase is used, the reaction is preferably carried out in a lower temperature (e.g. 4° C.). The reaction temperature may also be varied to optimize tRNA aminoacylation. The precise reaction conditions in which an isoaccepting sense tRNA is charged with an amino acid in the tRNA charging reaction is illustrated in the examples provided herein.

In a preferred embodiment of the invention, the second isoaccepting sense tRNA is charged by an aminoacyl-tRNA synthetase. In this embodiment, the second isoaccepting tRNA that associates with a different codon sequence, but for the same amino acid as the codon for the first isoaccepting sense tRNA, would be charged with a non-native amino acid in a tRNA charging reaction separate from the lysate in which the protein synthesis reaction proceeds. Because the second isoaccepting tRNA charging reaction would occur in a separate reaction, restrictions as to what types of aminoacyl-tRNA synthetases can be used for charging the second isoaccepting tRNA is minimal.

The second isoaccepting sense tRNA charging reaction can thus utilize either the native aminoacyl-tRNA synthetase specific to the tRNAs to be charged, the second exogenous aminoacyl-tRNA synthetase expressed in the host cell for some of the embodiments discussed for the present invention, an aminoacyl-tRNA synthetase engineered to recognize a non-native amino acid, or a "promiscuous" aminoacyl tRNA synthetase capable of charging a tRNA molecule with more than one type of amino acid. Promiscuous aminoacyl-tRNA synthetases may include endogenously produced aminoacyl-tRNA synthetases that are sometimes found in nature.

Engineered aminoacyl-tRNA synthetases useful for charging the second isoaccepting tRNA with a non-native amino acid may be engineered using a variety of methods generally used for protein directed evolution. Such methods of mutagenesis are discussed above with respect to lysate preparation, but may also include, not being limited to, site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mis-match repair, mutagenesis using repair-deficient host strains, restriction-selection and restriction-purification, deletion mutagenesis, mutagenesis by total gene synthesis, double-strand break repair, and the like. The mutants are then screened using a functional assay for desired activity. For example, the editing function of the aminoacyl-tRNA synthetases can be eliminated. Mutagenesis, e.g., involving chimeric constructs, can also be used. Engineering aminoacyl-tRNA synthetases to recognize non-native amino acids has become well known in the art. See, e.g. Liu et al., Proc. Natl. Acad. Sci. 94:10092-7 (1997); Furter, Protein Sci., 7:419 (1998); Zhang et al., Proc. Natl. Acad. Sci. 94:4504-09 (1997); Ohno et al., J. Biochem. 130:417-23 (2001); Kiga et al., Proc. Natl. Acad. Sci. 99:9715-9723 (2002).

For efficiently charging a modified tRNA and/or a non-native amino acid, the aminoacyl-tRNA synthetase can be engineered to aminoacylate the modified tRNA with a non-native amino acid under conditions similar to native reaction conditions. Engineering tRNA/aminoacyl-tRNA synthetase pairs is discussed above. An example of engineered synthetases is Ala294→Gly Phe-RS, with the Ala294→Gly mutation at the active site of the synthetase. In some embodiments, an engineered synthetase allows the aminoacylation of a modified tRNA and/or a non-native amino acid under conditions similar to normal reaction conditions Alternatively, a modified tRNA and/or a non-native amino acid can be charged under gently-denaturing reaction conditions, e.g., elevated pH, increased MgCl2 concentrations, the addition of detergents, DMSO, or spermidine. An example of such reaction conditions includes: 100 mM Hepes pH 8.1, 75 mM $MgCl_2$, 5 mM ATP, 40 mM KCl, 1.4 M DMSO, 0.1% Triton X-100, 10-100 μM tRNAphe, 5-20 mM p-acetyl-phenylalanine, and 1-10 μM Ala294→Gly Phe-RS. In some embodiments, a modified tRNA and/or a non-native amino acid can be charged under the gently-denaturing reaction conditions by a native aminoacyl-tRNA synthetase.

In some biological systems, isoaccepting codons are naturally serviced by the same tRNA, with the first codon perfectly matched by the tRNA and the second codon mismatched by wobble base-paring. In these systems, it is possible to introduce a modified tRNA that thermodynamically favors the second codon, i.e., perfectly matching the second codon.

Therefore, engineered tRNA/aminoacyl-tRNA synthetase pairs useful for the charging reaction further include a system utilizing a modified tRNA derived from a native tRNA. The native tRNA forms Watson-Crick base-pairing with a first sense codon encoding a native amino acid, and forms wobble base-pairing with one or more wobble degenerate sense codon(s) encoding the same native amino acid. The modified tRNA according to the present invention comprises a modified anticodon sequence that forms a perfect Watson-Crick base-pairing with one of the wobble degenerate sense codon(s).

Examples of engineered tRNAs useful for, e.g., bacterial systems or other systems, include an asparagine tRNA in which the anticodon GUU has been modified to an anticodon AUU (GUU→AUU); a GCA→ACA cysteine tRNA; a UUC→CUC glutamine tRNA; a GUG→AUG histidine tRNA; a UUU→CUU lysine tRNA; an CGU→AGU threonine tRNA. Examples of non-native amino acids to be charged further include, e.g., fluoro-glutamine and para-acetyl-phenylalanine In some embodiments, the modified tRNA is charged with a non-native amino acid by an engineered aminoacyl-tRNA synthetase. An example of engineered tRNA is an engineered *E. coli* phenylalanine tRNA in which the anticodon GAA has been modified to an anticodon AAA (see Kwon et al., JACS 125:7512-7513, 2003). An example of engineered aminoacyl-tRNA synthetase is a modified phenylalanine-tRNA synthetase, e.g., a Thr415Gly mutant. An example of non-native amino acids to be charged using the engineered tRNA/aminoacyl-tRNA synthetase pair is L-3-(2-naphthyl)alanine (Nal).

Following the aminoacylation of the isoaccepting sense tRNA in the separate charging reaction, the charged isoaccepting sense tRNA must be purified in order to add it to the cell-free protein synthesis reaction. This aspect of the invention requires the charged isoaccepting sense tRNA to be isolated from the aminoacyl-tRNA synthetase used in the tRNA charging reaction to ensure that the synthetases utilized for the charging reaction do not cross react with the tRNAs and/or amino acids in the protein synthesis reaction.

Amino-acylated tRNA may be purified from unreacted tRNA and any aminoacyl-tRNA synthetase using elongation factor-Tu (Ef-Tu) from *E. coli* or *T. thermophilis*, immobilized on Sepharose 4B (GE Healthcare) see Derwnskus, Fischer, & Sprinzl, Anal. Biochem., 136, 161 (1984). Briefly, the immobilized protein is activated in the presence of GTP, pyruvate kinase, and phosphoenolpyruvate to generate immobilized Ef-Tu-GDP that specifically binds the amino-acylated tRNA. The column is washed in low ionic strength buffer (10 mM KCl; 50 mM HEPES; pH 7.4) and eluted in high salt buffer to yield purified amino-acylated tRNA.

Another embodiment charges the second isoaccepting sense tRNA with a non-native amino acid using a ribozyme column that is capable of transferring an aminoacyl group from the 5'-OH of the ribozyme (after being charged by an oligonucleotide donor) to the 3'-OH of the tRNA molecule. Ribozymes currently employed in the art result in the ability to catalyze reactions between a broad spectrum of tRNAs and non-native amino acids, which is particularly useful for making tRNAs aminoacylated with non-native amino acids when using in vitro translation reactions. Ribozymes currently known in the art further enable efficient affinity purification of the aminoacylated products, examples of suitable substrates including agarose, sepharose, and magnetic beads. Such methods bypass the requirement for aminoacyl-tRNA synthetases in order for proper tRNA charging. Isoaccepting tRNAs that are aminoacylated using ribozymes can be accomplished in a variety of ways. One suitable method is to elute the aminoacylated isoaccepting tRNAs for a column with a buffer such as EDTA. See, e.g., Bessho et al., Nature Biotechnology 20:723-28 (2002); Lee et al., Nat. Struct. Biol. 20:1797-806 (2001).

tRNA molecules to be used in the tRNA charging reaction can be synthesized from a synthetic DNA template for any tRNA of choice following amplification by PCR in the presence of appropriate 5' and 3' primers. The resulting double-stranded DNA template, containing a T7-promoter sequence, can then be transcribed in vitro using T7 RNA polymerase to produce the tRNA molecule, which is subsequently added to the tRNA charging reaction see Sherlin et al. *RNA* 2001 7: 1671-1678.

Related to the in vitro tRNA aminoacylation described herein, the present invention also provides for a novel charged tRNA solution comprising a cell lysate having charged tRNAs bearing pre-selected amino acids, recognizing sense codons. The present invention involves the use of in vitro tRNA charging solutions that are added to the cell-free system. In some embodiments, the charging tRNA solutions lack significant synthetase activity. Examples of suitable cell lysates include a bacterial cell lysate. Examples of pre-selected amino acids include a non-native amino acid.

The charged tRNA bearing pre-selected amino acids can be made using the methods described in the present invention, or can be made other methods known in the art. For example, the charged tRNA bearing pre-selected amino acids can be prepared by chemical modification of a tRNA (see, e.g., Sando et al., *JACS* 127:7998-7999, 2005).

The charged tRNA solution according to the present invention can have no significant synthetase activity for the charged tRNA bearing the pre-selected amino acids. The synthetase or synthetase activity for the charged tRNA bearing the pre-selected amino acids can be depleted by the methods described in section V. For example, the tRNA solution can be depleted of significant synthetase activity for the charged tRNA bearing the pre-selected amino acids by immunoaffinity chromatography, immunoprecipitation, or by the addition of an aminoacyl-tRNA synthetase inhibitor.

In some embodiments, the synthetase activity for the charged tRNA bearing pre-selected amino acids is depleted using a method other than synthetase inhibition using an inhibitor. For example, the charged tRNA solution comprises a bacterial cell lysate having charged tRNAs bearing pre-selected amino acids, recognizing sense codon and having no significant synthetase activity for the charged tRNAs bearing pre-selected amino acids, and the charged tRNA solution is free of synthetase inhibitors or specific synthetase inhibitors.

VIII. Cell-Free Protein Synthesis Reaction

The above described charged isoaccepting sense tRNAs associated with the first and second codons are now combined with the cell lysate along with the nucleic acid template for synthesis of the desired protein having non-native amino acids as preselected positions.

The reaction mixture will further comprise monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. In addition to the above components such as a cell-free extract, genetic template, and amino acids, materials specifically required for protein synthesis may be added to the reaction. The materials include salts, folinic acid, cyclic AMP, inhibitors for protein or nucleic acid degrading enzymes, inhibitors or regulators of protein synthesis, adjusters of oxidation/reduction potentials, non-denaturing surfactants, buffer components, spermine, spermidine, putrescine, etc. Metabolic inhibitors to undesirable enzymatic activity may be added to the reaction mixture. Alternatively, enzymes or factors that are responsible for undesirable activity may be removed directly from the extract, or the gene encoding the undesirable enzyme may be inactivated or deleted from the chromosome.

The cell-free synthesis reaction may utilize a large scale reactor, small scale reactor, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

In embodiments wherein a DNA template is used to drive in vitro protein synthesis, the individual components of the protein synthesis reaction mixture may be mixed together in any convenient order. RNA polymerase is added to the reaction mixture to provide enhanced transcription of the DNA template. RNA polymerases suitable for use herein include any RNA polymerase that functions in the bacteria from which the bacterial extract is derived. In embodiments wherein an RNA template is used to drive in vitro protein synthesis, the components of the reaction mixture can be admixed together in any convenient order, but are preferably admixed in an order wherein the RNA template is added last.

The reaction mixture can be incubated at any temperature suitable for the transcription and/or translation reactions. The reaction mixture can be agitated or unagitated during incubation. The use of agitation may enhance the speed and efficiency of protein synthesis by keeping the concentrations of reaction components uniform throughout and avoiding the formation of pockets with low rates of synthesis caused by the depletion of one or more key components. The reaction can be allowed to continue while protein synthesis occurs at an acceptable specific or volumetric rate, or until cessation of protein synthesis, as desired. The reaction can be conveniently stopped by incubating the reaction mixture on ice, or rapid dilution with water or an appropriate buffer. The reaction can be maintained as long as desired by continuous feeding of the limiting and non-reusable transcription and translation components.

Various cell-free synthesis reaction systems are well known in the art. See, e.g., Kim, D. M. and Swartz, J. R. Biotechnol. Bioeng. 66:180-8 (1999); Kim, D. M. and Swartz, J. R. Biotechnol. Prog. 16:385-90 (2000); Kim, D. M. and Swartz, J. R. Biotechnol. Bioeng. 74:309-16 (2001); Swartz et al., Methods Mol. Biol. 267:169-82 (2004); Kim, D. M. and Swartz, J. R. Biotechnol. Bioeng. 85:122-29 (2004); Jewett, M. C. and Swartz, J. R., Biotechnol. Bioeng. 86:19-26 (2004); Yin, G. and Swartz, J. R., Biotechnol. Bioeng. 86:188-95 (2004); Jewett, M. C. and Swartz, J. R., Biotechnol. Bioeng. 87:465-72 (2004); Voloshin, A. M. and Swartz, J. R., Biotechnol. Bioeng. 91:516-21 (2005).

Cell-free protein synthesis can exploit the catalytic power of the cellular machinery. Obtaining maximum protein yields in vitro requires adequate substrate supply, e.g. nucleoside triphosphates and amino acids, a homeostatic environment, catalyst stability, and the removal or avoidance of inhibitory byproducts. The optimization of in vitro synthetic reactions benefits from recreating the in vivo state of a rapidly growing organism. In some embodiments of the invention, cell-free synthesis is therefore performed in a reaction where oxidative phosphorylation is activated, i.e. the CYTOMIM™ system.

The CYTOMIM™ system is defined by using a reaction condition in the absence of polyethylene glycol with optimized magnesium concentration. The CYTOMIM™ system does not accumulate phosphate, which is known to inhibit protein synthesis, whereas conventional secondary energy sources result in phosphate accumulation.

The concentration of magnesium in the reaction mixture affects the overall synthesis. There is often magnesium present in the cell lysate, which may then be adjusted with additional magnesium to optimize the concentration. The CYTOMIM™ system utilizes a preferred concentration of magnesium at least about 5 mM, usually at least about 10 mM, and preferably at least about 12 mM, and at a concentration of not more than about 20 mM, and usually not more than about 15 mM. Other changes that may enhance synthesis with respect to the CYTOMIM™ system is the removal of HEPES buffer and phosphoenol pyruvate from the reaction mixture. The CYTOMIM™ system is described in U.S. Pat. No. 7,338,789, herein incorporated by reference.

In some embodiments of the invention, cell-free synthesis is performed in a reaction where the redox conditions in the reaction mixture is optimized. This may include adding a redox buffer to the reaction mix in order to maintain the appropriate oxidizing environment for the formation of proper disulfide bonds. The reaction mixture may further be modified to decrease the activity of endogenous molecules that have reducing activity. Preferably such molecules can be chemically inactivated prior to cell-free protein synthesis by treatment with compounds that irreversibly inactivate free sulfhydryl groups. The presence of endogenous enzymes having reducing activity may be further diminished by the use of extracts prepared from genetically modified cells having inactivation mutations in such enzymes, for example thioredoxin reductase, glutathione reductase, etc. Alternatively, such enzymes can be removed by selective removal from the cell extract during its preparation. Maximizing redox conditions is described in U.S. Pat. Nos. 6,548,276 and 7,041,479, herein incorporated by reference.

In some embodiments of the invention, cell-free synthesis is performed in a reaction where the optimal amino acid concentration is maintained by inhibiting enzymes that act to undesirably metabolize specific amino acids Inhibition of enzymes that catalyze the metabolism of amino acids can be achieved by addition of inhibitory compounds to the reaction mix, modification of the reaction mixture to decrease or eliminate the responsible enzyme activities, or a combination of both. A preferred embodiment eliminates arginine decarboxylase. Other such inhibitory compounds to be eliminated from the protein synthesis reaction mixture may include, but are not limited to, tryptophanase, alanine glutamate transaminase, or pyruvate oxidase. Eliminating enzymatic activity in order to optimize amino acid metabolism during cell-free protein synthesis is described in U.S. Pat. No. 6,994,986, herein incorporated by reference.

Following the in vitro synthesis reaction, synthesized proteins containing non-native amino acids can be purified as is standard in the art. Proteins of the invention can be recovered and purified by methods including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis, etc. Newly synthesized proteins containing non-native amino acids must be correctly folded. Proper folding may be accomplished using high performance liquid chromatography (HPLC), affinity chromatography, or other suitable methods where high purity is desired. A variety of purification/protein folding methods are known in the art, e.g., Deutscher, *Methods in Enzymology Vol. 182: Guide to Protein Purification* (Academic Press, Inc. N.Y. 1990); Bollag et al., *Protein Methods, 2nd Edition*, (Wiley-Liss, N.Y. 1996).

Following purification, proteins containing non-native amino acids can possess a conformation different from the desired conformations of the relevant polypeptides. In general, it is occasionally desirable to denature and reduce expressed polypeptides and then to cause the polypeptides to re-fold into the preferred conformation. For example, guanidine, urea, DTT, DTE, and/or a chaperone can be added to a translation product of interest. methods of reducing, denaturing and renaturing proteins are well known to those of skill in the art. See, e.g. Debinski et al., J. Biol. Chem. 268:14065-70 (1993); Buchner et al., Anal. Biochem. 205:263-70 (1992).

The methods of the present invention provide for modified proteins containing non-native amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on coomasie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater. See, e.g., Sambrook et al., *Molecular Cloning: A Laboratory Manual* (Cold Spring Harbor Press, Cold Spring Harbor, N.Y. 1989).

Following the in vitro synthesis reaction and subsequent purification, the desired protein containing the non-native amino acids may be optionally used e.g., as assay components, therapeutic reagents, or as immunogens for antibody production.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

General Methods

Standard methods in molecular biology are described (Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning,* 3yd ed., Cold Spring Harbor Laboratory Press, Cold Spring Harbor, N.Y.; Wu (1993) *Recombinant DNA*, Vol. 217, Academic Press, San Diego, Calif.). Standard methods also appear in Bindereif, Schön, & Westhof (2005) *Handbook of RNA Biochemistry*, Wiley-VCH, Weinheim, Germany which describes detailed methods for RNA manipulation and analysis.

Methods for protein purification, chromatography, electrophoresis, centrifugation, and crystallization are described (Coligan et al. (2000) *Current Protocols in Protein Science, Vol.* 1, John Wiley and Sons, Inc., New York). Methods for cell-free synthesis are described in Spirin & Swartz (2008) *Cell-free Protein Synthesis*, Wiley-VCH, Weinheim, Germany. Methods for incorporation of non-native amino acids into proteins using cell-free synthesis are described in Shimizu et al (2006) FEBS Journal, 273, 4133-4140.

Example 2

In Vitro Transcription and Isolation of tRNA 2',3'-Cyclic Phosphate

Figure 3:
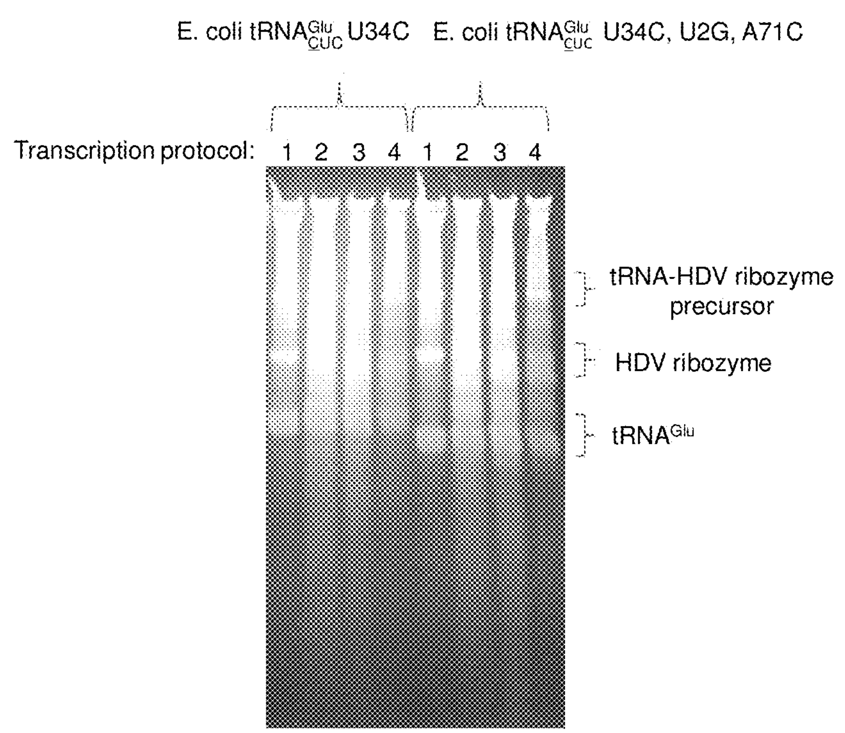
FIG. 3 shows TBE/UREA gels for protocols 1-4 used for optimization of in vitro transcription of two different engineered *E. coli* tRNA$_{CUC}^{Glu}$ constructs. Both constructs are mutated at U34C to produce a CUC anticodon; the rightmost construct contains additional noted mutations that should theoretically increase transcription yield.
Figure 4:
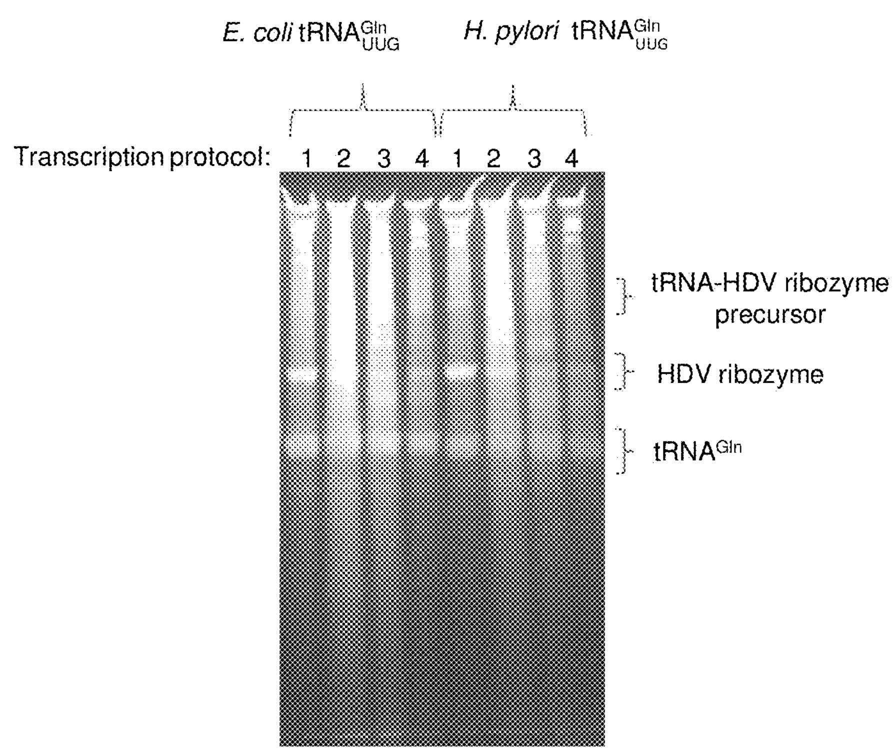
FIG. 4 shows TBE/UREA gels of in vitro transcription protocols 1-4 for two different engineered tRNA$_{UUG}^{Gln}$ constructs from *E. coli* and *H. pylori*, respectively.

Isoaccepting tRNAs aminoacylated with non-native amino acids can be produced from a designed tRNA-HDV ribozyme template DNA, illustrated by example in FIG. 1, by in vitro transcription, followed by purification by size exclusion chromatography (SEC), enzymatic removal of the 2',3'-cyclic phosphate, and charging of the tRNA with non-native amino acids (nnAAs) using engineered tRNA synthetase enzymes, as illustrated in FIG. 2. In order to optimize the transcription yield, four different in vitro transcription protocols were tested for the tRNA transcripts illustrated in FIG. 3 and FIG. 4. All four different in vitro transcription protocols gave similar tRNA yields. Transcription optimization was generally carried out for 2-3 h at 37° C. in 50 μL reactions. Reaction conditions were as follows: (1) 40 mM HEPES (pH 7.9), 10 mM DTT, 10 mM $MgCl_2$, 2.5 mM spermidine, 4 U/ml pyrophosphatase, 0.4 U/ml supeRNAse-in (Ambion), 20 mM NaCl, 4 mM NTP, 0.024 mg/ml T7 RNA polymerase, 0.028 mg/ml plasmid DNA template. (2) 80 mM HEPES (pH 7.5), 5 mM DTT, 22 mM $MgCl_2$, 1 mM Spermidine, 0.12 mg/ml Bovine Serum Albumin (BSA), 1 U/ml pyrophosphatase, 0.4 U/ml SupeRNAse-in, 3.75 mM NTPs, 0.024 mg/ml T7 RNA polymerase, 0.028 mg/ml plasmid DNA template (3) 30 mM HEPES (pH 7.9) 10 mM DTT, $MgCl_2$, 2 mM Spermidine, 1 U/ml pyrophosphatase, 0.4 U/ml supeRNAse-in, 4 mM NTPs, 0.024 mg/ml T7 RNA polymerase, 0.028 mg/ml plasmid DNA template. (4) 40 mM HEPES (pH 8.0), 10 mM DTT, 46 mM $MgCl_2$; 2 mM Spermidine, 0.4 U/ml supeRNAse-in, 10 mM NaCl, 3 mM NTP, 0.024 mg/ml T7 RNA polymerase, 0.028 mg/ml plasmid DNA template. In contrast to previous findings (Bindereif, Schon, & Westhof (2005)), we found that templates encoding for Uracil at position 1 or 2 of the tRNA (e.g. constructs 1 and 4) were not seriously defective for transcription by T7 RNA polymerase. As a result, the construct 1 $tRNA_{CUC}^{Glu}$ was preferred. The tRNA product produced using Protocol 1 was the most homogenous so this protocol was used for large-scale transcriptions with the exceptions noted below.

To produce large amounts of $tRNA_{CUA}^{Phe}$, $tRNA_{AAA}^{Phe}$ or $tRNA_{CUA}^{Glu}$ construct 1, 100 mL transcriptions were set up in certified RNAse free 50 ml conical tubes. For example, large scale reactions for $tRNA_{CUA}^{Glu}$ construct 1 contained 0.4 U/μL pyrophosphatase and 0.04 U/μL superRNAse-in were used. Transcription reactions were incubated for 2 hours at 37° C., supplemented with another 0.024 mg/ml T7 RNA polymerase and incubated for 2 more hours at 37° C., then filtered through 0.20 μm PES filters (VWR catalog #87006-062).

Figure 5:
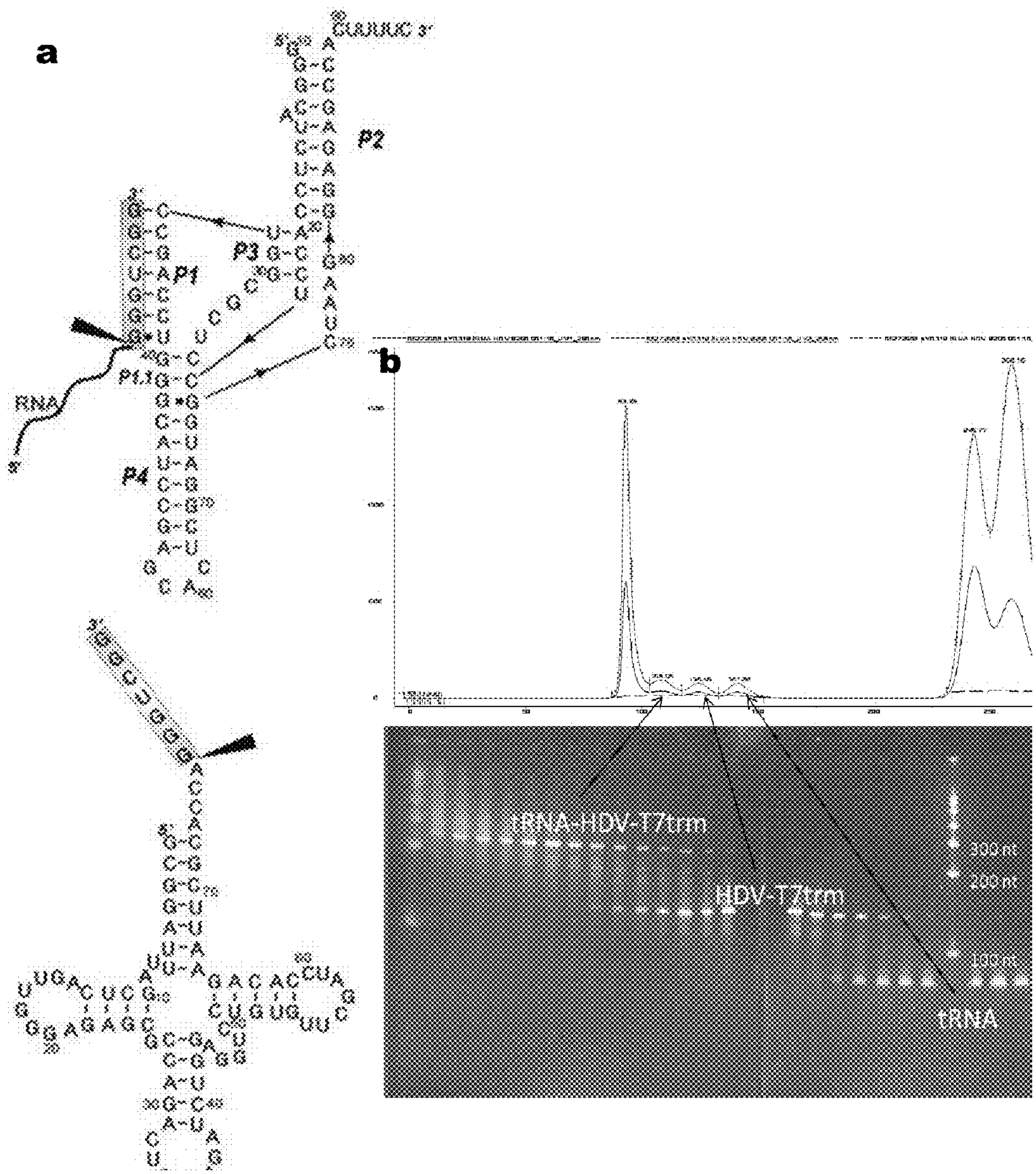
FIG. 5 shows (a) an illustration of the Hepatitis Delta Virus (HDV) consensus sequence used for generating 3' homogeneous tRNA (SEQ ID NOS:8-12). The autocatalytic ribozyme cleaves at the 3' end of the tRNA leaving a 2',3'-cyclic phosphate that is subsequently removed before aminoacylation. (b) Size exclusion chromatographic separation of the transcription product illustrating separation of the 73 nucleotide tRNA 2',3'-cyclic phosphate product from the self-cleaved HDV ribozyme.

Typically, aliquots of 50 mL transcriptions were loaded onto a 2 L Sephacryl S-100 or S-300 size exclusion resin in XK50/100 columns using an AKTA with 50 mM Tris (pH 6.5), 250 mM NaCl, 0.1 mM EDTA to separate tRNA-2,3' cyclic phosphate from precursor RNA transcripts and cleaved HDV ribozyme RNA (FIG. 5). 25 mL fractions were collected and tRNA peak fractions were determined by TBE/UREA PAGE gel electrophoresis. tRNA-2,3' cyclic diphosphate was precipitated by adding 1/10 volume 3 M sodium acetate (pH 5.2) and an equal volume of isopropanol, followed by incubation for 30 minutes at −80° C., and pelleting tRNA by centrifugation (20,000×g for 30 min in a FiberLite F-13 rotor). Pellets were washed with 70% ethanol, air dried briefly, then resuspended in 1 mM sodium citrate buffer (pH 6.4).

Production of *H. pylori* $tRNA_{UUG}^{Gln}$ (2 ml) was carried out using Protocol 1. tRNA purification was performed with a 26/60 Sephacryl S-200 size exclusion column (FIGS. 2*a* and 2*b*). EDTA was omitted from the sizing column buffer. *H. pylori* tRNAGln was resuspended in 50 mM Tris (pH 8.5).

In the course of these experiments we found that (1) addition of 0.1 mM EDTA and (2) addition of RNAse inhibitor in the transcription reactions prevents degradation of RNA (compare lanes 1 and 2 of FIG. 6A), due presumably due to significant RNAse contamination in NTPs (Sigma Aldrich catalog #: U6625; G8877, C1506, A7600). As shown in FIG. 6B intact purified $tRNA^{Glu}$ incubated overnight at 37° C. with NTPs was completely degraded (lane 2), however, addition of RNAse inhibitor abrogated this degradation (lane 3). This degradation was unlikely due to simple metal dependent cleavage as addition of EDTA did not affect degradation lane (lane 4). (Incubation with EDTA alone produces no tRNA degradation (lane 5).) Second, we found in that in some cases, tRNA purified without EDTA in the sizing column buffer and without a chelating agent in the resuspension buffer was susceptible to damage/degradation in the presence reducing agents (FIG. 6C; compare lanes 1 and 2), perhaps due to heavy metal contamination of tRNAs as it can be abrogated with the addition of EDTA (lane 3).

Example 3

Dephosphorylation of tRNA 2',3'-Cyclic Phosphate to Release Active tRNA

T4 polynucleotide kinase (PNK), required for the removal of the 2'-3' cyclic phosphate from tRNA cleaved by HDV ribozyme (cf. FIGS. 2 & 5), was produced as follows, The PNK gene with an N-terminal 6-Histidine tag (SEQ ID NO:13) was gene synthesized (DNA 2.0, Menlo Park., CA), and cloned into plasmid pYD317. The plasmid T4PNK_pYD317 was used to transform BL21(DE3) cells. These cells were grown in a Braun 10 L fermenter on auto-induction media (Studies F. W. (2005) *Protein Expr. Purif.* 41:207-234) for 18 hours to a final OD of 21. Cells were harvested by centrifugation and to obtain 240 g of cell pellet. 40 g of cell pellet were resuspended in 500 ml Buffer A (50 mM Tris (pH 7.8), 300 mM KCl, 10 mM imidazole), lysed by homogenization, was clarified by centrifugation, and loaded onto a 35 mL Ni-IMAC column. The column was washed with 5 column volumes of Buffer A. Buffer A plus 0.5 mM BME, 300 mM imidazole, 0.1 μM ATP, and 10% glycerol (v/v) was used for elution. To prevent aggregation, PNK-containing fractions were immediately diluted 4× with Buffer A containing 20% glycerol. PNK-containing fractions were pooled and buffer exchanged into PNK storage buffer (20 mM Tris (pH 7.6), 100 mM KCl, 0.2 mM EDTA, 2 mM DTT, 50% glycerol) at a final concentration of 1.2 mg/mL.

tRNA-2',3'-cyclic phosphate (40 μM) was incubated at 37° C. with 50 μg/ml PNK in 50 mM MES (pH 5.5), 10 mM $MgCl_2$, 300 mM NaCl, and 0.1 mM EDTA for 1 hr leaving 2',3'-OH groups at the 3' terminus of the tRNA, followed by phenol:chloroform:isoamylalcohol extraction and buffer exchanged using a PD10 (GE health sciences) size exclusion column pre-equilibrated in 0.3 M sodium acetate (pH 5.2) to remove inorganic phosphate and excess phenol. tRNA was precipitated by addition of an equal volume isopropanol, incubation at −80° C. for 30 min, centrifuged for 30 min at 20,000×g, washed with 70% ethanol, centrifuged for 10 min at 20,000×g, air dried and resuspended in 0.1 mM sodium citrate (pH 6.4). tRNA was refolded by heating to 70° C., addition of 10 mM $MgCl_2$, and then slowly cooled to room temperature. tRNA concentration was determined using a NanoDrop 1000 spectrophotometer (Thermo Scientific) with $1A_{260}$=40 μg/mL, and confirmed by TBE/urea gel electrophoresis. Yields of ~2-10 mg of active, chargeable tRNA could be achieved from a 100 mL transcription reaction. *H. pylori* $tRNA^{Gln}$ was prepared similarly using an earlier iteration of this protocol with the following differences: tRNA concentration was 8.6 μM; in PNK reactions, PNK concentration was 0.020 mg/ml, EDTA was omitted, and 1 mM β-mercaptoethanol was added. The tRNA was resuspended in DEPC treated sterile water after purification.

Figure 7:
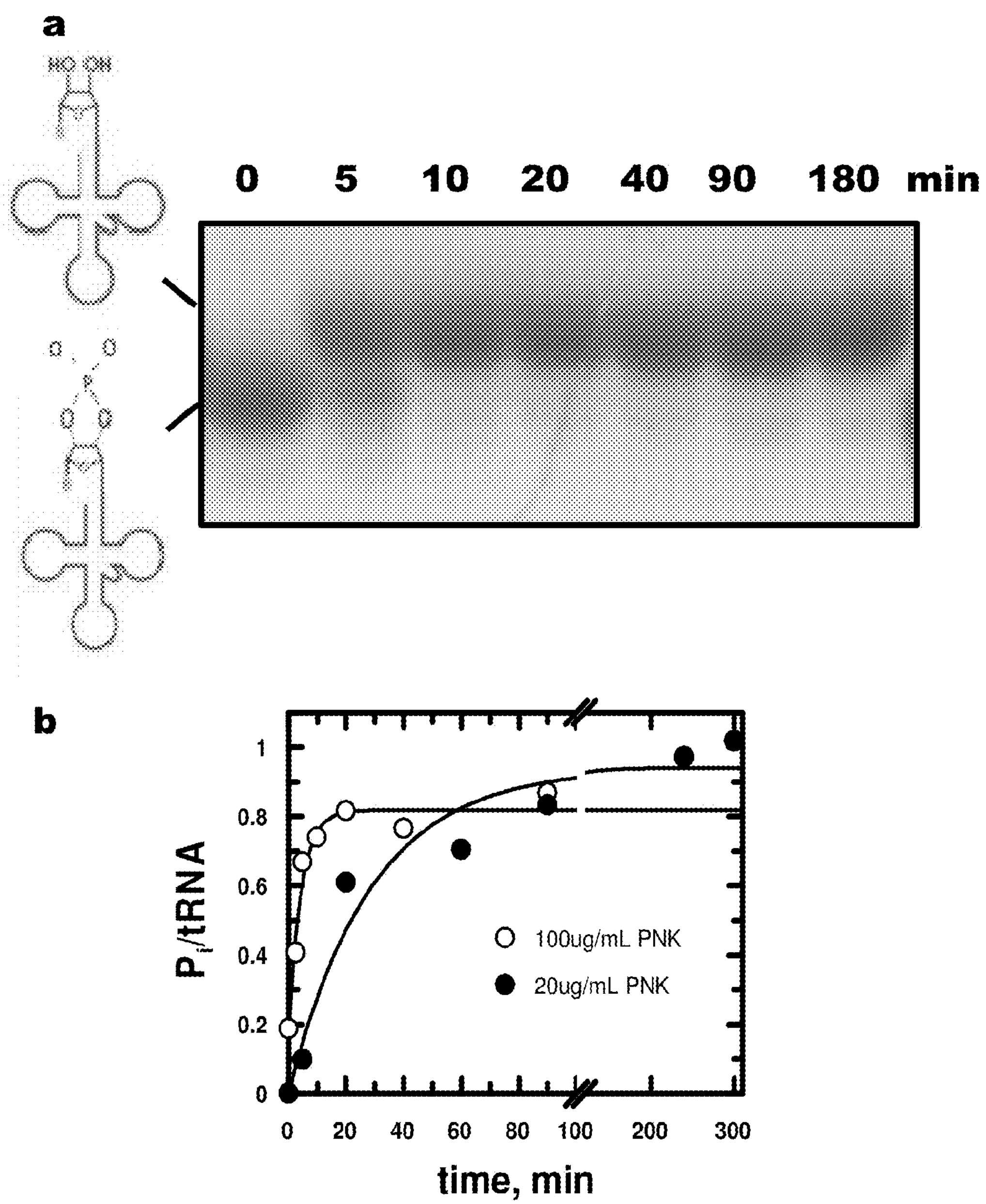
FIG. 7 shows the time dependence of the dephosphorylation of tRNA 2'-3'-cyclic phosphate by PNK treatment as measured by (a) separation of reactant and product using acid/urea gel electrophoresis or (b) using a malachite green phosphate release assay.

The extent of dephosphorylation was assayed by acid/urea gel electrophoresis and by phosphate release using a Malachite Green phosphate detection assay (R&D Systems, Inc). FIG. 7 shows that dephosphorylated tRNA has a reduced mobility in acid/urea gel electrophoresis (Bindereif, Schon, & Westhof (2005)). Aliquots containing 3 μg of dephosphorylated tRNA were diluted 2-fold in loading buffer (100 mM sodium acetate (pH 5.2), 7 M urea, 1 mg/ml bromophenol blue dye) and loaded on a 6.5% 19:1 acrylamide, 100 mM sodium acetate (pH 5.2), 7 M urea gel (40 cm×34 cm) and electrophoresed overnight at 40 W. Gels were stained using 0.06% methylene Blue, 0.5 M sodium acetate (pH 5.2) for 30 minutes and destained with deionized water. Both assays indicated essentially complete and quantitative dephosphorylation after 1 h.

Example 4

Recombinant Expression of an Aminoacyl-tRNA Synthetase

Vectors, Enzyme Expression, and Purification

The separate tRNA aminoacylation (charging) reactions illustrated by the last step in FIG. 2 require the use of an engineered aminoacyl-tRNA synthetase to aminoacylate isoaccepting tRNA molecules. This synthetase can be obtained by expressing a recombinant engineered synthetase as described in the examples below.

*E. coli* glutamyl-tRNA synthetase (GluRS) was cloned, expressed and purified by IMAC chromatography. The *E. coli* GluRS expression construct was transformed into BL21 (DE3) cells. Colonies were inoculated into 2 ml LB broth supplemented with 100 μg/ml ampicillin (LB-AMP) and grown to saturation at 37° C. This culture was diluted into 100 ml LB-AMP and grown to saturation at 37° C. This entire culture was used to inoculate 10 L of autoinduction media (Studier (2005), Protein Expr Purif.; 41, 207-34) supplemented with 100 μg/ml Ampicillin in a Bioflo 3000 fermentor. This culture was grown for 18 hours at 37° C. until it reached an OD of ±12. Cells were harvested in Sharples centrifuge and frozen at −80° C. 30 g of cell pellet was resuspend in 500 ml of GluRS Lysis Buffer (50 mM sodium phosphate (pH 8.0), 300 mM NaCl, 10 mM imidazole, 10% glycerol) and lysed by passage through an Avestin C55A homogenizer. Lysate was clarified by centrifugation in a JA-17 (Beckman) rotor at 40,000×g for 30 min. The supernatant was passed over a 30 ml $Ni^{2+}$ Sepharose 6 Fast Flow (GE Healthcare) column equilibrated in GluRS lysis buffer. The column was then washed with 15 column volumes of GluRS Wash Buffer (50 mM sodium phosphate pH 8.0; 300 mM sodium chloride; 20 mM imidazole; 10% glycerol), and eluted with 5 column volumes of GluRS Elution Buffer (50 mM sodium phosphate pH 8.0; 300 mM sodium chloride; 300 mM imidazole; 10% glycerol) as illustrated in FIG. 8*a*. Peak fractions were pooled, dialyzed twice into 2 L of 2×GluRS Storage Buffer (100 mM HEPES, pH 8.0; 40 mM sodium chloride; 1 mM dithiothreitol (DTT); 0.2 mM EDTA), and diluted 2-fold with 100% glycerol. Recovery was ~945 mg GluRS from 30 g of cell pellet. Protein was stored at −80° C. for extended periods of time and −20° C. once thawed.

*H. pylori* GluRS2 (ND) (also termed a non-discriminating (ND) synthetase) was cloned, expressed, and purified by IMAC as follows. The *H. pylori* GluRS2 (ND) expression construct was transformed into BL21 (DE3) cells and plated on two LB-AMP plates at 37° C. The next morning 10 ml LB was added to the plates and they were then scrapped with a sterile pipet to resuspend all colonies. The resuspension was added to 2 L of LB-AMP and grown at 37° C. In keeping with previous work (Skouloubris, Ribas de Pouplana et al. (2003) Proc Natl Acad Sci USA, 100, 11297-302), to avoid incorporation of glutamate in GluRS2(ND)'s glutamine codons as a result of its own expression, overexpression was induced with 1 mM isopropyl 13-D-thiogalactoside at $OD_{600}$~0.9 for only 30 min Cells were harvested by centrifugation at 4500 rpm for 30 min in a Sorvall RC-3B centrifuge, and frozen at −80° C. Cell pellet from 2 L of culture was resuspended in 25 ml lysis buffer (20 mM Tris, pH 8.5; 300 mM NaCl; 10% glycerol; 10 mM imidazole) supplemented with 250 μL bacterial protease inhibitor cocktail (Sigma). Cells were lysed by addition of lysozyme (to 1 mg/ml) and passage 10× through a 22 gauge blunt needle. Total lysate was clarified by centrifugation at 35,000×g for 30 min. Lysate was diluted 3× in lysis buffer then bound in batch mode for 10 minutes to 1 ml of IMAC High Performance Sepharose charged with $NiSO_4$ and equilibrated in lysis buffer. The resin was washed with 10 column volumes of lysis buffer supplemented with 0.5 mM DTT, and then eluted 5× with 1 ml GluRS2 (ND) Elution Buffer (Lysis Buffer supplemented with 300 mM imidazole and 0.5 mM DTT) as illustrated in FIG. 8*b*. Peak fractions were concentrated by Vivaspin 10 kD MWCO ultrafiltration. Preliminary dialysis of concentrated protein into 40 mM HEPES, pH 7.2, 0.2 mM EDTA, 1 mM DTT resulted in GluRS2 (ND) precipitation. Sodium chloride was added to resolubilize and protein was instead dialyzed into GluRS2 (ND) Storage Buffer (20 mM Tris, pH 8.5; 300 mM NaCl; 10% glycerol; 0.5 mM DTT; 0.1 mM EDTA). Protein was stored in small aliquots at −80° C. ~0.6 mg of GluRS2(ND) was recovered from the purification.

Figure 9:
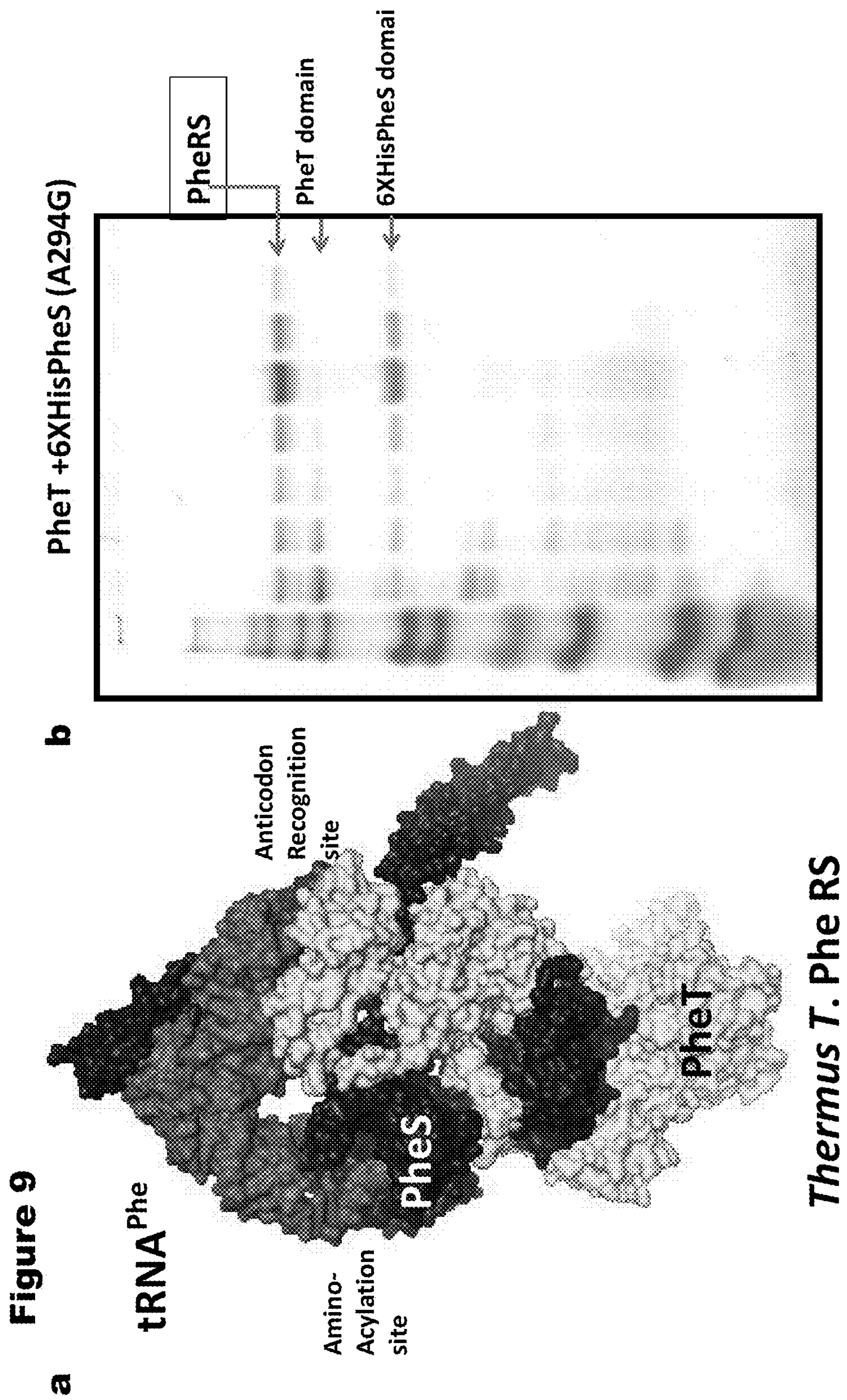
FIG. 9 shows (a) the dimeric structure of the homologous *T. thermophilus* PheRS illustrating the amino acid recognition site containing A294G and the anti-codon recognition site. (b) IMAC purification profile of cell-free produced PheRS (A294G) showing pull-down of the dimeric complex by the 6×His-tagged (SEQ ID NO:13) PheS(A294G) domain.

*E. coli* phenylalanyl-tRNA synthetase (PheRS) is an obligate dimer consisting of two subunits, PheS and PheT, as illustrated in FIG. 9*a* for the homologous enzyme from *T. thermophilis*. The mutation A294G was introduced in the *E. coli* PheS in order to increase the percent charging of non-native para-substituted phenylalanine analogs (Datta, Wang et al. (2002) *J Am Chem Soc,* 124, 5652-3) using a QuickChange Mutagenesis kit (Stratagene) and overlapping primers The resulting 6×His PheS(A294G) gene was subcloned into pET21(a) using Nde I to Sal I restriction sites. This plasmid was used to transform BL21(DE3) competent cells. Cells were grown overnight in auto-induction media yielding PheS(A294G) subunit in inclusion bodies. Cells were lysed by homogenization and the inclusion bodies were pelleted by centrifugation, completely resuspended in 6 M guanidine, then diluted with PBS to a final concentration of 2 M guanidine-HCl.

The PheT gene was amplified from *E. coli* genomic DNA using primers containing NdeI and XhoI restriction sites. The PCR fragment was subcloned into pET24(b), and expressed using the identical autoinduction media as PheS(A294G). In contrast to PheS(A294G), the expressed PheT subunit was soluble. Cells were lysed in Ni affinity purification load buffer: 50 mM NaPO4 buffer (pH 7.5), 300 mM NaCl, and 5 mM imidazole. The lysate was clarified, and then PheS (A294G) in 2 M guanidine-HCl was added slowly with stirring. Refolded PheRS was isolated by Ni affinity chromatography followed by size exclusion chromatography using an S100 size exclusion resin.

Alternatively, and more efficiently, PheRS(A294G) and variants in the anticodon recognition site of the PheT domain were produced by cell-free synthesis from independent PheS and PheT genes cloned into pYD317 as summarized in Table 1:

TABLE 1

Figure 10:
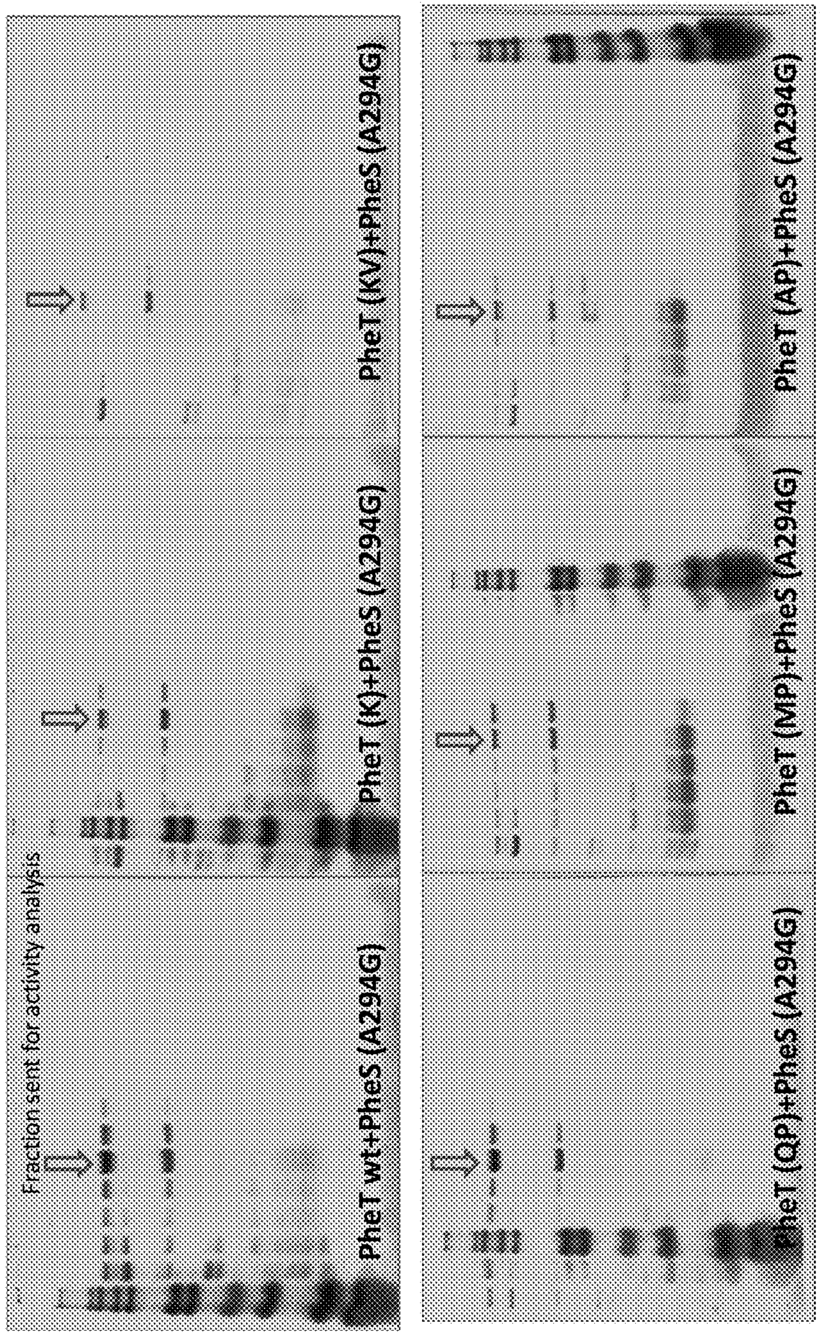
FIG. 10 shows the purification of several PheRS(A294G, A794X) variants produced by cell-free protein synthesis.

| PheT Variants in FIG. 10 | Corresponding Mutations |
| --- | --- |
| PheT MP | R794M R788P |
| PheT QP | R794Q R791P |
| PheT AP | R794A A791P |
| PheT K | R794K |
| PheT KV | R794K A15V |

Plasmids of pYD317 PheS(A294G) and pYD317 PheT variants were added to cell-free reactions simultaneously at a concentration of ug/mL. and cell-free synthesis was carried out for hrs. The heterodimeric protein variants were purified by IMAC is shown in FIG. 10 and can subsequently be used to charge isoaccepting tRNAs.

Example 5

Radioactive Methods for Monitoring tRNA Aminoacylation with nnAAs

The 3' terminal adenosine nucleotide of tRNAs was exchanged with $\alpha$-$^{32}$P-AMP using *E. coli* CCA nucleotidyl transferase enzyme as described (Ledoux & Uhlenbeck (2008), Methods, 44, 74-80). Reaction conditions are driven toward removal of the 3'-AMP using excess PPi, and then toward addition of AMP using PPiase. Active tRNA was incubated with CCA enzyme in 50 mM Glycine pH 9.0, 10 mM $MgCl_2$, 0.3 μM $\alpha$-$^{32}$P-ATP, 0.05 mM PPi for 5 min at 37° C. 1 μl of 10 μM CTP and 10 U/ml (1 Unit) of inorganic pyrophosphatase (yeast-Sigma) was added, and incubated for 2 min longer, then 1/10th volume of 3 M NaOAc pH 5.2 was added to each aliquot. The resulting 3'-end radiolabeled tRNA was diluted 1:5 with water and refolded prior to use.

Figure 12:
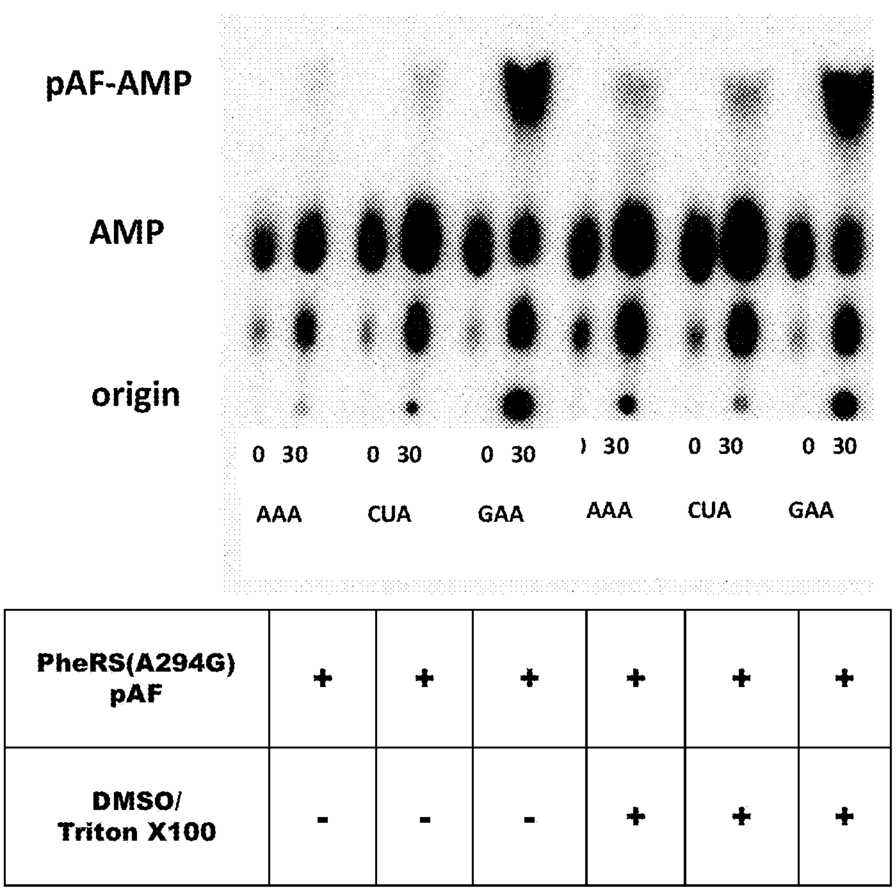
FIG. 12 shows percent para-acetyl Phe (pAF) aminoacylation analysis of pAF-tRNA$^{Phe}$ variants catalyzed by PheRS (A294G) under various conditions as measured by autoradiography using a end-labeled [$^{32}$P]-3' tRNA.

Aminoacylation of nnAAs onto $tRNA^{Phe}$ was performed using optimized conditions. The conditions for wild-type $tRNA_{GAA}^{Phe}$ aminoacylation were 50 mM Hepes pH 7.5, 40 mM KCl, 10 mM $MgCl_2$, 5 mM ATP, 8-40 μM $tRNA_{GAA}^{Phe}$, 10 mM DTT, 10-100 mM amino acid (Phe or para-acetyl Phenylalanine (pAF)), and 1-100 μM PheRS or PheRS A294G. End labeled tRNA reactions are digested with P1 nuclease for 20-60 min at room temperature and 1 μl is spotted on a pre-washed (water) PEI cellulose TLC plate and allowed to air dry. AMP is resolved from aa-AMP in acetic acid/1M $NH_4Cl$/$ddH_2O$ (5:10:85) as monitored by autoradiography using a Molecular Dynamics storage phosphor screen with a Storm 840 Phosphoimager (FIGS. 11 and 12). In contrast to the results shown in FIG. 11, Peterson and Uhlenbeck (Peterson and Uhlenbeck (1992) *Biochemistry,* 31, 10380-9) have shown that under limiting [$tRNA_{CUA}^{Phe}$], charging by phenylalanine is very inefficient.

The kinetics of $tRNA_{CUA}^{Phe}$ and $tRNA_{AAA}^{Phe}$ aminoacylation with pAF were monitored in 50 mM Hepes pH 8.1, 40 mM KCl, 75 mM $MgCl_2$, 5 mM ATP, 0.1% Triton X-100, 1.4 M DMSO, 25 U/μl Inorganic pyrophosphatase, 8-40 μM $tRNA_{CUA}^{Phe}$ or $tRNA_{AAA}^{Phe}$, 10 mM DTT, 10-100 mM pAF, and 1-100 μM PheRS or PheRS(A294G). FIG. 13 shows that pAF is efficiently charged to form pAF-$tRNA_{CUA}^{Phe}$, and pAF-$tRNA_{AAA}^{Phe}$ under the conditions of this reaction.

Figure 14:
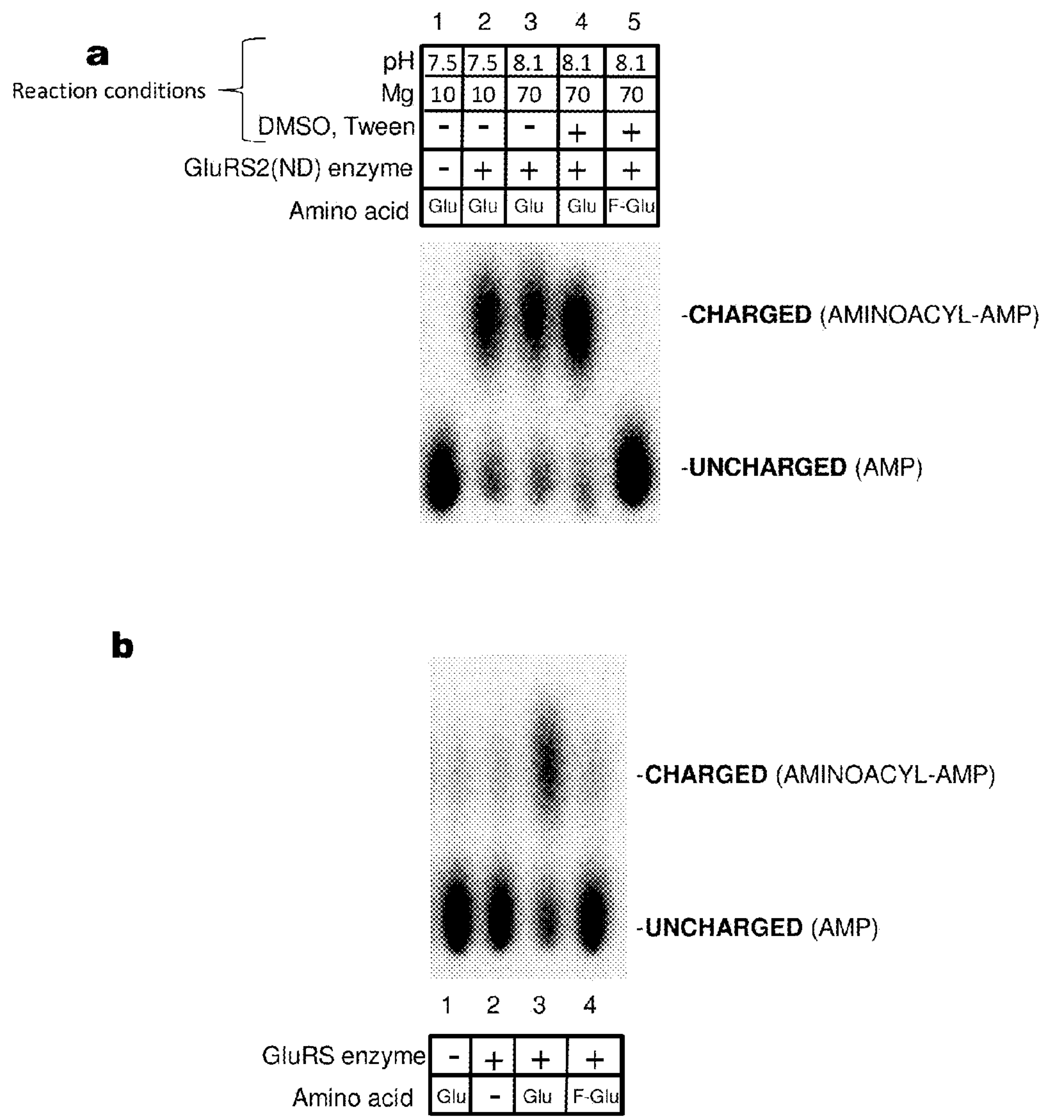
FIG. 14 shows that (a) *E. coli* GluRS can robustly aminoacylate tRNA$_{CUA}^{Phe}$ with cognate glutamate as measured using a [$^{32}$P]-3' tRNA end-labeling assay under optimized conditions. Mono-fluoroglutamate (F-Glu) AMP is not separated from [$^{32}$P]-AMP under these chromatographic conditions. (b) *H. pylori* GluRS2(ND) can aminoacylate *H. pylori* tRNA$_{CUC}^{Glu}$ with Glu and F-Glu, although F-Glu AMP is not separated from AMP under these chromatographic conditions.

We used high concentrations—18 μM each—of *E. coli* GluRS and $tRNA_{CUC}^{Glu}$ in the charging reactions. Normal charging conditions were: 10 μL reactions, 37° C. incubation for 30 min in 50 mM HEPES, pH 7.5; 10 mM $MgCl_2$; 10 mM DTT; 10 mM ATP; 10 mM glutamic acid, pH 7.5; 10 U/ml pyrophosphatase; and 1 μL of [$^{32}$P] end labeled $tRNA_{CUC}^{Glu}$ Reactions were quenched with 1 μL of 3 M sodium acetate. Encouragingly, with such high concentrations of tRNA and GluRS, we found that mutant $tRNA_{CUC}^{Glu}$ could be charged with cognate glutamate to 75% even with normal buffer conditions (FIG. 14*a*, lane 2). By changing the reaction pH to 8.1 and increasing $Mg^{2+}$ concentrations to 70 mM charging increased slightly to 77%. Further addition of dimethyl sulfoxide (DMSO) to 2.5 M and Tween-20 to 0.25% resulted in an additional increase to 84% charging (FIG. 14*a*, lane 4). Fluoro substituted glutamate charging onto wild type $tRNA^{Glu}$ could not be detected under the conditions of this assay (FIG. 14*a*, lane 5), due to the poor separation of fluoro substituted glutamate-AMP and AMP in the thin layer chromatography (Hartman, Josephson et al. (2007) *PLoS ONE,* 2, e972).

We also confirmed the activity of the purified *H. pylori* GluRS2(ND) (1.9 μM) using, *H. pylori* $tRNA^{Gln}$ 3.4 μM, pyrophosphatase 50 U/ml and 0.5 μL of [$^{32}$P] end labeled *H. pylori* $tRNA^{Gln}$ was included in each reaction. Similarly, no charging of mono-fluoro substituted glutamate was observed using this assay (FIG. 14*b*)

Example 6

Non-Radioactive Methods for Monitoring tRNA Aminoacylation with nnAAs

Non-radiolabeled $tRNA_{GAA}^{Phe}$, $tRNA_{CUA}^{Phe}$ and $tRNA_{AAA}^{Phe}$ were aminoacylated in 50 mM Hepes pH 7.5, 40 mM KCl, 10 mM $MgCl_2$, 5 mM ATP, 8-40 μM $tRNA_{GAA}^{Phe}$, 10 mM DTT, 10-100 mM amino acid (Phe or pAF), and 1-100 μM PheRS or PheRS A294G. The conditions for $tRNA_{CUA}^{Phe}$ and $tRNA_{AAA}^{Phe}$ aminoacylation were 50 mM Hepes pH 8.1, 40 mM KCl, 75 mM $MgCl_2$, 5 mM ATP, 0.1% Triton X-100, 1.4 M DMSO, 8-40 μM $tRNA_{AAA}^{Phe}$ or $tRNA_{CUA}^{Phe}$ 10 mM DTT, 10-100 mM pAF, and 1-100 μM PheRS or PheRS A294G. Reactions are incubated at 37° C. for 15 min and quenched with 2.5 volumes of 300 mM sodium acetate pH 5.5. The quenched sample was extracted with 25:24:1 phenol: chloroform:isoamyl alcohol pH 5.2 (Ambion), vortexed for 2 min, then centrifuged at 14,000×g for 10-30 min at 4° C. to separate the aqueous (tRNA) and organic phases (protein).

The aqueous phase (containing charged tRNA) was removed and added to a pre-equilibrated (300 mM NaOAc) G25 sephadex resin size exclusion column that separates based on the size of the molecule. The eluant was mixed with 2.5 volumes of 100% ethanol and incubated at −80° C. for 15-30 minutes and centrifuged at ~14,000×g for 30-45 minutes. The pelleted aminoacylated tRNA is stored at −80° C. or resuspended in a slightly acidic buffer for injection into the HPLC and/or use in cell-free synthesis reactions.

Figure 15:
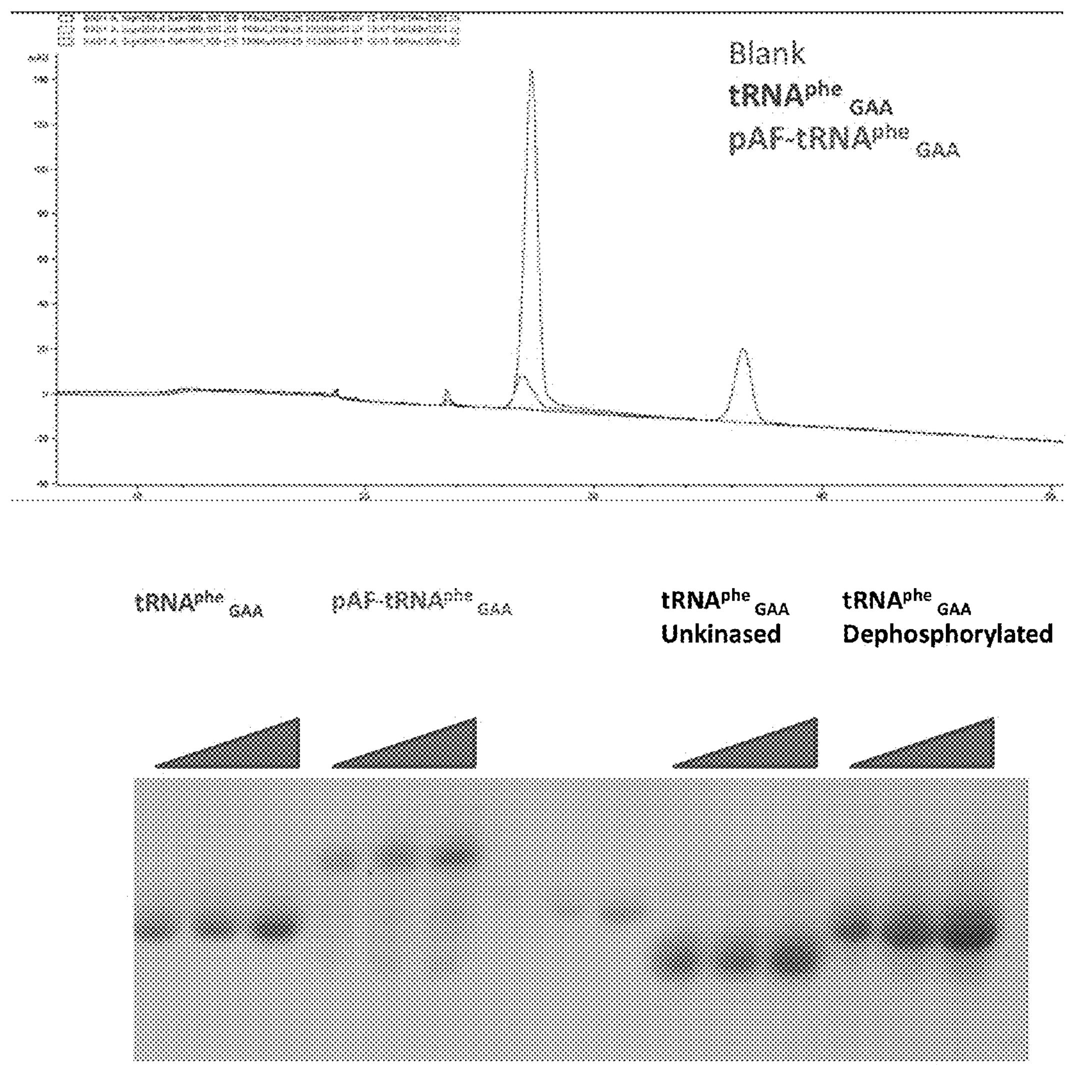
FIG. 15 shows (a) the separation of aminoacylated pAF-tRNA$_{GAA}^{Phe}$ from tRNA$_{GAA}^{Phe}$ using hydrophobic interaction chromatography, and (b) the chromatographic mobility of aminoacylated pAF-tRNA$_{GAA}^{Phe}$, tRNA$_{GAA}^{Phe}$, and tRNA$_{GAA}^{Phe}$ 2',3' cyclic phosphate by acid-urea gel electrophoresis.

Aminoacylation of non-radiolabeled $tRNA_{GAA}^{Phe}$, $tRNA_{CUA}^{Phe}$ and $tRNA_{AAA}^{Phe}$ was monitored by HPLC hydrophobic interaction chromatography (HIC) that resolved the aminoacylated and unaminoacylated moieties of tRNA as shown in FIG. 15 & FIG. 16. The HPLC C5 column was equilibrated in buffer A (50 mM potassium phosphate and 1.5 M ammonium sulfate pH 5.7), then 1-10 μg of pelleted aminoacylated tRNA mixed with 100 μl of 2× buffer A was injected and separated with a gradient from buffer A to buffer B (50 mM potassium phosphate and 5% isopropanol) over 50 minutes. The fraction of aminoacylated tRNA determined by peak area showed good agreement with the fraction determined using [$^{32}$P]-end labeled tRNA as in FIG. 13 for reactions run under the same conditions.

Alternatively, $tRNA_{CAC}^{Glu}$ charged using *E. coli* GluRS to aminoacylate with mono-fluoroglutamate or pAF-$tRNA_{GAA}$ and $tRNA_{GAA}$ (FIG. 15) were separated using acid/urea polyacrylamide 40 cm×34 cm gel electrophoresis. For charging $tRNA_{CAC}^{Glu}$ reaction conditions were: 12.5 μL reactions, 37° C. incubation for 30 minutes in 50 mM HEPES, pH 8.1; 70 mM $MgCl_2$; 10 mM DTT; 10 mM ATP; 10 mM amino acid, pH 8.1; 16.6 U/ml pyrophosphatase. (To assure absence of RNAse in charging reactions, prior to tRNA addition the buffer was ultrafiltered through a 3000 Dalton molecular weight cut-off membrane (Microsep 3K Omega; Pall lifesciences). Reactions were quenched with 1.25 μL of 3M sodium acetate, diluted 2-fold in loading buffer (100 mM sodium acetate pH 5.2; 7 M urea; 1 mg/ml bromophenol blue dye) and loaded on 6.5% 19:1 acrylamide; 100 mM sodium acetate, pH 5.2; 7 M urea gels and electrophoresed overnight at 40 W. Gels were stained using 0.18% Methylene Blue, 0.5 M sodium acetate, pH 5.2 for 30 minutes and destained with deionized water. Charging of wild type $tRNA^{Glu}$ (Chemical Block, Moscow, Russia) or in vitro transcribed $tRNA_{CUC}^{Glu}$ with cognate glutamate or non-native fluoroglutamate could be observed up to 70% (FIG. 17).

Example 7

Cell-Free Protein Synthesis to Manipulate nnAA Incorporation

Cell-free extracts or lysates were generated to maximize ribosome yield using rapid growth of high cell density fermentations of *E. coli* strain KGK10 (Knapp, Goerke et al. (2007) *Biotechnol Bioeng,* 97, 901-8), essentially as described by Liu et al. (Liu, Zawada et al. (2005) *Biotechnol Prog,* 21, 460-5) DL-dithiothreitol was not added to the cell lysate following homogenization. A modified "run-off procedure" was used to prepare the cell-free extract. Fermentation volume to generate sufficient cell-free extract was typically 2.5× the desired cell-free reaction volume. To inactivate the reducing activity of the cell extract, iodoacetamide (IAM) at various concentrations was added as previously described (Yang, Kanter et al. (2004) *Biotechnol Prog,* 20, 1689-96). Gene expression was under the control of the T7 promoter. In order to facilitate translation initiation, genes were synthesized (DNA 2.0, Menlo Park, Calif.) with synonymous codons at the 5' end of the gene with ATG start codon (N-terminal methionine residue) optimized for mRNA instability as measured by mRNA $\Delta G_{fold}$ in the −6 to +37 positions (Kudla, Murray et al. (2009) *Science,* 324, 255-258) and rare codons were replaced.

Cell-free reactions were run at 30° C. containing 8 mM magnesium glutamate, 10 mM ammonium glutamate, 130 mM potassium glutamate, 35 mM sodium pyruvate, 1.2 mM AMP, 0.86 mM each of GMP, UMP, & CMP, 2 mM amino acids (1 mM for tyrosine), 4 mM sodium oxalate, 1 mM putrescine, 1.5 mM spermidine, 15 mM potassium phosphate, 100 nM T7 RNA polymerase, 2-50 nM DNA template(s), 1-10 μM *E. coli* DsbC, and 24-30% (v/v) IAM-treated cell-free extract. The redox potential was manipulated by the addition of reduced (GSH) and oxidized (GSSG) glutathione to a total concentration of ±5 mM. The initial redox potential was calculated using the Nernst equation with $E^0$=−205 mV as the standard potential of the GSH/GSSG couple at 30° C. and pH 7 (Wunderlich and Glockshuber (1993) *Protein Science,* 2, 717-726).

Figure 18:
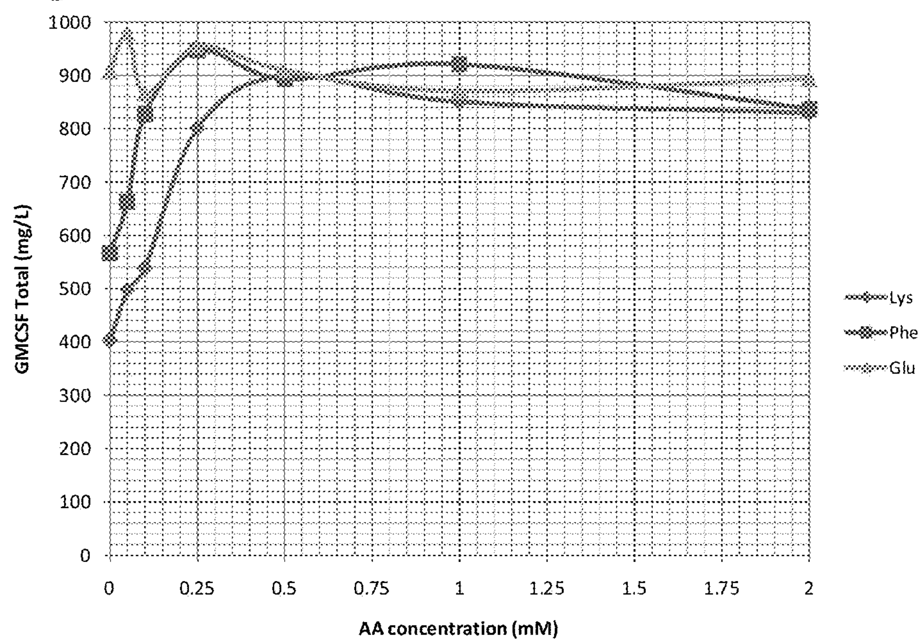
FIG. 18 shows cell-free synthesis yields of GMCSF as function of the concentration of added lysine, phenylalanine, or glutamic acid to the extract.

GMCSF was expressed in the cell-free protein synthesis system at 30° C. for 6 hours. FIG. 18 illustrates how the concentration of added amino acids, Lys and Phe, but not Glu, may be manipulated in the cell-free reaction to affect protein synthesis.

Example 8

Depletion of an Endogenous Aminoacyl-tRNA Synthetase

The genomic copy of glutamate-tRNA synthetase (gltX) was tagged with a C-terminal FLAG-tag in order to remove the synthetase activity using FLAG-tag affinity chromatography while maintaining the enzyme activity for preparation of the cell-extract prepared from *E. coli* KGK10. Gene insertion was carried out using Quick & Easy *E. coli* Gene Deletion Kit (Cat. No. K006) from GENE BRIDGES (Heidelberg, Germany) according to the protocol suggested by the manufacturer. A 708-FLPecm$^R$ expression plasmid (A105, GENE BRIDGES) was used to eliminate the selection marker from *E. coli* chromosome. The DNA insertion cassette was amplified by PCR extension using AccuPrime pfx SuperMix (Invitrogen) according to the protocol suggested by the manufacturer. DNA template was FTR-PGK-gb2-neo-FRT template DNA from Quick &_Easy *E._coli* Gene Deletion Kit.

Primers included:

```
                                   (SEQ ID NO: 14)
5'GCGTATCAACAAAGCGCTGGATTTTATTGCTGAACGCGAAAATCAGCA
GGGTGGCGACTACAAAGATGACGATGACAAATAAAATTAACCCTCACTAA
AGGGCGG3'
and
                                   (SEQ ID NO: 15)
5'AGGGATTATCGGATTGTTACAACGCTTAGGGATTCGCGATAGCAAATA
ATTAATACGACTCACTATAGGGCTCG3'
```

PCR fragments were purified with QIAGEN DNA purification kit before transforming *E. coli* KGK10 by electroporation. The DNA fragment including 3' end and downstream of gltX was amplified from chromosome DNA of KGK10ΔgltX::gltX-Flag using primers 5'GTTCAACACCGACAAGCTGCTGTGGCTG3' (SEQ ID NO:16) and 5' GCGGGAAGGGATTATCGGATTGTTACAACGC3' (SEQ ID NO:17). Flag-tag encoding sequence was confirmed by using a primer, 5'GATTACTGACTGGACCGCTG3' (SEQ ID NO:18).

First, primers were designed for PCR amplification the DNA fragment containing the Flag-tag encoding sequence at 3' end of gltX. The Flag-tag sequence DYKDDDDK (SEQ ID NO:19) was connected to the C-terminus of glutamate-tRNA synthetase through a dipeptide GG. The tag peptide sequence was back translated to DNA sequence, 5'GGGTGGCGACTACAAAGATGACGATGACAAA3' (SEQ ID NO:20). A stop codon TAA was added just behind the FLAG-tag encoding sequence. The forward primer included a 50 Nt homology sequence that encoded the C-terminus of glutamate—tRNA synthetase (G1uRS) at 5' end, the Flag-tag sequence in the middle, and the amplifying sequence AATTAACCCTCACTAAAGGGCGG-(SEQ ID NO:21) at the 3' end. The backward primer was designed by connecting the amplifying sequence TAATACGACTCACTATAGGGCTCG (SEQ ID NO:22) to a 50 Nt homology sequence which is located downstream of gltX gene. Second, the linear fragment for FLAG-tag sequence insertion was amplified and transformed into KGK10 to replace a 441 by sequence downstream of gltX. Flag-tag insertion mutants were selected by kanamycin resistance marker which was inserted to the genomic DNA of KGK10. Then, the kanamycin resistance marker for selection was eliminated using 708-FLPecm$^R$ expression plasmid-. Finally, the FLAG-tag encoding sequence was confirmed by sequencing the PCR fragment which was amplified from the mutant KGK10ΔgltX::gltX-Flag. A DNA sequence, 5'GGGTGGCGACTACAAAGATGACGATGACAAA3' (SEQ ID NO:23), was attached to the 3' end of the gltX gene in the KGK10 chromosome. This fragment encodes the amino acid sequence GGDYKDDDDK (SEQ ID NO:24), two Gly residues and a FLAG-tag. Removal of the FLAG-tagged GluRS protein from the cell-free extract is achieved by passing the extract over anti-FLAG M2 magnetic beads (Sigma cat #M8823) and removing the beads.

Example 9

Depletion of Endogenous aaRS Activity Using Active Site Directed Inhibitors Phe- and Glu-sulfamoyladenosine (Phe-SA & Glu-SA)

Figure 19:
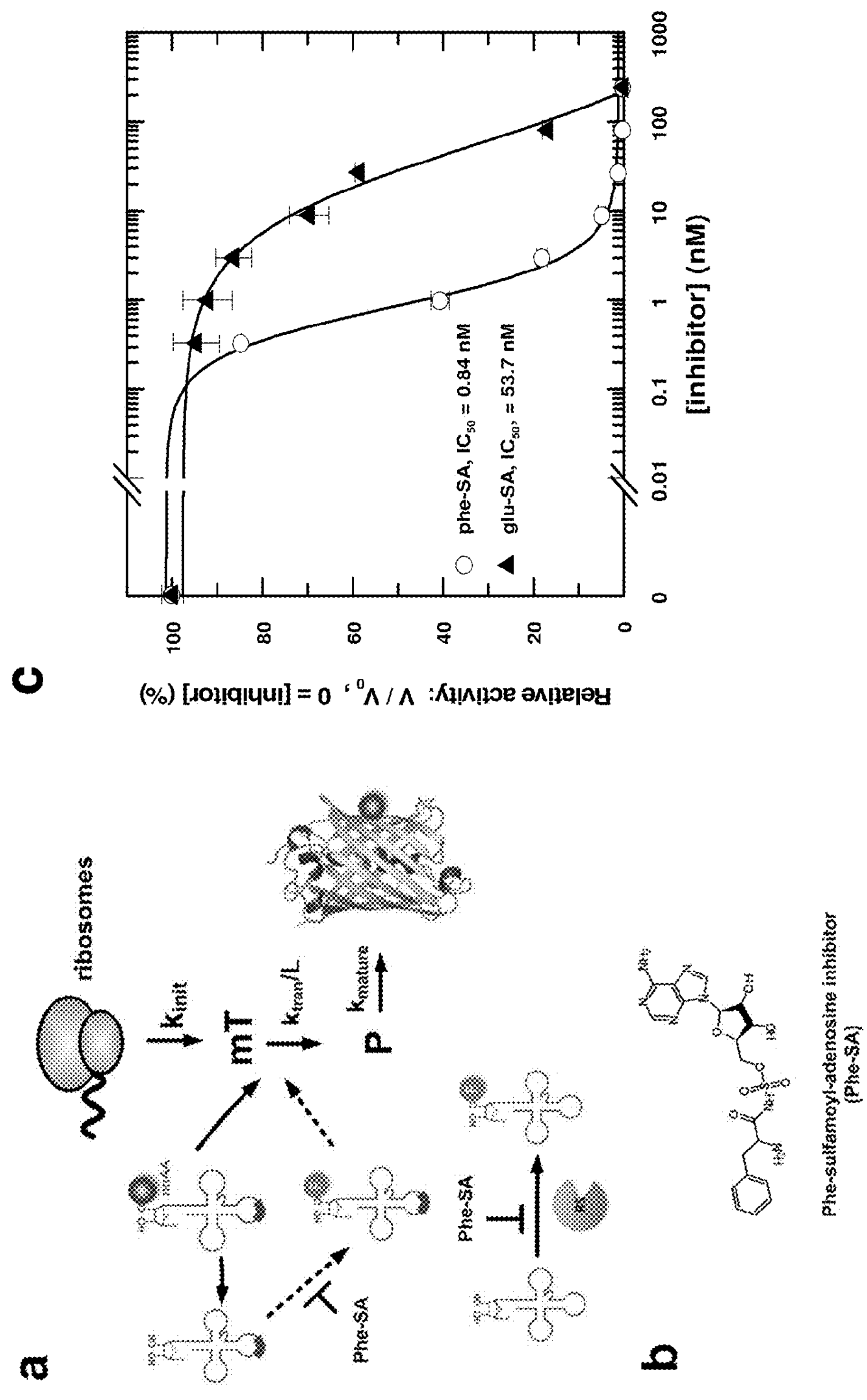
FIG. 19 shows (a) a diagram of the species involved in non-native amino acid incorporation into fluorescent turboGFP in the cell-free synthesis reaction, including background recharging of engineered isoaccepting tRNA by endogenous *E. coli* PheRS, (b) the chemical structure of an active-site directed inhibitor of PheRS, 5'-O—[N-(Phenylalanyl) sulfamoyl]adenosine, Phe-SA, and (c) the determination of $IC_{50}$ for inhibition of the rate of cell-free synthesis of turboGFP as a function of added inhibitors Phe-SA ($IC_{50}$=0.8 nM) or Glu-SA ($IC_{50}$=54 nM).

FIG. 19 illustrates how the reactivity of added isoaccepting charged nnAA-tRNAs added to the cell-free reaction can be modulated using active site directed inhibitors to limit the background recharging of the added isoaccepting tRNA.

The 5'-O—[N-(aminoacyl)sulfamoyl]adenosine inhibitor Phe-SA (FIG. 19*b*) was synthesized as follows: to a solution of alcohol (7 g, 17.03 mmol, 1.0 eq) in DMAC (70 mL) at 0° C. was added DIEA (10.62 mL, 59.61 mmol, 4.0 eq) and sulfamoyl chloride (4 eq) and the reaction mixture was stirred at room temperature for 15 h. The reaction mixture was diluted with ethyl acetate (300 mL) and washed with water (4×50 mL). The organic layer was dried over $MgSO_4$, evaporated and purified by column chromatography (DCM to 20% MeOH in DCM) to give the activated sulfamate (4.5 g, 9.18 mmol, 54% yield) To a solution of sulfamate (2.0 g, 4.07 mmole, 1 eq), DCC (0.841 g, 4.07 mmol, 1 eq), DMAP (050 g, 4.07 mmol, 1.0 eq) in DCM (45 mL) was added Boc-Phe-OH (1.1 g, 4.07 mmol, 1 eq) and the reaction mixture was stirred at room temperature for 10 h. The reaction mixture was diluted with ethyl acetate (450 mL), washed with saturated aqueous $NaHCO_3$, water, brine, dried over $MgSO_4$, and evaporated. The crude product was dissolved in MeOH/n-butylamine (30 mL/30 mL) and stirred at room temperature for 3 h. The solvents were evaporated and the crude product was purified by flash chromatography (EtOAc to 10% MeOH/EtOAc) to give the Phe-SA inhibitor (0.90 g, 1.4 mmol, 35% yield)

Figure 20:
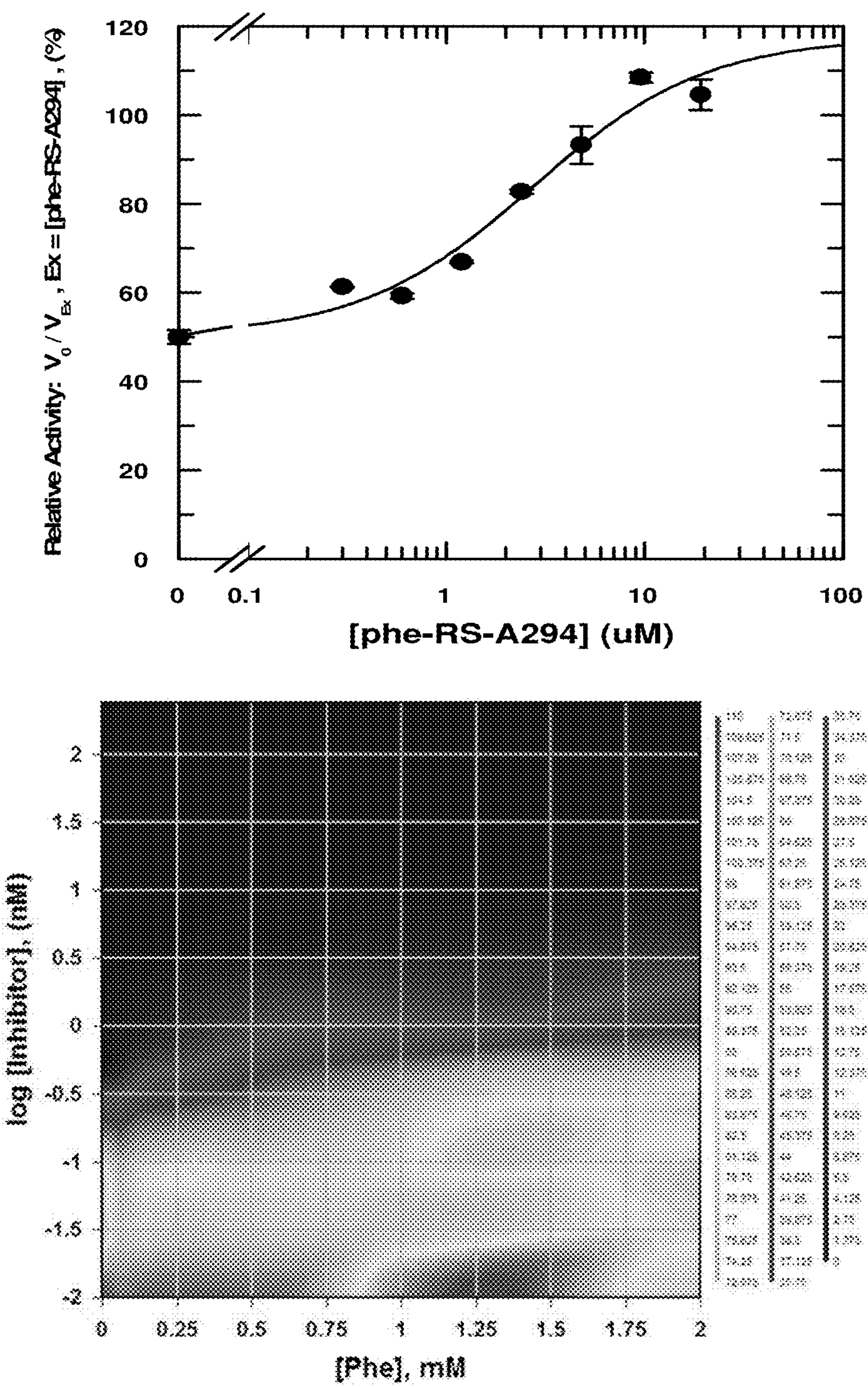
FIG. 20 shows a response surface describing the relationship between added Phe amino acid and [Phe-SA] inhibitor on the rate of turboGFP cell-free synthesis

The effects of 5'-O—[N-(aminoacyl)sulfamoyl]adenosine inhibitors (Phe-SA and Glu-SA) in cell-free synthesis of a GFP reporter protein, turboGFP are illustrated in FIG. 19*c*. Cell-free synthesis reactions at 30° C. were monitored by fluorescence ($\lambda_{Ex}$=476 nm and $\lambda_{Em}$=490 nm). with an adhesive cover (VWR, 9503130) in a Molecular Devices SpectraMaxM5 plate reader for 5 h. Aminoacyl synthetase inhibitors Phe-SA and Glu-SA (Integrated DNA Technologies, Iowa) were serially diluted 3-fold in DEPC-water from stock solutions in TE buffer (Invitrogen, 12090) and transferred to a 96-well V-bottom polypropylene plate (Greiner Bio-One, 651207). The cell-free reaction mix was immediately added to the microplate with inhibitor for a 25 μL final reaction volume. The maximal rate of fluorescence change ($V_0$ (RFU/sec)=no inhibitor, V=in the presence of inhibitor) were determined and the percent relative activity determined as a function of added inhibitor concentration as shown. Importantly, these inhibitors are competitively specific to their respective aminoacyl tRNA synthetases (PheRS and GluRS), as turboGFP fluorescence activity in the presence of 1 nM Phe-SA inhibitor (~50% activity) can be completely restored with the addition of >10 μM PheRS(A294G) as shown in FIG. 20. Surface response analysis of GFP activity as a function of varying both [Phe-SA] and added L-phenylalanine is consistent with the competitive and specific nature of the Phe-SA inhibition.

Example 10

Incorporation of Para-Acetyl Phenylalanine (pAF) into TurboGFP Y50TAG

Figure 21:
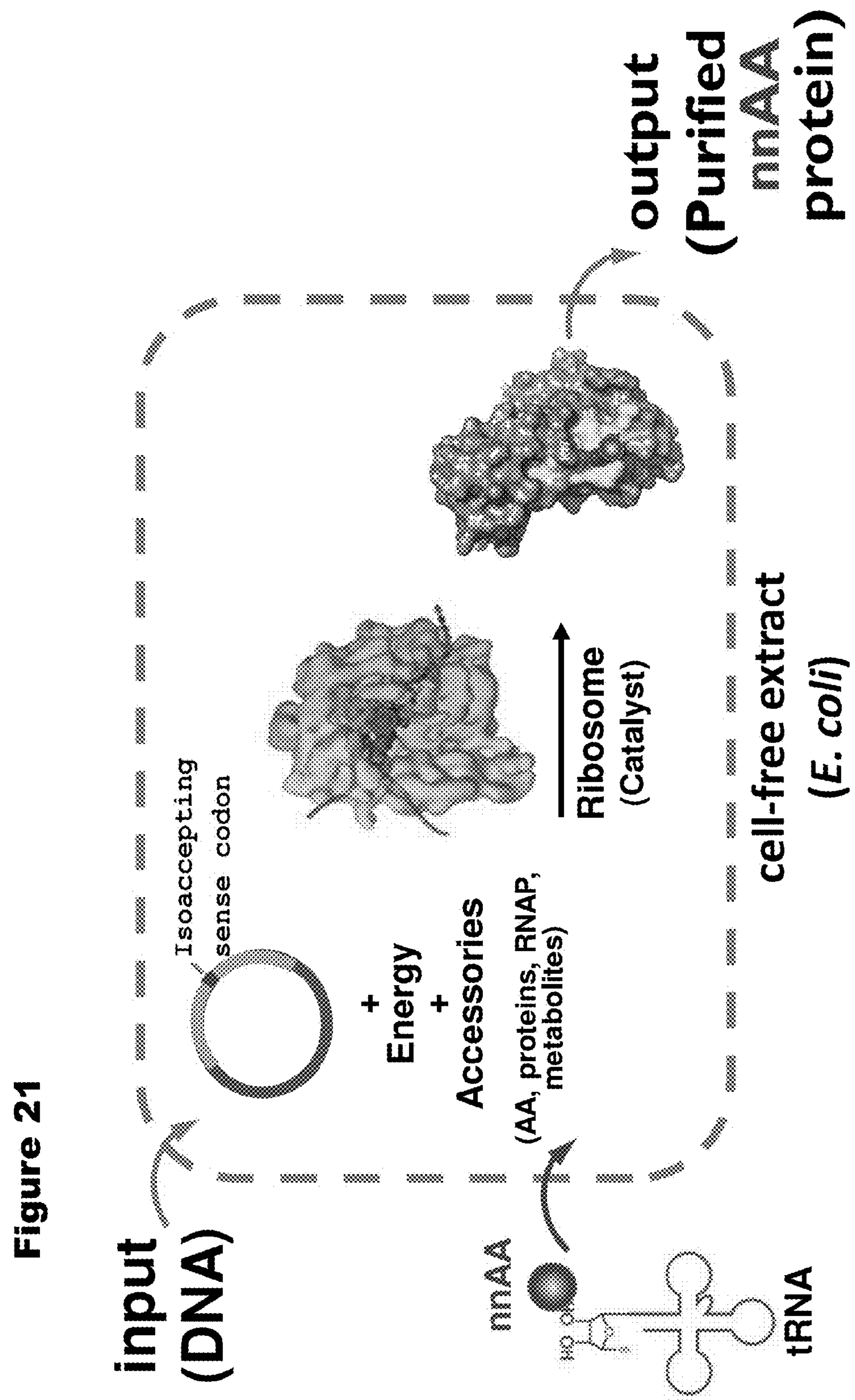
FIG. 21 shows a schematic diagram illustrating monocharging incorporation.

To control and optimize the cell-free synthesis of proteins containing non-native amino acids (nnAAs) (FIG. 21) we aimed to establish a quantitative framework that describes the kinetics and thermodynamics of individual steps in the overall process (cf FIG. 19*a*). Such a framework provides insights into the functions and mechanisms of each participant in the process and serves as a foundation for in-depth analyses and optimization of the cell-free incorporation of nnAAs into proteins.

Figure 22:
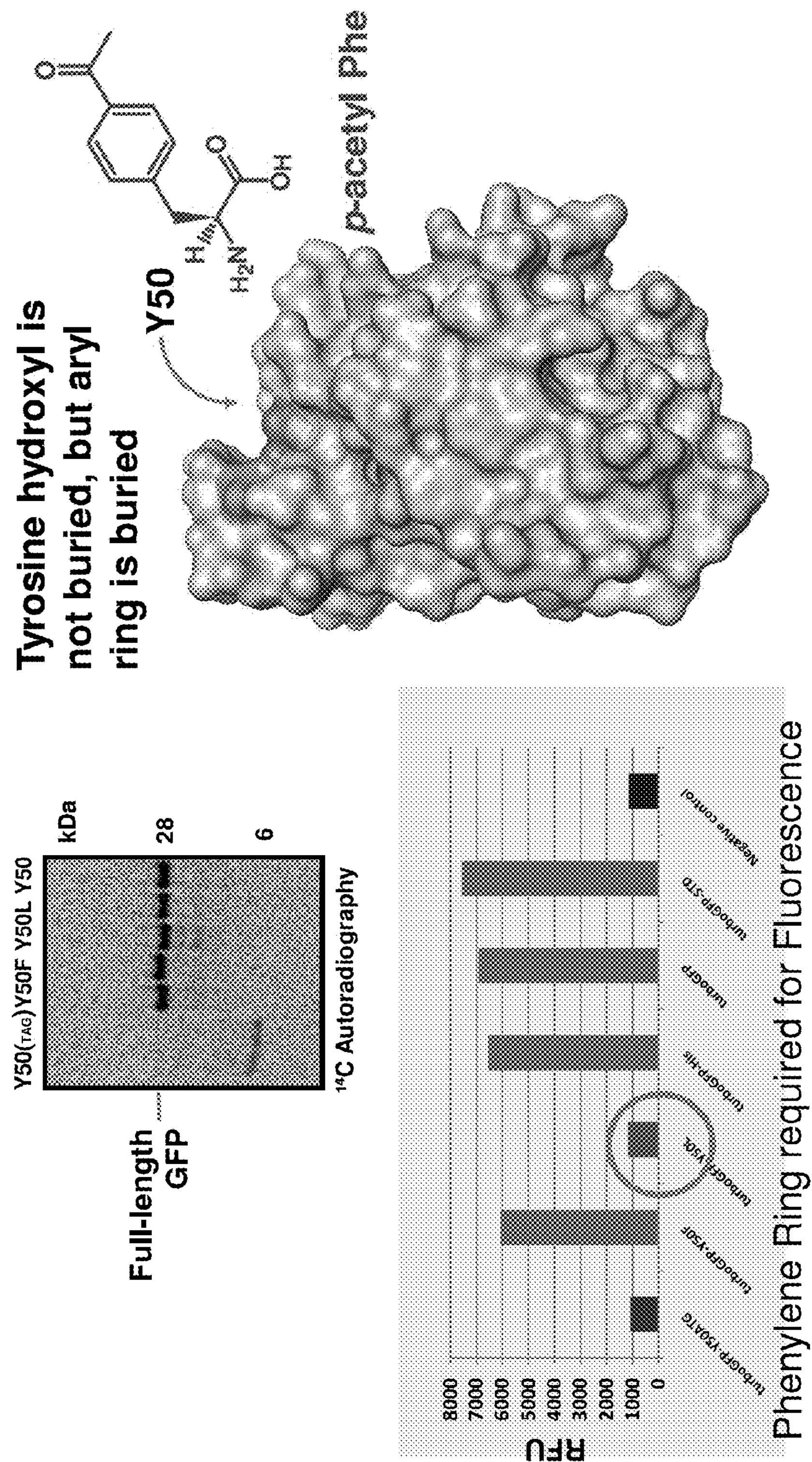
FIG. 22 illustrates the salient features of the turboGFP Y50TAG amber suppressor protein used to establish incorporation of para-acetyl phenylalanine (pAF) at position 50.

We constructed and analyzed a minimal kinetic model (cf FIG. 19) based on the cell-free synthesis of the green fluorescent protein from Anthropoda, turboGFP (Evdokimov, Pokross et al. (2006) *EMBO Rep,* 7, 1006-12). An amber (UAG) codon was introduced at position 50 in the protein sequence, yielding plasmid turboGFP Y50TAG (FIG. 22). In the absence of added suppressor tRNA, only the expected 6 kD truncated protein is synthesized.

Figure 23:
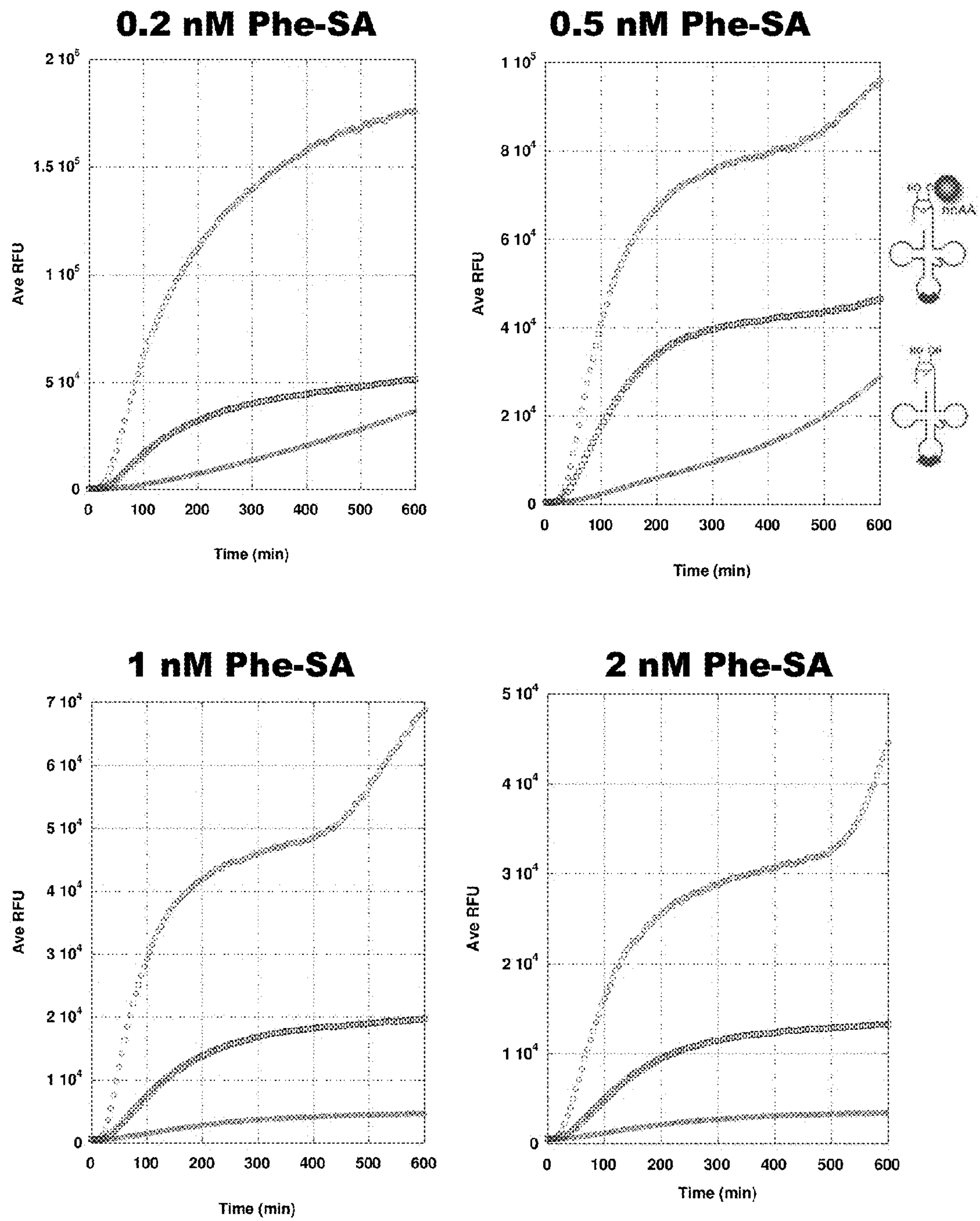
FIG. 23 shows the time course for cell-free synthesis of turboGFPY50TAG as a fluorescent reporter for suppression of an amber (UAG) codon positioned upstream of the GFP chromophore, in the presence of varying concentrations of Phe-SA inhibitor. Either ~20 μM uncharged tRNA$_{CUA}^{Phe}$ (◇) or ca. 70% charged pAF-tRNA$_{CUA}^{Phe}$ (€) were added to the reaction at time zero. (●) turboGFPY50 control.

The kinetics of the cell-free synthesis of fluorescent turboGFP in microtiter plate format was monitored by fluorescence ($\lambda_{Ex}$=476 nm and $\lambda_{Em}$=490 nm) with an adhesive cover (VWR, 9503130) in a Molecular Devices SpectraMax M5 plate reader for 5 h. A positive control reaction using turboGFP plasmid (without the UAG stop codon) was used as a positive control. Reactions containing turboGFP Y50TAG plasmid were also run without added tRNA to ensure no fluorescence was detected in the absence of exogeonously added tRNA (negative control). The absence of fluorescent signal is consistent with the ca. 6 kD truncated product previously observed (cf FIG. 22). In the absence of added Phe-SA inhibition, uncharged $tRNA_{CUA}^{Phe}$, suppressed the amber codon in turboGFPY50TAG, although less efficiently than added pAF-$tRNA_{CUA}^{Phe}$, suggesting that it was recognized and aminoacylated by one of the endogenous aaRS in the cell-free extract. To determine if PheRS was responsible for recharging of the exogenously added $tRNA_{CUA}^{Phe}$, the suppression of the amber codon using UAG-specific suppressor *E. coli* phenylalanine tRNA charged with p-acetyl phenylalanine (pAF), pAF-$tRNA_{CUA}^{Phe}$, was measured in the presence of various concentrations of Phe-SA inhibitor, to modulate the endogenous activity of PheRS (FIG. 23). A maximal incorporation of pAF into turboGFPY50TAG, 10× larger than with added $tRNA_{CUA}^{Phe}$ alone, was observed at an inhibitor concentration close to the previously determined $IC_{50}$ of Phe-SA (FIG. 19*c*). The inhibitor begins to lose its effectiveness after 7-8 h.

We conclude that incorporation of pAF into turboGFP achieves relatively high yields of protein while recharging of $tRNA_{CUA}^{Phe}$, as illustrated in FIG. 19*a*, is greatly reduced. These results show that cell-free synthesis can be used for the efficient synthesis of proteins containing site-specific nnAAs (cf FIG. 21) by adding exogenously charged nnAA-tRNA moieties, while controlling endogenous synthetase activity.

Example 11

Figure 24:
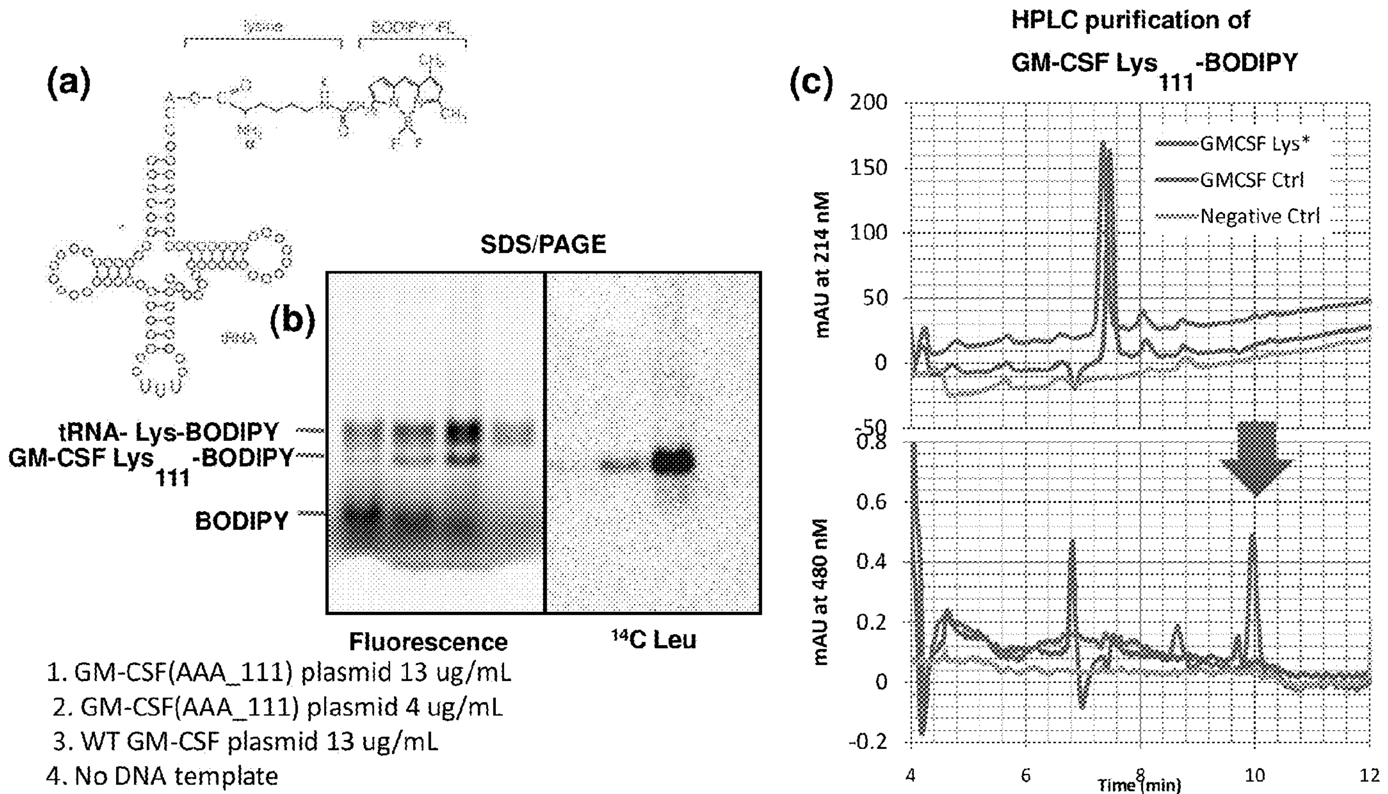
FIG. 24 shows (a) the structure of the BODIPYLys-tRNA$_{UUU}^{Lys}$, (b) SDS PAGE analysis of cell-free reactions carried out in the presence of BODIPYLys-tRNA$_{UUU}^{Lys}$, and (c) reversed-phase HPLC purification of the fluorescent protein synthesis reaction product.

Incorporation of a Fluorescent Tag into Proteins via BODIPYLys-$tRNA_{UUU}^{Lys}$ To demonstrate the feasibility of incorporation of a fluorescent tag into proteins, epsilon-labeled BODIPY-FL lysl-tRNA, BODIPYLys-$tRNA_{UUU}^{Lys}$, was added to the cell-free reaction containing a plasmid for rhGM-CSF with a single AAA codon at position 111 (FIG. 24). The cell-free reactions contained 8 mM magnesium glutamate, 10 mM ammonium glutamate, 130 mM potassium glutamate, 35 mM sodium pyruvate, 1.2 mM AMP, 0.86 mM each of GMP, UMP, & CMP, 2 mM amino acids (1 mM for tyrosine), 4 mM sodium oxalate, 1 mM putrescine, 1.5 mM spermidine, 15 mM potassium phosphate, 100 nM T7 RNA polymerase, 2-50 nM DNA template(s), 1-10 μM *E. coli* DsbC, and 24% (v/v) IAM-treated cell-free extract containing 2 μL BODIPYLys $tRNA_{UUU}^{Lys}$, (FluoroTect GreenLys Promega) per 50 μL cell-free reaction. As a control the cell-free reaction with no plasmid in the absence and presence of BODIPYLys-$tRNA_{UUU}^{Lys}$, were conducted in parallel. Proteins produced were monitored by incorporation of l-[U-$^{14}$C]-leucine (300 μCi/μmole; GE Life Sciences, NJ) by measuring the TCA-precipitable soluble and total protein. Cell-free reactions were incubated in 96-well V-bottom polystyrene microtiter plates (Greiner, Germany) at 30° C. with shaking Aliquots (5 μL) of total protein, or soluble protein from samples centrifuged at 6100×g for 10 min at 4° C. to remove insoluble protein aggregates, were blotted onto prewetted polyvinylidene fluoride (PVDF) filter plates (Millipore, Billerica, Mass.). The dried plates were washed three times with 200 μL of 5% TCA, followed by 100 μL of absolute ethanol. Optiphase scintillation cocktail (Perkin-Elmer, Waltham, Mass.) was added to a volume of 50 μL, and $^{14}$C radioactivity was measured in a Wallac 1450 Microbeta Plus counter (Perkin-Elmer). An aliquot of 3 μL of each soluble cell-free reaction was loaded on 12% Bis-Tris SDS-PAGE and the gel was scanned after electrophoresis using a Storm 840 Imager (GE healthcare) to monitor both radioactive counts and fluorescence, indicating nnAA incorporation. As shown in FIG. 24, the background fluorescence from the fluorescent tRNA conjugate migrates between 11 kD and 21 kD. The fluorescence of labeled GMCSF comigrates with control radioactively labeled GM-CSF, indicating the fluorescent BODIPY is introduced into the protein by the addition of BODIPYLys-$tRNA_{UUU}^{Lys}$ to the cell-free reaction. The product of a cell-free reaction in the presence of BODIPYLys-$tRNA_{UUU}^{Lys}$ run a 250 μL scale was purified using reversed phase HPLC (ZORBAX 300SB-C8 5 μm, 4.6×250 mm, Agilent) with gradient elution (buffer A: 100 mM triethylammonium acetate, pH 7.0; buffer B: 70% acetonitrile, 100 mM triethylammonium acetate, pH 7.0) and monitored at both 214 nm and 480 nm (to detect fluorescent BODIPY incorporation), as shown in FIG. 24.

Example 12

Incorporation of pAF into rhGM-CSF

Figure 25:
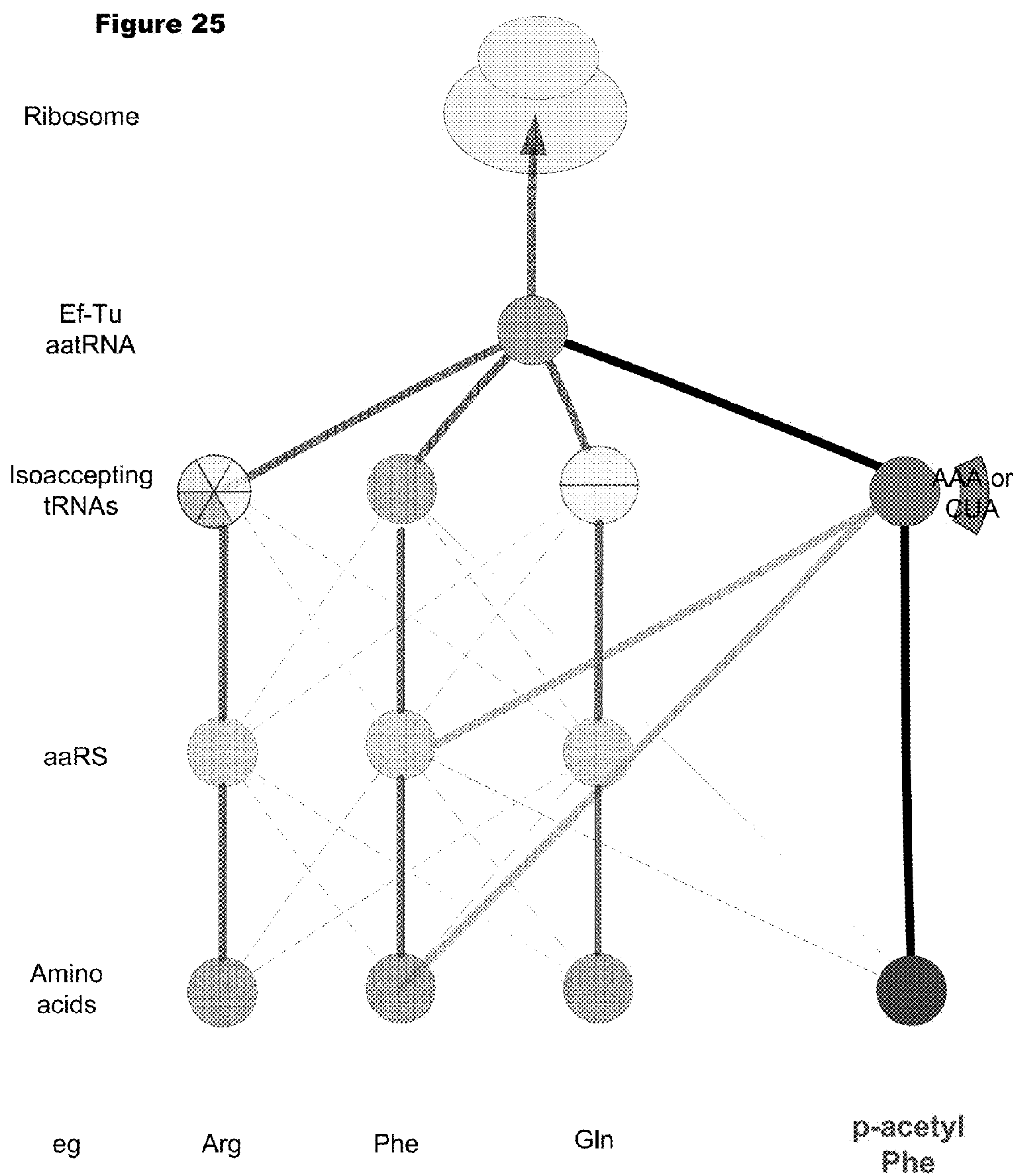
FIG. 25 shows the various cognate (thick dark lines), non-cognate (thin grey lines), or weak non-cognate (thick grey lines) interactions among the amino acids, tRNA synthetases, and isoaccepting tRNAs in the cell-free translation of proteins for incorporation of pAF. The weak non-cognate interactions of $tRNA_{AAA}^{Phe}$ or $tRNA_{CUA}^{Phe}$ with PheRS and Phe are reflected in the observed slow rate of protein synthesis upon addition of $tRNA_{CUA}^{Phe}$ to the cell-free synthesis reaction containing turboGFPY50TAG template as shown in FIG. 23.

Mutagenesis and complementation studies have shown that G34 in the single isoaccepting *E. coli* $tRNA_{GAA}^{Phe}$ is required for aminoacylation. Mutation of G34A or G34C A35U results in a tRNA with 640-fold, and >1000 fold lower aminoacylation, respectively, under normal, $k_{cat}/K_m$ reaction conditions (Peterson, E. C. T. & Uhlenbeck, O. C. (1992) Biochemistry 31: 10380-10389). Cross-charging of $tRNA_{AAA}^{Phe}$ or $tRNA_{AAA}^{Phe}$ by the endogenous Phe tRNA synthetase (PheRS) under normal cell-free conditions should minimized, as indicated by the thick grey line in FIG. 25. Furthermore, the endogenous PheRS activity may be controlled to a certain extent by the addition of active site directed inhibitors and or removal of tagged PheRS from the cell-free extract.

By extension, this approach should also be possible with other wobble codons for the incorporation of other nnAAs. The choice of which wobble codon to "hijack" will depend upon the preferred free energy of interaction. Also, some anticodon bases are post-translationally modified to disfavor wobble codon recognition (see e.g. Sylvers, L. A., Rogers, K. C., Shimizu, M., Ohtsuka, E. and Söll, D. (1993) Biochemistry, 32: 3836-3841). Therefore, the selectivity for the "hijacked" sense codon may be high if the modified tRNA is synthesized in vitro without posttranslational modifications.

Figure 26:
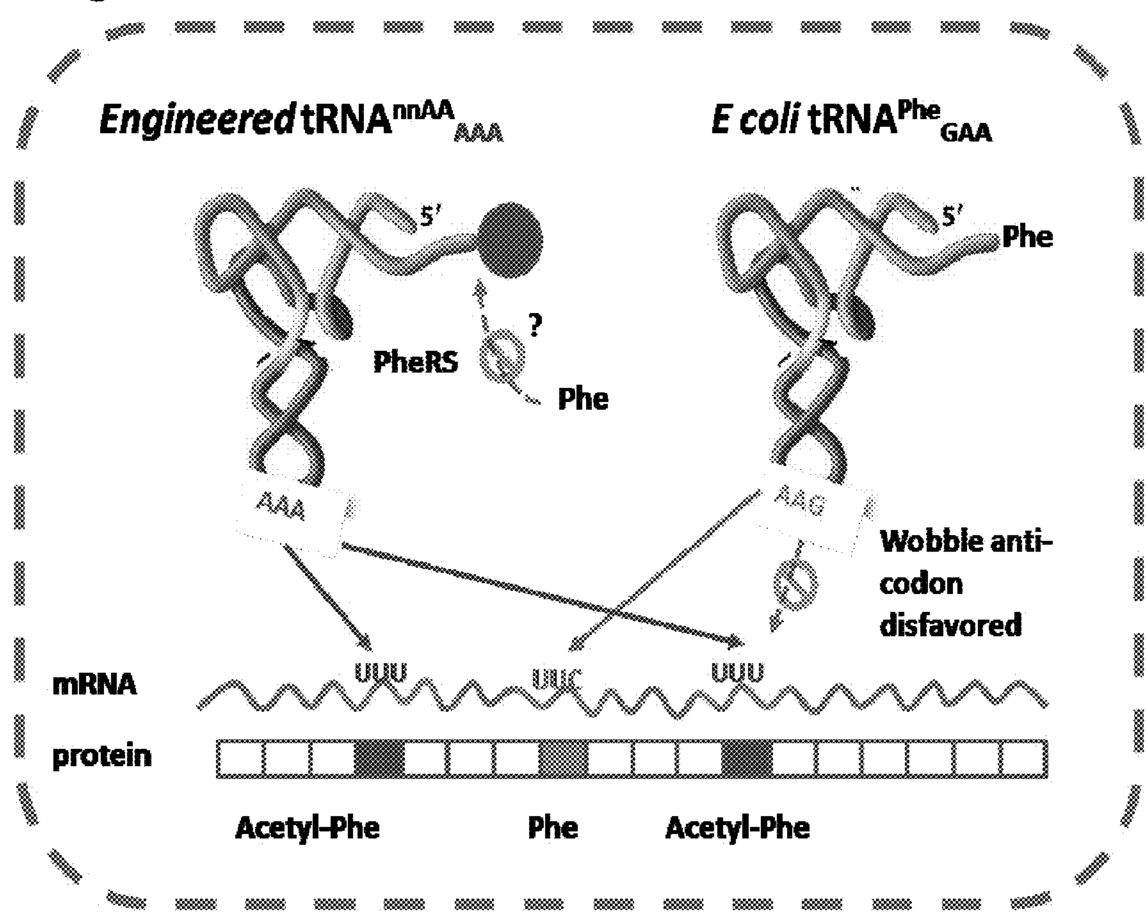
FIG. 26 shows the modified, codon-swapped GM-CSF gene is used for the incorporation of pAF at the TTT Phe120 position.
Figure 27:
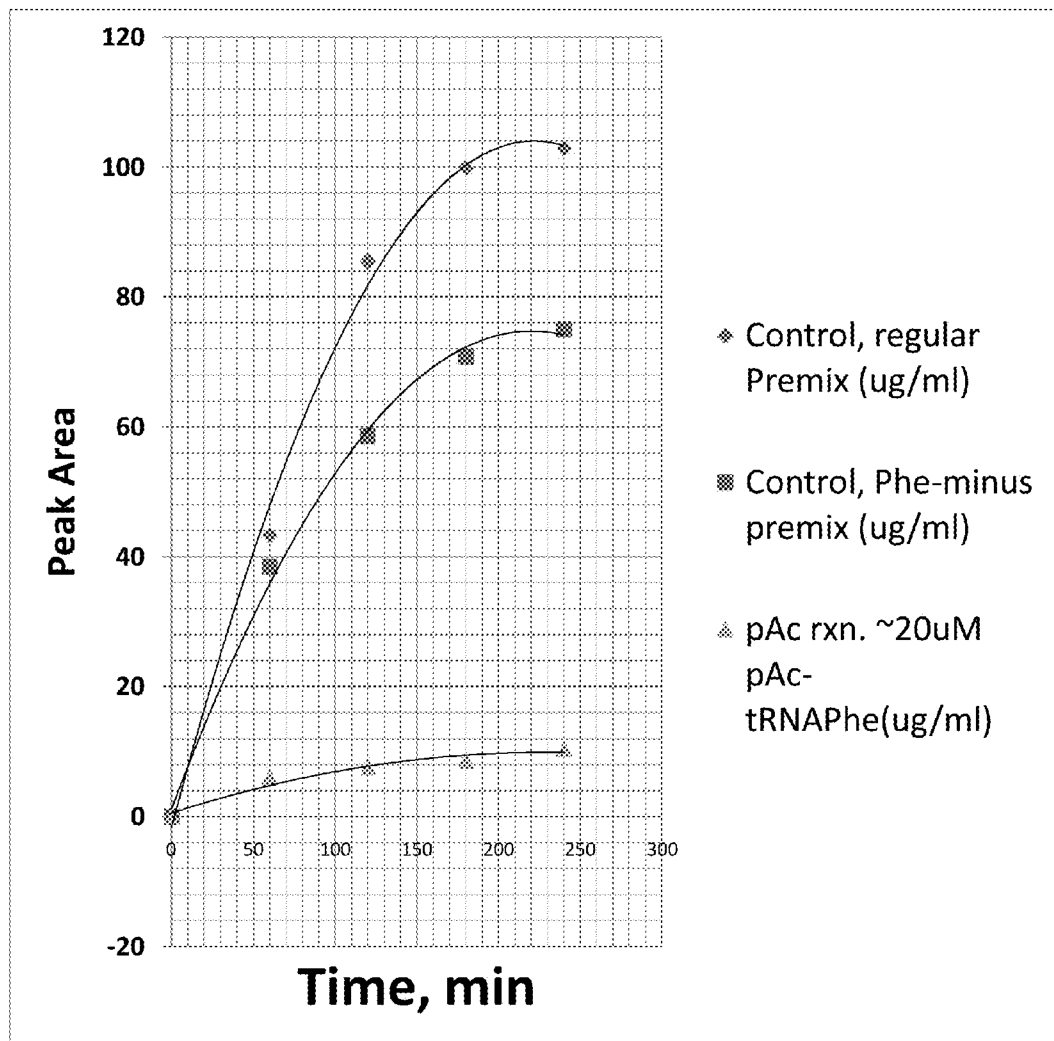
FIG. 27 shows the results of reversed phase HPLC analysis of the incorporation of p-acety Phe into GM-CSF.
Figure 28:
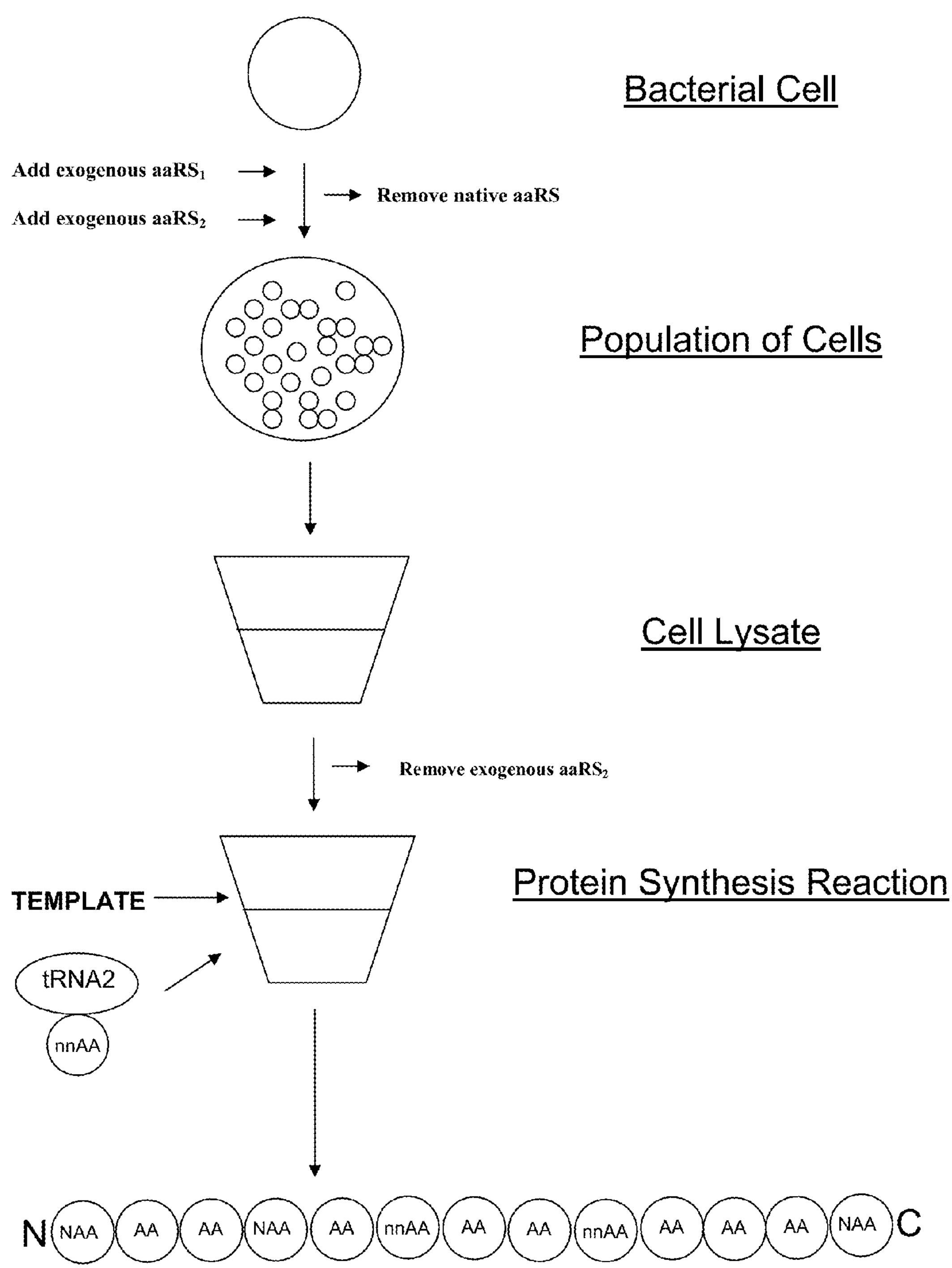
FIG. 28 is a schematic showing a cell-free protein synthesis system as described herein. In this example, the native aminoacyl-tRNA synthetase is depleted prior to cell lysis and replaced with two exogenous aminoacyl-tRNA synthetases, each of which recognizes a distinct isoaccepting sense tRNA molecule. Native aaRS refers to the native aminoacyl-tRNA synthetase. Exogenous $aaRS_1$ and $aaRS_2$ refer to the exogenous aminoacyl-tRNA synthetases. $tRNA_2$ refers the second isoaccepting sense tRNA that is specifically charged by the second exogenous aminoacyl-tRNA synthetase. NAA depicts a native amino acid, and nnAA depicts a non-native amino acid.
Figure 29:
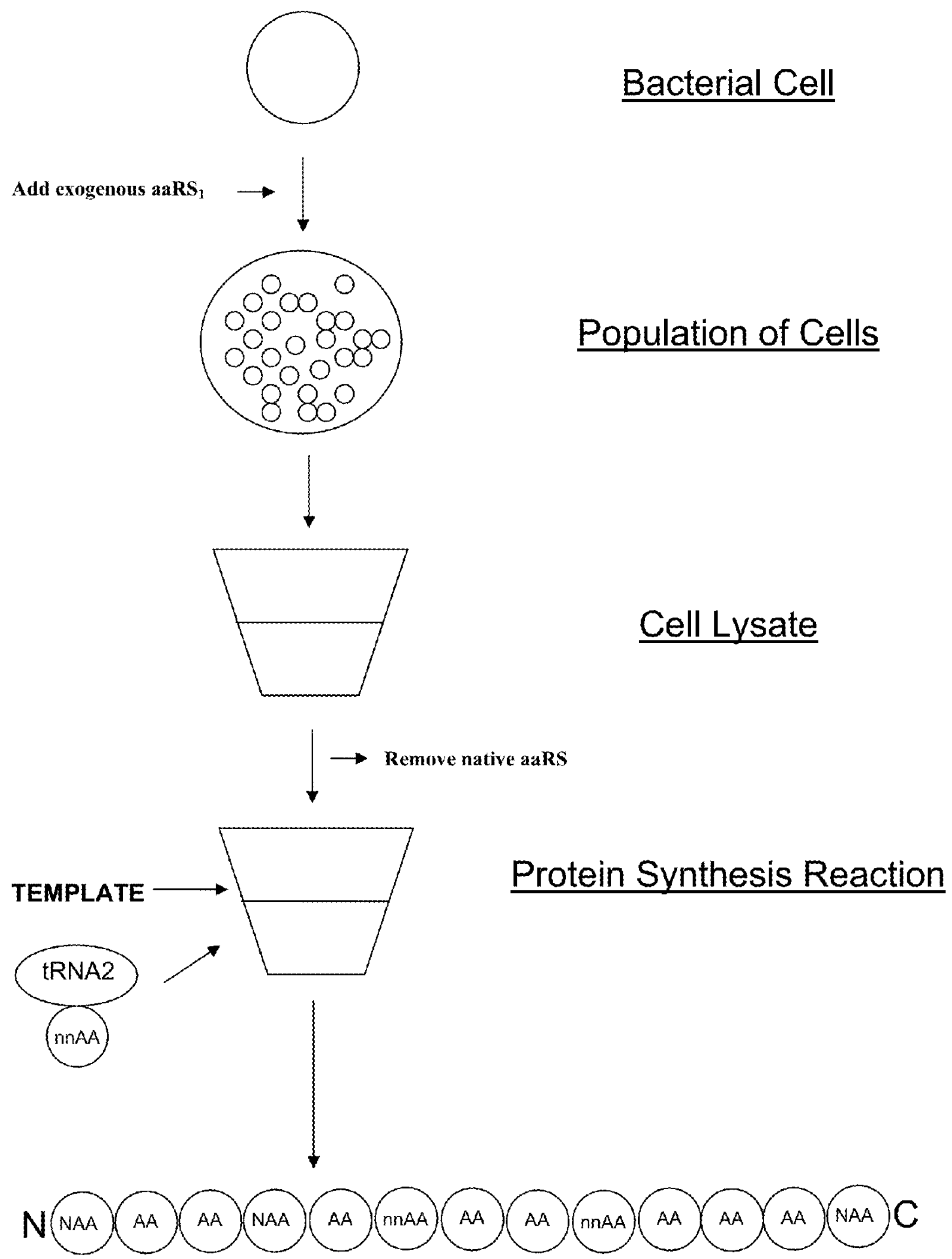
FIG. 29 is a schematic showing a cell-free protein synthesis system as described herein. In this example, the native aminoacyl-tRNA synthetase is depleted following cell lysis, and the second exogenous aminoacyl-tRNA synthetase is expressed in the host cell population. Abbreviations are the same as used in FIG. 27.

GM-CSF contains five Phe residues: Phe48, Phe104, Phe107, Phe114, and Phe120. A gene with only Phe120 encoded by TTT (FIG. 26) was constructed and cloned into pYD317. Using this TTC-to-TTT codon-swapped GM-CSF plasmid DNA, incorporation experiments contained 8 mM magnesium glutamate, 10 mM ammonium glutamate, 130 mM potassium glutamate, 35 mM sodium pyruvate, 1.2 mM AMP, 0.86 mM each of GMP, UMP, & CMP, 2 mM amino acids (1 mM for tyrosine) except for phenylalanine, 4 mM sodium oxalate, 1 mM putrescine, 1.5 mM spermidine, 15 mM potassium phosphate, 100 nM T7 RNA polymerase, 20 nM DNA template, 10 μM *E. coli* DsbC, and 24% (v/v) IAM-treated cell-free extract containing 20 μM pAF-$tRNA_{AAA}^{Phe}$ that was ca. 80% charged was added to the cell-free reaction, is concentration should give a sufficient excess of pAF-$tRNA_{AAA}^{Phe}$ to ensure that pAF is specifically incorporated at position 120. In addition to varying the concentration of pAF-$tRNA_{AAA}^{Phe}$ added to the cell-free reaction and the time of the reaction, phenylalanine was not added to the cell-free reaction in order to lower the recharging of deacylated $tRNA_{AAA}^{Phe}$, indicated by the thick grey line in FIG. 25. Also tested was the addition of 0.5 nM Phe-SA inhibitor to limit cross-charging of $tRNA_{AAA}^{Phe}$. Cell-free reactions were incubated at 30 C for up to 4 h. The product of a cell-free reaction in the presence of pAF-$tRNA_{AAA}^{Phe}$ was purified using reversed phase HPLC (ZORBAX 300SB-C8 5 μm, 4.6×250 mm, Agilent) with gradient elution (buffer A: 100 mM triethylammonium acetate, pH 7.0; buffer B: 70% acetonitrile, 100 mM triethylammonium acetate, pH 7.0) and monitored at 280 nm as shown in FIG. 27. Samples were submitted for analysis by mass spectrometry. The unmodified GM-CSF had a mass of 14604 Da.

Example 13

Obtaining a Template

The present invention requires the use of a nucleic acid template for the cell-free protein synthesis reaction. The following provides an example of generating a template having codon sequences constructed based on placement of non-native amino acids within the desired polypeptide.

An amino acid sequence of human granulocyte macrophage colony stimulating factor (hGMCSF) is obtained from Research Collaboratory for Structural Bioinformatics (RCSB) protein data bank (PDB). A structural DNA gene encoding hGMCSF protein is synthesized de novo (DNA 2.0, Menlo Park, Calif.) such that all, but the second, glutamine amino-acid residues are encoded by the first codon CAA. The second glutamine from the N-terminus of the protein is encoded by the codon CAG. The gene is flanked by the T7 promoter and terminator and is inserted into a plasmid vector containing an *E. coli* origin of replication and kanamycin resistance gene. The circular plasmid DNA template is prepared by transforming XL1Blue (Stratagene, La Jolla, Calif.) strain of *E. coli*, growing up the culture at 37° C. overnight and purifying DNA using a purification kit (Qiagen, Valencia, Calif.).

Example 14

Generating a Lysate Useful for In Vitro Protein Synthesis

A lysate must be generated that will be useful for expressing proteins containing non-native amino acids. This example demonstrates the generation of a lysate from *E. coli* that is modified such that a native aminoacyl-tRNA synthetase is expressed with a 6×His-tag (SEQ ID NO:13) useful for depleting said synthetase as described in subsequent examples.

*E. coli* A19ΔendAΔtonAΔspeAΔtnaAΔsdaAΔsdaBΔgshA ΔgorTrxBHAmet$^{+}$ is first modified such that a DNA fragment encoding 6×His-tag (SEQ ID NO:13) is appended to the native Gln-RS at the C-terminal end in the *E. coli* chromosome.

*E. coli* cells are then grown in a 10 L Braun Biostat C fermentor. The cells are grown on 2YPTG media in batch mode with pH control at pH 7.0. The cells are harvested at 3.2 OD (595) at growth rate of >0.7 per hour. Cells are separated from the media by centrifugation at 6000 g, 4° C. for 25 min and the resulting cell paste is stored at −80° C. The cell paste is thawed at 4° C. in S30 buffer (10 mM TRIS-acetate pH 8.2 (Sigma-Aldrich Corp. St. Louis, Mo.), 14 mM magnesium acetate (Sigma-Aldrich), and 60 mM potassium acetate (Sigma-Aldrich)) at a ratio of 1 mL of buffer per 1 g of wet cell paste. Resuspended cells are passed through a high pressure homogenizer (Emulsiflex C-50, Avestin Inc., Ottawa, Ontario, Canada). The pressure drop is set at 20000 psi. The homogenized mixture is then centrifuged at 30000 g, 4° C. for 30 minutes. The procedure is repeated twice and the supernatant is retained both times. The mixture is incubated at 37° C. for 80 min in a rotary shaker. After the incubation, the extract is dialyzed with 10 diavolumes of S30 buffer at 4° C. using tangential flow filtration across 5000 MWCO membrane (Millipore, Billerica, Mass.).

Example 15

Depletion of the Endogenous Aminoacyl-tRNA Synthetase

The present invention requires inactivation of an endogenous aminoacyl-tRNA synthetase. The purpose of this inactivation is to prevent uncharged isoaccepting tRNAs that would normally have been charged with a non-native amino acids from being mis-aminoacylated with native amino acids.

Endogenous tRNA synthetase expression can be reduced by inactivating or "knocking out" tRNA synthetase nucleic acid sequence(s) or their promoters using targeted homologous recombination of genomic DNA (e.g., see Smithies et al., Nature 317: 230-234 (1985); Thomas and Capecchi, Cell 51: 503-512 (1987); Zhang et al., Nature Biotech 18:1314-1318 (2000)). For example, a mutant, non-functional tRNA synthetase (or a completely unrelated DNA sequence) flanked by DNA homologous to the endogenous tRNA synthetase (either the coding regions or regulatory regions of seryl tRNA synthetase) can be used, with or without a selectable marker and/or a negative selectable marker, to transform cells that express the endogenous tRNA synthetase. Insertion of the DNA construct, via targeted homologous recombination, results in inactivation of the tRNA synthetase.

Targeted homologous recombination can be used to insert a DNA construct comprising a mutant tagged tRNA synthetase in the cell, as described above. In another embodiment, targeted homologous recombination can be used to insert a DNA construct comprising a nucleic acid that encodes a tRNA synthetase polypeptide variant that differs from that present in the cell.

Alternatively, endogenous tRNA synthetase expression can be reduced by targeting deoxyribonucleotide sequences complementary to the regulatory region of a tRNA synthetase gene (i.e. promoter and/or enhancers) to form triple helical structures that prevent transcription of the tRNA synthetase in target cells.

The endogenous aminoacyl-tRNA synthetase in the *E. coli* extract above may be deactivated by addition of micromolar concentration of 5¢-O—[N-(Phenyalanylacyl) sulfamoyl]adenosine during the pretreatment with iodoacetamide, prior to addition of the template DNA as described above.

To remove the chromosomally integrated native 6×his-tag tRNA synthetase as described in Example 2, a volume of the appropriately engineered S30 extract is incubated with varying volumes of pre-equilibrated Ni-NTA magnetic beads (20 mM Tris-HCl, 0.1 M NaCl at pH 7.5) before use for 30 min at 4° C. After removing the beads with the help of a magnetic separator, the remaining extract is used for protein synthesis.

Example 16

Recombinant Expression of an Aminoacyl-tRNA Synthetase

Vectors, Enzyme Expression, and Purification

The separate tRNA charging reactions require the use of an aminoacyl-tRNA synthetase to aminoacylate isoaccepting tRNA molecules. This synthetase can be obtained by expressing a recombinant synthetase as described in this example.

The structural gene for *E. coli* Gln-tRNA synthetase is PCR-amplified from *E. coli* genomic DNA (ATCC #10798D-

5) using the forward and reverse primers as shown in Table 2. PCR products are then cloned into pET23b vector (Novagen, Gibbstown, N.J.) after a double digestion with NdeI and HindIII to generate plasmids, pET23b-GlnRSH (histidine-tagged) and pET23b-GlnRS. The resulting plasmids contain Gln-RS sequences with or without 6×histidine-tag (SEQ ID NO:13) under the control of a T7 promoter for over-expression.

TABLE 2

Primers used for the construction of each type of expression vector

| Name | Type | Sequence |
|---|---|---|
| GlnRSH | | |
| Forward primer | | 5'-AAAAAACATATGAGTGAGGCAG-3' (SEQ ID NO: 1) |
| Reverse primer | C-terminal His tag | 5'-AAAAAAAAGCTTCTCGCCTACTTTC-3' (SEQ ID NO: 2) |
| GlnRS | | |
| Forward primer | Wild type | 5'-AAAAAACATATGAGTGAGGCAG-3' (SEQ ID NO: 1) |
| Reverse primer | | 5'-AAAAAAAAGCTT**TTA**CTCGCCTACTTTC-3' (SEQ ID NO: 3) |

Sequences of the restriction sites are underlined. The stop codon is shown in boldface letters.

GlnRS overproducer plasmid (pET23b-GlnRSH) is transformed into chemically competent BL-21 cells (Promega; Madison, Wis.) and plated on LB/carbenicillin plates. A single colony is grown overnight in TB/100 ug/mL carbenicillin and then used to inoculate a large culture at 1:50 dilution. The cells are grown in rich media to mid-log phase at 37° C. before induction with 1 mM IPTG for 5 h. All subsequent purification steps are carried out at 4° C. Crude cell extracts are prepared by centrifugation at 5000 g, followed by cell-lysis under high pressure. The extracts are mixed with 5 mL of Ni-NTA resin that has been preequilibrated in lysis buffer. After a 1 h incubation of the protein on ice to allow binding to the resin, this mixture is poured into a 10 mL column. Weakly bound proteins are removed with wash buffer (50 mM potassium phosphate, pH 6.0, 300 mM NaCl, 10 mM β-mercaptoethanol, 10% glycerol) until the $A_{280}$ of the eluate drops below 0.1. The protein is eluted with a gradient of 0-0.5 M imidazole in wash buffer. Peak fractions identified by activity or SDS-PAGE are pooled together and dialyzed against buffer containing 50 mM potassium phosphate, pH 7.0, 100 mM KCl, and 10 mM β-mercaptoethanol at 4° C. overnight. Protein is then concentrated to a final concentration of 10 mg/mL in 40% glycerol and then stored at −20° C.

Example 17

Engineering Aminoacyl-tRNA Synthetase Variants

Non-native amino acids cannot usually be charged to isoaccepting sense tRNA molecules by naturally occurring aminoacyl-tRNA synthetases. In some instances, "promiscuous" aminoacyl-tRNA synthetases may previously exist that have the capability to charge isoaccepting tRNAs with non-native amino acids. In other instances wherein no aminoacyl-tRNA synthetases exist with such capability, new aminoacyl-tRNA synthetases must be engineered such that the desired non-native amino acid can be charged to a tRNA molecule in the separate tRNA charging reaction.

Active site residues of a thermostable tRNA synthetases known to be involved in substrate recognition are identified using Pymol molecular viewing software. Residues within 5-10 Å of the amino acid side chain are identified. A 2×20 amino acid=400 member 'library' of site directed variants corresponding to the identified residues is constructed as follows. A cassette library of 35-mer oligonucleotides, representing sense or antisense strands coding for the amino acids on each side of the codons are synthesized (Operon, Huntsville, Ala.) with NNK (where N=G, A, T, C and K=G or T nucleoside triphosphates). Using the Quickchange Multi-site mutagenesis protocol (Stratagene, La Jolla, Calif.), the pooled oligos are annealed to template DNA, amplified by DNA polymerase, plasmid template is degraded with Dpn1, and the library is transformed and plated. Ninety-six clones are sequenced to confirm the diversity of the library.

Example 18

Screening Aminoacyl-tRNA Synthetase Variants for Non-Native-tRNA Charging

High throughput expression of variants engineered as described in Example 5 is conducted in a 96-well format as follows. Plated colonies are transferred by sterile toothpicks to 96-well deep well plates and grown in rich medium to $OD_{600}$=0.5 followed by induction with 1 mM IPTG and overnight growth. The purification is carried out in 96-well format using Millipore Multiscreen filtration plates (Millipore Corp.). Cells are harvested & lysed, the lysate diluted with 4× volume of PBS buffer, and 200 μL is loaded onto Ni-chelating sepharose media in the Multiscreen plate. Enzyme elutions are optimized using increasing concentrations of imidazole. The filtrate is filtered by vacuum filtration and high yields of pure recombinant protein are produced.

The enzyme activity of each variant is assayed using radio-labeled non-native amino acids by a discontinuous steady state assay that monitors the formation of $[^3H]$-labeled nnAA-$tRNA^{nnAA}$ at 37° C. in 50 mM Tris-HCl (or Hepes) pH 7.5, 20 mM KCl, 4 mM DTT, 10 mM $MgCl_2$, 0.2 mg/ml bovine serum albumin, and a range of amino acid, ATP, and tRNA concentrations. The activities are normalized for the enzyme concentration independently determined by fluorescence using a coupled enzyme assay that measures released pyrophosphate.

Example 19

Synthesis of Non-Native Amino Acids

GalNAc L-Threonine is an example of a non-native amino acid, which is synthesized from commercially available GalNAc L-Threonine (N-Fmoc-O-(2-acetamido-3,4,6-tri-O-acetyl-2-deoxy-α-D-galactopyranosyl)-L-threonine (V-Labs, Inc., Covington, La.). The synthesis occurs by selective deprotection of the Fmoc group with piperidine in dichloromethane to give the free amino acid followed by selective enzymatic hydrolysis of the carbohydrate acetates using lipase WG (The sample is purified using reversed phase HPLC).

Example 20 tRNA Charging Reaction

The present invention requires the charging of isoaccepting sense tRNAs with either native or non-native amino acids in a charging reaction separate from the protein synthesis reaction.

tRNA Synthetic DNA oligonucleotides (Integrated DNA Technologies, Inc., Coralville, Iowa) are designed such that the sense strand corresponding to the 5' end of the sequence possesses a 10-bp overlap with the 3' antisense strand. The oligonucleotides used for construction of the *E. coli* tRNA2 Gln gene are: 5'-AAT TCCTGCAGTAATACGACTCAC-TATAGGGGGTATCGCCA AGCGGTAAGGCACCGG-3' (SEQ ID NO:4); 5'-mTmGGCTGGGGTACGAGATTC-GAACCTCGGAATGCCGGAATCAGAAT CCGGTGCCTT-3' (SEQ ID NO:5), where mT and mG represent the 5'-O-methyl nucleotides and the underlined portions represent the overlapped region. Bold type indicates the T7 RNA polymerase promoter. Oligonucleotides are mixed to an equimolar concentration of 4 mM in a reaction solution containing 400 mM dNTPs, 10 mM Tris-HCl, pH 7.5, 10 mM MgSO4, 7.5 mM DTT, and 50 U/mL Klenow fragment polymerase (Promega). The mixture is cycled between 10° C. and 37° C. at 30 s intervals for eight cycles, after which the DNA is precipitated in 65% ethanol/0.3 M sodium acetate, pelleted, and resuspended in 100 mL PMS buffer (5 mM PIPES, pH 7.5/10 mM MgSO4). Transcription is performed in solutions containing 250 mM HEPES-KOH, pH 7+5, 30 mM MgCl2, 2 mM spermidine, 40 mM DTT, 0.1 mg/mL bovine serum albumin, 5 mM dNTPs, 5 mg inorganic pyrophosphatase (Boeringer Mannheim), 50 U RNasin (Amersham), 40 mg/mL T7 RNA polymerase, and 1 mM DNA template from the Klenow extension reaction. The 2-mL reaction mixture is incubated at 37 deg C. for 8-10 h, at which time RQ1 RNase-free DNase (Promega) is added to 10 U/mL and the incubation continued for a further 2-3 hr. The reactions are then loaded on a 5-mL DE-52 (Whatman) column preequilibrated with 100 mM HEPES-KOH, pH 7.5, 12 mM $MgCl_2$, and 200 mM NaCl. The column is washed with 30 mL equilibration buffer and the RNA eluted with a solution of 100 mM HEPES-KOH, pH 7.5, 12 mM $MgCl_2$, 600 mM NaCl. Fractions containing tRNA are dialyzed into PMS buffer and refolded by heating to 70° C., followed by slow cooling to room temperature.

GalNAc L-Gln-tRNA2 The formation of charged GalNAc L-Gln-tRNA2 is catalyzed by a recombinant aaRS as follows. A typical reaction mixture contains 50 mM Tris-HCl (or Hepes) pH 7.5, 20 mM KCl, 4 mM DTT, 10 mM $MgCl_2$, 0.2 mg/ml bovine serum albumin, 1-5 nM aaRS, and a range of amino acid, ATP, and tRNA concentrations. The charged tRNA may be purified by immobilized Ef-Tu chromatography as previously described. The recombinant aaRS used for this charging reaction is described in Ran et al., J. Am. Chem. Soc. 126:15654-55 (2004).

Example 21

In Vitro Protein Synthesis Reaction

The cell-free protein synthesis reaction contains the reagents summarized in Table 3 along with an *E. coli* lysate generated as described in Example 2 and subsequently depleted of a native aminoacyl-tRNA synthetase as described in Example 3.

TABLE 3

Summary of Reagents added the Cell-free Protein Expression system

| Reagent | Concentration |
|---|---|
| Magnesium Glutamate | 8 mM |
| Ammonium Glutamate | 10 mM |
| Potassium Glutamate | 130 mM |
| AMP | 1.20 mM |
| GMP | 0.86 mM |
| UMP | 0.86 mM |
| CMP | 0.86 mM |
| 20 AA | 2 mM |
| GalNAc L-Gln-tRNA2 | 2 mM |
| Gln-Gln-tRNA1 | 2 mM |
| Pyruvate | 30 mM |
| NAD | 3.3 mM |
| CoA | 2.7 mM |
| Oxalic Acid | 4 mM |
| Spermidine | 1.5 mM |
| Putrescine | 1 mM |
| T7 RNA polymerase | 0.10 mg/ml |
| Plasmid | 0.0133 mg/ml |
| *E. coli* DsbC | 75 ug/ml |
| *E. coli* extract | 6/25 total reaction volume |

The extract is pretreated with 100 μM iodoacetamide at 21° C. for 30 min. The plasmid contains the structural gene encoding the target protein and is constructed as explained above. GalNAc L-Gln-tRNA2 is the charged tRNA as described above. The 1 mL of reaction mixture is spread on the bottom of a petri dish (Thermo Fisher Scientific, Rochester, N.Y.) and incubated at 30° C. in a sealed humidified incubator for 4 hours.

What is claimed is:

1. An in vitro method for introducing non-native amino acids into preselected positions of a polypeptide using a cell-free synthesis system, said method comprising:

a) Obtaining a nucleic acid template comprising degenerate sense codons where a first sense codon and a second sense codon correspond to a same native amino acid but differ in their respective nucleotide sequence;

b) Generating a cell lysate in a first reaction vessel wherein a native aminoacyl-tRNA synthetase that aminoacylates the native amino acid is depleted by affinity chromatography, immunoaffinity chromatography or immunoprecipitation;

c) Adding to the lysate a first non-native aminoacyl-tRNA synthetase that selectively aminoacylates a first isoaccepting sense tRNA with a native amino acid; wherein the first isoaccepting sense tRNA corresponds to the first sense codon of the nucleic acid template;

d) Adding a catalytic aminoacylating agent to a second reaction vessel containing a charging reaction mixture including a non-native amino acid and a second isoaccepting sense tRNA corresponding to the second sense codon of the nucleic acid template to generate a tRNA:non-native amino acid charged moiety;

e) Combining the cell lysate with:

1) the tRNA:non-native amino acid charged moiety; and, 2) a nucleic acid template comprising the first and second sense codons under conditions appropriate to generate a polypeptide from the template, wherein the polypeptide bears a non-native amino acid in the position corresponding to the second sense codon; and;

f) Permitting the reaction to generate the polypeptide bearing non-native amino acids in those positions corresponding to the second sense codons of the nucleic acid template.

2. The method of claim 1, wherein the catalytic aminoacylating agent is an aminoacyl-tRNA synthetase.

3. The method of claim 2, wherein the aminoacyl-tRNA synthetase is removed from the charging reaction mixture prior to combining the tRNA:non-native amino acid charged moiety with the cell lysate.

4. The method of claim 1, wherein the catalytic aminoacylating agent is a ribozyme.

5. The method of claim 1, wherein the oxidation phosphorylation system of the cell extract is functioning during protein synthesis.

6. The method of claim 1, wherein the cell lysate is from bacteria.

7. The method of claim 1, wherein the cell lysate is from *Escherichia coli.*

8. The method of claim 1, wherein the non-native amino acids are selected from the group consisting of glycol modified amino acids, metal-chelating groups, aryl-azide containing amino acids, and ketone containing amino acids.

9. The method of claim 1, wherein the cells are rabbit reticulocytes.

10. The method of claim 1, wherein the cells are depleted for arginine decarboxylase.

11. The method of claim 1, further comprising the steps of:

a) transforming the cells used to generate the cell lysate with a gene wherein said gene expresses an aminoacyl-tRNA synthetase fused to a capture moiety that is capable of functionally replacing the native aminoacyl-tRNA synthetase;

b) altering said cells to inhibit expression of the native aminoacyl-tRNA synthetase gene; and, c) depleting the cell lysate of the aminoacyl-tRNA synthetase fused to the capture moiety.

12. The method of claim 11, wherein the aminoacyl-tRNA synthetase fused to a capture moiety is heterologous to the cells forming the cell lysate.

13. The method of claim 11, further comprising the step of depleting the aminoacyl-tRNA synthetase fused to a capture moiety by affinity chromatography.

14. The method of claim 13, wherein the affinity chromatography is immunoaffinity chromatography.

15. The method of claim 11, wherein the aminoacyl-tRNA synthetase fused to a capture moiety is depleted by immunoprecipitation using an antibody that recognizes the capture moiety.

16. The method of claim 1, further comprising the steps of:

a) transforming the cells used to generate the cell lysate with a gene wherein said gene expresses an unstable recombinant aminoacyl-tRNA synthetase that is capable of functionally replacing the native aminoacyl-tRNA synthetase;

b) altering said cells to inhibit expression of the native aminoacyl-tRNA synthetase gene; and, c) depleting the cell lysate of the unstable recombinant aminoacyl-tRNA synthetase.

17. The method of claim 16, wherein the recombinant aminoacyl-tRNA synthetase is thermally unstable.

18. The method of claim 1, further comprising the steps of:

a) transforming the cells used to generate the cell lysate with a first and second gene wherein said first gene expresses the first exogenous aminoacyl-tRNA synthetase and said second gene expresses a second exogenous aminoacyl-tRNA synthetase;

b) altering said cells to inhibit expression of the native aminoacyl-tRNA synthetase; and, c) depleting the cell lysate of the second exogenous aminoacyl-tRNA synthetase.

19. The method of claim 18, wherein the first aminoacyl-tRNA synthetase and the second aminoacyl-tRNA synthetase are from *Acidithiobacillus ferrooxidans.*

20. The method of claim 18, wherein the second exogenous aminoacyl-tRNA synthetase is unstable.

21. The method of claim 20, wherein the second exogenous aminoacyl-tRNA synthetase is thermally unstable.

22. The method of claim 18, wherein the second exogenous aminoacyl-tRNA synthetase is fused to a capture moiety and depleted by affinity chromatography.

23. The method of claim 22, wherein the affinity chromatography is immunoaffinity chromatography.

24. The method of claim 18, wherein the second exogenous aminoacyl-tRNA synthetase is fused to a capture moiety and depleted by immunoprecipitation using an antibody that recognizes the capture moiety.

25. The method of claim 18, wherein the second exogenous aminoacyl-tRNA synthetase is depleted by immunoaffinity chromatography using an antibody that specifically recognizes the second exogenous aminoacyl-tRNA synthetase.

26. The method of claim 18, wherein the second exogenous aminoacyl-tRNA synthetase is depleted by immunoprecipitation using an antibody that specifically recognizes the second exogenous aminoacyl-tRNA synthetase.

27. The method of claim 18, wherein the cell lysate is depleted of the second exogenous aminoacyl-tRNA synthetase by introducing an aminoacyl-tRNA synthetase inhibitor specific to the second exogenous aminoacyl-tRNA synthetase.

28. The method of claim 1, wherein the cell lysate is depleted of the native aminoacyl-tRNA synthetase by immunoprecipitation using an antibody that specifically recognizes the native aminoacyl-tRNA synthetase.

29. The method of claim 1, wherein the cell lysate is depleted of the native aminoacyl-tRNA synthetase by immunoaffinity chromatography using an antibody that specifically recognizes the native aminoacyl-tRNA synthetase.

30. The method of claim 1, where in the cell lysate is depleted of its native aminoacyl-tRNA synthetase by introducing an aminoacyl-tRNA synthetase inhibitor specific to the native aminoacyl-tRNA synthetase.

31. The method of claim 1, wherein the first exogenous aminoacyl-tRNA synthetase that selectively recognizes the first isoaccepting sense tRNA is added to the lysate as a result of transforming the cells prior to lysing with a gene encoding the first exogenous aminoacyl-tRNA synthetase.

* * * * *

UNITED STATES PATENT AND TRADEMARK OFFICE

CERTIFICATE OF CORRECTION

PATENT NO. : 8,778,631 B2
APPLICATION NO. : 12/685795
DATED : July 15, 2014
INVENTOR(S) : Voloshin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 536 days.

Signed and Sealed this
Twenty-fourth Day of November, 2015

Michelle K. Lee

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: synthetic E. coli Gln-tRNA synthase structural
      gene PCR amplification forward primer for
      expression vector pET23b-GlnRSH and expression
      vector pET23b-GlnRS

<400> SEQUENCE: 1

aaaaaacata tgagtgaggc ag                                          22
```

```
<210> SEQ ID NO 2
<211> LENGTH: 25
<212> TYPE: DNA
<213> ORGANISM: Artificial Sequence
<220> FEATURE:
<223> OTHER INFORMATION: synthetic E. coli Gln-tRNA synthase structural
      gene PCR amplification reverse primer for
      expression vector pET23b-GlnRSH

<400> SEQUENCE: 2

aaaaaaaagc ttctcgccta ctttc                                          25


<210> SEQ ID NO 3
<211> LENGTH: 28
<212> TYPE: DNA
<213> ORGANISM: Artificial Sequence
<220> FEATURE:
<223> OTHER INFORMATION: synthetic E. coli Gln-tRNA synthase structural
      gene PCR amplification forward primer for
      expression vector pET23b-GlnRS

<400> SEQUENCE: 3

aaaaaaaagc ttttactcgc ctactttc                                       28


<210> SEQ ID NO 4
<211> LENGTH: 57
<212> TYPE: DNA
<213> ORGANISM: Artificial Sequence
<220> FEATURE:
<223> OTHER INFORMATION: synthetic tRNA DNA oligonucleotide sense strand
      for construction of E. coli tRNA2 Gln gene

<400> SEQUENCE: 4

aattcctgca gtaatacgac tcactatagg gggtatcgcc aagcggtaag gcaccgg       57


<210> SEQ ID NO 5
<211> LENGTH: 55
<212> TYPE: DNA
<213> ORGANISM: Artificial Sequence
<220> FEATURE:
<223> OTHER INFORMATION: synthetic tRNA DNA oligonucleotide 3' antisense
      strand for construction of E. coli tRNA2 Gln gene
<221> NAME/KEY: modified_base
<222> LOCATION: (1)...(1)
<223> OTHER INFORMATION: n = 5'-O-methyl t (mT)
<221> NAME/KEY: modified_base
<222> LOCATION: (2)...(2)
<223> OTHER INFORMATION: n = 5'-O-methyl g (mG)

<400> SEQUENCE: 5

nngctggggt acgagattcg aacctcggaa tgccggaatc agaatccggt gcctt         55


<210> SEQ ID NO 6
<211> LENGTH: 76
<212> TYPE: RNA
<213> ORGANISM: Artificial Sequence
<220> FEATURE:
<223> OTHER INFORMATION: synthetic E. coli isoaccepting Phe-tRNA-GAA
      transcript

<400> SEQUENCE: 6

gcccggauag cucagucggu agagcagggg auugaaaauc cccguguccu ugguucgauu    60

ccgaguccgg gcacca                                                    76


<210> SEQ ID NO 7
<211> LENGTH: 76
<212> TYPE: RNA
<213> ORGANISM: Artificial Sequence
```

```
<220> FEATURE:
<223> OTHER INFORMATION: synthetic partial tRNA-HDV ribozyme sequence
<221> NAME/KEY: modified_base
<222> LOCATION: (1)...(1)
<223> OTHER INFORMATION: c 5' modified by tRNA

<400> SEQUENCE: 7

ccaggccggc augguuccag ccuccucgcu ggcgccggcu gggcaacacc auugcacucc     60

gguggcgaau gggacu                                                     76


<210> SEQ ID NO 8
<211> LENGTH: 38
<212> TYPE: RNA
<213> ORGANISM: Artificial Sequence
<220> FEATURE:
<223> OTHER INFORMATION: synthetic partial hepatitis delta virus (HDV)
      autocatalytic ribozyme consensus sequence

<400> SEQUENCE: 8

ccgaccuggg cauccgagca cucggauggc cucgcggu                             38


<210> SEQ ID NO 9
<211> LENGTH: 14
<212> TYPE: RNA
<213> ORGANISM: Artificial Sequence
<220> FEATURE:
<223> OTHER INFORMATION: synthetic partial hepatitis delta virus (HDV)
      autocatalytic ribozyme consensus sequence

<400> SEQUENCE: 9

gggcaucucc accu                                                       14


<210> SEQ ID NO 10
<211> LENGTH: 15
<212> TYPE: RNA
<213> ORGANISM: Artificial Sequence
<220> FEATURE:
<223> OTHER INFORMATION: synthetic partial hepatitis delta virus (HDV)
      autocatalytic ribozyme consensus sequence

<400> SEQUENCE: 10

ggagagccac uuuuc                                                      15


<210> SEQ ID NO 11
<211> LENGTH: 33
<212> TYPE: RNA
<213> ORGANISM: Artificial Sequence
<220> FEATURE:
<223> OTHER INFORMATION: synthetic partial tRNA

<400> SEQUENCE: 11

gcggauuuag cucaguuggg agagcgccag acu                                  33


<210> SEQ ID NO 12
<211> LENGTH: 47
<212> TYPE: RNA
<213> ORGANISM: Artificial Sequence
<220> FEATURE:
<223> OTHER INFORMATION: synthetic partial tRNA

<400> SEQUENCE: 12

gaucuggagg uccuguguuc gauccacaga auucgcacca gggucgg                   47


<210> SEQ ID NO 13
```

<211> LENGTH: 6
<212> TYPE: PRT
<213> ORGANISM: Artificial Sequence
<220> FEATURE:
<223> OTHER INFORMATION: synthetic 6XHis tag, 6-histidine affinity tag, C-terminal His-tag

<400> SEQUENCE: 13

His His His His His His
1 5

<210> SEQ ID NO 14
<211> LENGTH: 105
<212> TYPE: DNA
<213> ORGANISM: Artificial Sequence
<220> FEATURE:
<223> OTHER INFORMATION: synthetic PCR extension amplification primer for DNA insertion cassette

<400> SEQUENCE: 14
gcgtatcaac aaagcgctgg attttattgc tgaacgcgaa aatcagcagg gtggcgacta 60
caaagatgac gatgacaaat aaaattaacc ctcactaaag ggcgg 105

<210> SEQ ID NO 15
<211> LENGTH: 74
<212> TYPE: DNA
<213> ORGANISM: Artificial Sequence
<220> FEATURE:
<223> OTHER INFORMATION: synthetic PCR extension amplification primer for DNA insertion cassette

<400> SEQUENCE: 15
agggattatc ggattgttac aacgcttagg gattcgcgat agcaaataat taatacgact 60
cactataggg ctcg 74

<210> SEQ ID NO 16
<211> LENGTH: 28
<212> TYPE: DNA
<213> ORGANISM: Artificial Sequence
<220> FEATURE:
<223> OTHER INFORMATION: synthetic amplification primer for DNA fragment including 3' end and gltX downstream sequence

<400> SEQUENCE: 16
gttcaacacc gacaagctgc tgtggctg 28

<210> SEQ ID NO 17
<211> LENGTH: 31
<212> TYPE: DNA
<213> ORGANISM: Artificial Sequence
<220> FEATURE:
<223> OTHER INFORMATION: synthetic amplification primer for DNA fragment including 3' end and gltX downstream sequence

<400> SEQUENCE: 17
gcgggaaggg attatcggat tgttacaacg c 31

<210> SEQ ID NO 18
<211> LENGTH: 20
<212> TYPE: DNA
<213> ORGANISM: Artificial Sequence
<220> FEATURE:
<223> OTHER INFORMATION: synthetic primer for confirming Flag-tag encoding sequence

<400> SEQUENCE: 18
gattactgac tggaccgctg 20

<210> SEQ ID NO 19
<211> LENGTH: 8
<212> TYPE: PRT
<213> ORGANISM: Artificial Sequence
<220> FEATURE:
<223> OTHER INFORMATION: synthetic Flag-tag sequence

<400> SEQUENCE: 19

Asp Tyr Lys Asp Asp Asp Asp Lys
1 5

<210> SEQ ID NO 20
<211> LENGTH: 31
<212> TYPE: DNA
<213> ORGANISM: Artificial Sequence
<220> FEATURE:
<223> OTHER INFORMATION: synthetic DNA sequence back translated from Flag-tag peptide

<400> SEQUENCE: 20
gggtggcgac tacaaagatg acgatgacaa a 31

<210> SEQ ID NO 21
<211> LENGTH: 23
<212> TYPE: DNA
<213> ORGANISM: Artificial Sequence
<220> FEATURE:
<223> OTHER INFORMATION: synthetic amplifying sequence at 3' end of forward primer

<400> SEQUENCE: 21
aattaaccct cactaaaggg cgg 23

<210> SEQ ID NO 22
<211> LENGTH: 24
<212> TYPE: DNA
<213> ORGANISM: Artificial Sequence
<220> FEATURE:
<223> OTHER INFORMATION: synthetic amplifying sequence of backward primer

<400> SEQUENCE: 22
taatacgact cactataggg ctcg 24

<210> SEQ ID NO 23
<211> LENGTH: 31
<212> TYPE: DNA
<213> ORGANISM: Artificial Sequence
<220> FEATURE:
<223> OTHER INFORMATION: synthetic DNA sequence attached to 3' end of gltX gene in KGK10 chromosome encoding two Gly residue dipeptide and Flag-tag sequence

<400> SEQUENCE: 23
gggtggcgac tacaaagatg acgatgacaa a 31

<210> SEQ ID NO 24
<211> LENGTH: 10
<212> TYPE: PRT
<213> ORGANISM: Artificial Sequence
<220> FEATURE:
<223> OTHER INFORMATION: synthetic two Gly residue dipeptide connected to Flag-tag sequence

<400> SEQUENCE: 24

-continued

```
Gly Gly Asp Tyr Lys Asp Asp Asp Asp Lys
1               5                   10
```